US012158399B2

(12) United States Patent
Racioppi et al.

(10) Patent No.: US 12,158,399 B2
(45) Date of Patent: Dec. 3, 2024

(54) CaMKK2 INHIBITOR COMPOSITIONS AND METHODS OF USING THE SAME

(71) Applicant: Duke University, Durham, NC (US)

(72) Inventors: Luigi Racioppi, Durham, NC (US); Erik Nelson, Durham, NC (US); Wei Huang, Durham, NC (US); Nelson Chao, Durham, NC (US); Donald McDonnell, Durham, NC (US)

(73) Assignee: Duke University, Durham, NC (US)

( * ) Notice: Subject to any disclaimer, the term of this patent is extended or adjusted under 35 U.S.C. 154(b) by 183 days.

(21) Appl. No.: 16/323,482

(22) PCT Filed: Aug. 7, 2017

(86) PCT No.: PCT/US2017/045749

§ 371 (c)(1),
(2) Date: Feb. 5, 2019

(87) PCT Pub. No.: WO2018/027223

PCT Pub. Date: Feb. 8, 2018

(65) Prior Publication Data

US 2019/0167776 A1 Jun. 6, 2019

Related U.S. Application Data

(60) Provisional application No. 62/371,309, filed on Aug. 5, 2016.

(51) Int. Cl.

| | |
|---|---|
| ***A61P 35/00*** | (2006.01) |
| ***A61K 35/17*** | (2015.01) |
| ***A61K 38/00*** | (2006.01) |
| ***A61K 39/00*** | (2006.01) |
| ***G01N 33/569*** | (2006.01) |
| ***G01N 33/574*** | (2006.01) |

(52) U.S. Cl.

CPC ....... *G01N 33/56972* (2013.01); *A61K 35/17* (2013.01); *A61K 39/001129* (2018.08); *A61P 35/00* (2018.01); *G01N 33/57415* (2013.01); *A61K 38/00* (2013.01); *G01N 2800/50* (2013.01)

(58) Field of Classification Search

CPC ............ A61K 39/001129; A61K 35/17; A61K 38/00; G01N 33/56972; G01N 33/57415; G01N 2800/50; A61P 35/00

See application file for complete search history.

(56) References Cited

U.S. PATENT DOCUMENTS

| | | | | |
|---|---|---|---|---|
| 7,521,056 | B2 | 4/2009 | Chang | |
| 7,527,787 | B2 | 5/2009 | Chang | |
| 7,534,866 | B2 | 5/2009 | Chang | |
| 7,550,143 | B2 | 6/2009 | Chang | |
| 7,666,400 | B2 | 2/2010 | Chang | |
| 2013/0059851 | A1 | 3/2013 | Garraway | |
| 2013/0253035 | A1 | 9/2013 | McDonnell | |
| 2015/0153349 | A1* | 6/2015 | Galon | G01N 33/57492 435/7.23 |
| 2016/0159905 | A1* | 6/2016 | Abdiche | A61K 39/39 424/139.1 |
| 2017/0027928 | A1* | 2/2017 | McDonnell | A61K 31/7088 |

FOREIGN PATENT DOCUMENTS

| | | | |
|---|---|---|---|
| EP | 0453082 | A1 | 10/1991 |
| WO | 2007045996 | A1 | 4/2007 |
| WO | 2013044169 | A1 | 3/2013 |
| WO | 2016115345 | A1 | 7/2016 |

OTHER PUBLICATIONS

Lin et al., Hepatology 62(2): 505-520, Apr. 4, 2015.*

Huang, Wei. Calcium/Calmodulin-Dependent Protein Kinase Kinase 2 (CaMKK2) Regulates Dendritic Cells and Myeloid Derived Suppressor Cells Development in the Lymphoma Microenvironment. 154 pages.*

Qian et al. (PLoS One 4(8): 1-16, published Aug. 10, 2009).*

Racioppi, L. et al. "CaMKK2 in myeloid cells is a key regulator of the immune-suppressive microenvironment in breast cancer" Nat Commun 10, 2450 (2019). https://doi.org/10.1038/s41467-019-10424-5.

Topalian, S. L., et al. "Mechanism-driven biomarkers to guide immune checkpoint blockade in cancer therapy." Nature Reviews Cancer 16.5 (2016): 275-287.

Ugel, S., et al. "Tumor-induced myeloid deviation: when myeloid-derived suppressor cells meet tumor-associated macrophages." The Journal of clinical investigation 125.9 (2015): 3365-3376.

UniProtKB—E2R3S0 (E2R3SO_CANLF). Version dated Jun. 2, 2021. Accessed online at http://www.uniprot.org/uniprot/E2R3S0.

UniProtKB—F6RN62 (F6RN62_HORSE). Version dated Jun. 2, 2021. Accessed online at http://www.uniprot.org/uniprot/F6RN62.

UniProtKB—G1U863 (G1U863_RABIT). Version dated Jun. 2, 2021. Accessed online at http://www.uniprot.org/uniprot/G1U863.

UniProtKB—H0VA11 (H0VA11_CAVPO). Version dated Jun. 2, 2021. Accessed online at http://www.uniprot.org/uniprot/H0VA11.

(Continued)

*Primary Examiner* — Alana Harris Dent

(74) *Attorney, Agent, or Firm* — Quarles & Brady, LLP

(57) ABSTRACT

Provided herein are compositions including a CaMKK2 inhibitor and an anti-cancer therapeutic agent and methods of treating cancer in a subject by administering a therapeutically effective amount of the composition to a subject. The subject may be selected for treatment based on an immune cell measurement of a sample from the subject. Methods of treating cancer by administering a therapeutically effective amount of a CaMKK2 inhibitor, and administering a therapeutically effective amount of an anti-cancer therapeutic agent to the subject are also provided. Kits including combination of a CaMKK2 inhibitor and another anti-cancer therapeutic agent are also provided.

9 Claims, 51 Drawing Sheets

Specification includes a Sequence Listing.

(56) References Cited

OTHER PUBLICATIONS

UniProtKB—M3WGZ4 (M3WGZ4_FELCA). Version dated Jun. 2, 2021. Accessed online at http://www.uniprot.org/uniprot/M3WGZ4.
UniProtKB—O88831 (KKCC2_RAT). Version dated Jun. 2, 2021. Accessed online at http://www.uniprot.org/uniprot/O88831.
UniProtKB—Q148H3 (Q148H3_BOVIN). Version dated Jun. 2, 2021. Accessed online at http://www.uniprot.org/uniprot/Q148H3.
UniProtKB—Q8C078 (KKCC2_MOUSE). Version dated Jun. 2, 2021. Accessed online at http://www.uniprot.org/uniprot/Q8C078.
UniProtKB—Q96RR4 (KKCC2_HUMAN). Version dated Jun. 2, 2021. Accessed online at http://www.uniprot.org/uniprot/Q96RR4.
UniProtKB—W5Q048 (W5Q048_SHEEP). Version dated Jun. 2, 2021. Accessed online at http://www.uniprot.org/uniprot/W5Q048.
UniProtKB—W5Q050 (W5Q050_SHEEP). Version dated Jun. 2, 2021. Accessed online at http://www.uniprot.org/uniprot/W5Q050.
Wang B et al., Transition of tumor-associated macrophages from MHC class II(hi) to MHC class II(low) mediates tumor progression in mice. BMC Immunol 12, 43 (2011).
Wang, K et al., Tumor-infiltrating lymphocytes in breast cancer predict the response to chemotherapy and survival outcome: A meta-analysis. Oncotarget, (2016).
Williams, C. B., et al. (2016). Tumor-associated macrophages: unwitting accomplices in breast cancer malignancy. NPJ breast cancer, 2(1), 1-12.
Woods, A., et al. (2005). Ca2+/calmodulin-dependent protein kinase kinase-ß acts upstream of AMP-activated protein kinase in mammalian cells. Cell metabolism, 2(1), 21-33.
Yang, Z et al., Macrophage alpha1 AMP-activated protein kinase (alpha1AMPK) antagonizes fatty acid-induced Inflammation through SIRT1. The Journal of biological chemistry 285, 19051-19059 (2010).
Anderson, KA et al., Hypothalamic CaMKK2 contributes to the regulation of energy balance. Cell metabolism 7, 377-388 (2008).
Bronte V. Myeloid-derived suppressor cells in inflammation: uncovering cell subsets with enhanced immunosuppressive functions. Eur J Immunol. 2009;39(10):2670-2672.
Carroll, KC et al., AMPKa1 deficiency amplifies proinflammatory myeloid APC activity and CD40 signaling. J Leukoc Biol 94, 1113-1121 (2013).
Coussens LM, et al. Neutralizing tumor-promoting chronic inflammation: a magic bullet? Science. 2013;339 (6117):286-291.
Denardo DG et al., Leukocyte complexity predicts breast cancer survival and functionally regulates response to chemotherapy. Cancer Discov 1, 54-67 (2011).
Frigo DE, et al. CaM kinase kinase beta-mediated activation of the growth regulatory kinase AMPK is required for androgen-dependent migration of prostate cancer cells. Cancer research. 2011;71(2):528-537.
Gabrilovich DI, et al. Myeloid-derived suppressor cells as regulators of the immune system. Nat Rev Immunol. 2009;9(3):162-174.
Gabrilovich DI, et al. The terminology issue for myeloid-derived suppressor cells. Cancer Res. 2007;67(1):425; author reply 426.
Galic S et al., Hematopoietic AMPK beta1 reduces mouse adipose tissue macrophage inflammation and insulin resistance in obesity. The Journal of clinical investigation, (2011).
Galon, J., et al. "Cancer classification using the Immunoscore: a worldwide task force." Journal of translational medicine 10.1 (2012): 1-10.
Galon, J., et al. "Type, density, and location of immune cells within human colorectal tumors predict clinical outcome." Science 313.5795 (2006): 1960-1964.
Georgoudaki AM et al., Reprogramming Tumor-Associated Macrophages by Antibody Targeting Inhibits Cancer Progression and Metastasis. Cell Rep 15, 2000-2011 (2016).
Gong S et al. (2003). A gene expression atlas of the central nervous system based on bacterial artificial chromosomes. Nature, 425(6961), 917-925.
Green MF, et al. Characterization of the CaMKKbeta-AMPK signaling complex. Cellular signalling. 2011;23 (12):2005-2012.
Grupp, et al. "Chimeric antigen receptor-modified T cells for acute lymphoid leukemia." New England Journal of Medicine 368.16 (2013): 1509-1518.
Guy, et al., Induction of mammary tumors by expression of polyomavirus middle T oncogene: a transgenic mouse model for metastatic disease. Mol Cell Biol 12, 954-961 (1992).
Györffy B et al., An online survival analysis tool to rapidly assess the effect of 22,277 genes on breast cancer prognosis using microarray data of 1,809 patients. Breast Cancer Res Treat 123, 725-731 (2010).
Hardie DG. AMPK—sensing energy while talking to other signaling pathways. Cell Metab. 2014;20(6):939-952.
Hawley Sa, et al. Calmodulin-dependent protein kinase kinase-beta is an alternative upstream kinase for AMP-activated protein kinase. Cell metabolism. 2005;2(1):9-19.
Heller et al., Downregulation of TSLC1 and DAL-1 expression occurs frequently in breast cancer. Breast Cancer Res Treat 103, 283-291 (2007).
International Searching Authority. International Search Report and Written Opinion for application PCT/US2017/045749. Mailed on Oct. 25, 2017. 11 pages.
Kirilovsky, A., et al. "Rational bases for the use of the Immunoscore in routine clinical settings as a prognostic and predictive biomarker in cancer patients." International immunology 28.8 (2016): 373-382.
Kumar V, et al. CD45 Phosphatase Inhibits STAT3 Transcription Factor Activity in Myeloid Cells and Promotes Tumor-Associated Macrophage Differentiation. Immunity. 2016;44(2):303-315.
Laoui D et al., Tumor hypoxia does not drive differentiation of tumor-associated macrophages but rather fine-tunes the M2-like macrophage population. Cancer Res 74, 24-30 (2014).
Leek RD, et al. Association of macrophage infiltration with angiogenesis and prognosis in invasive breast carcinoma. Cancer Res. 1996;56(20):4625-4629.
Liddy, N., et al. "Monoclonal TCR-redirected tumor cell killing." Nature medicine 18.6 (2012): 980-987.
Mahmoud SM et al. (2012). Tumour-infiltrating macrophages and clinical outcome in breast cancer. Journal of clinical pathology, 65(2), 159-163.
Mantovani, A., et al. (2015). The interaction of anticancer therapies with tumor-associated macrophages. Journal of Experimental Medicine, 212(4), 435-445.
Massie CE et al., The androgen receptor fuels prostate cancer by regulating central metabolism and biosynthesis. The EMBO journal 30, 2719-2733 (2011).
Medrek C, et al. The presence of tumor associated macrophages in tumor stroma as a prognostic marker for breast cancer patients. BMC Cancer. 2012;12:306.
Milstein, et al. "Hybrid hybridomas and their use in immunohistochemistry." Nature 305.5934 (1983): 537-540.
Mounier R et al., AMPKa1 regulates macrophage skewing at the time of resolution of inflammation during skeletal muscle regeneration. Cell Metab 18, 251-264 (2013).
Movahedi, K et al. (2010). Different tumor microenvironments contain functionally distinct subsets of macrophages derived from Ly6C (high) monocytes. Cancer research, 70(14), 5728-5739.
Newick, K., et al. (2016). Chimeric antigen receptor T-cell therapy for solid tumors. Molecular Therapy-Oncolytics, 3, 16006.
Nitta, T., et al. "Preliminary trial of specific targeting therapy against malignant glioma." The Lancet 335.8686 (1990): 368-371.
Noy R, et al. Tumor-associated macrophages: from mechanisms to therapy. Immunity. 2014;41(1):49-61.
Pages, F., et al. "Effector memory T cells, early metastasis, and survival in colorectal cancer." New England journal of medicine 353.25 (2005): 2654-2666.
Qian BZ, et al. Macrophage diversity enhances tumor progression and metastasis. Cell. 2010;141(1):39-51.
Racioppi L, et al. Calcium/calmodulin-dependent protein kinase kinase 2: roles in signaling and pathophysiology. J Biol Chem. 2012;287(38):31658-31665.
Racioppi, et al., Calcium/calmodulin-dependent protein kinase kinase 2 regulates macrophage-mediated Inflammatory responses. J Biol Chem 287, 11579-11591 (2012).

(56) References Cited

OTHER PUBLICATIONS

Rosenberg SA et al. “Adoptive cell transfer: a clinical path to effective cancer immunotherapy.” Nature Reviews Cancer 8.4 (2008): 299-308.
Ruffell, B., et al. (2014). Macrophage IL-10 blocks CD8+ T cell-dependent responses to chemotherapy by suppressing IL-12 expression in intratumoral dendritic cells. Cancer cell, 26(5), 623-637.
Sag, D. et al., Adenosine 5'-monophosphate-activated protein kinase promotes macrophage polarization to an anti-Inflammatory functional phenotype. Journal of immunology 181, 8633-8641 (2008).
Schafer CC, et al. Indoleamine 2,3-dioxygenase regulates anti-tumor immunity in lung cancer by metabolic reprogramming of immune cells in the tumor microenvironment. Oncotarget. 2016;7(46):75407-75424.
Schmid MC, et al. Myeloid cells in the tumor microenvironment: modulation of tumor angiogenesis and tumor Inflammation. J Oncol. 2010;2010:201026.
Schreiber RD, et al. Cancer immunoediting: integrating immunity’s roles in cancer suppression and promotion. Science. 2011;331(6024):1565-1570.
Solinas, G., et al. (2009). Tumor-associated macrophages (TAM) as major players of the cancer-related Inflammation. Journal of leukocyte biology, 86(5), 1065-1073.
Sood AK et al., Expression characteristics of prostate-derived Ets factor support a role in breast and prostate cancer progression. Hum Pathol 38, 1628-1638 (2007).
Staerz, U. D., et al. “Hybrid antibodies can target sites for attack by T cells.” Nature 314.6012 (1985): 628-631.
Teng EC, et al. A cell-intrinsic role for CaMKK2 in granulocyte lineage commitment and differentiation. J Leukoc Biol. 2011;90(5):897-909.

* cited by examiner

Figure 2A-C

Tumor size (mm3)
2000
1500
1000
500
0
0 5 10 15 20 25 30 35 40 45
Time (days)
WT
Camkk2-/-

Tumor size (mm3)
4000
3000
2000
1000
0
0 20 40 60 80 100
Time (Days)
WT
Camkk2-/-

WT
Camkk2-/-
CD3
F4/80
Cell/field
15
10
5
0
CD3
F4/80
**
*
WT
Camkk2-/-
WT
Camkk2-/-

Figure 5A-C
Fig. 5A
Fig. 5B
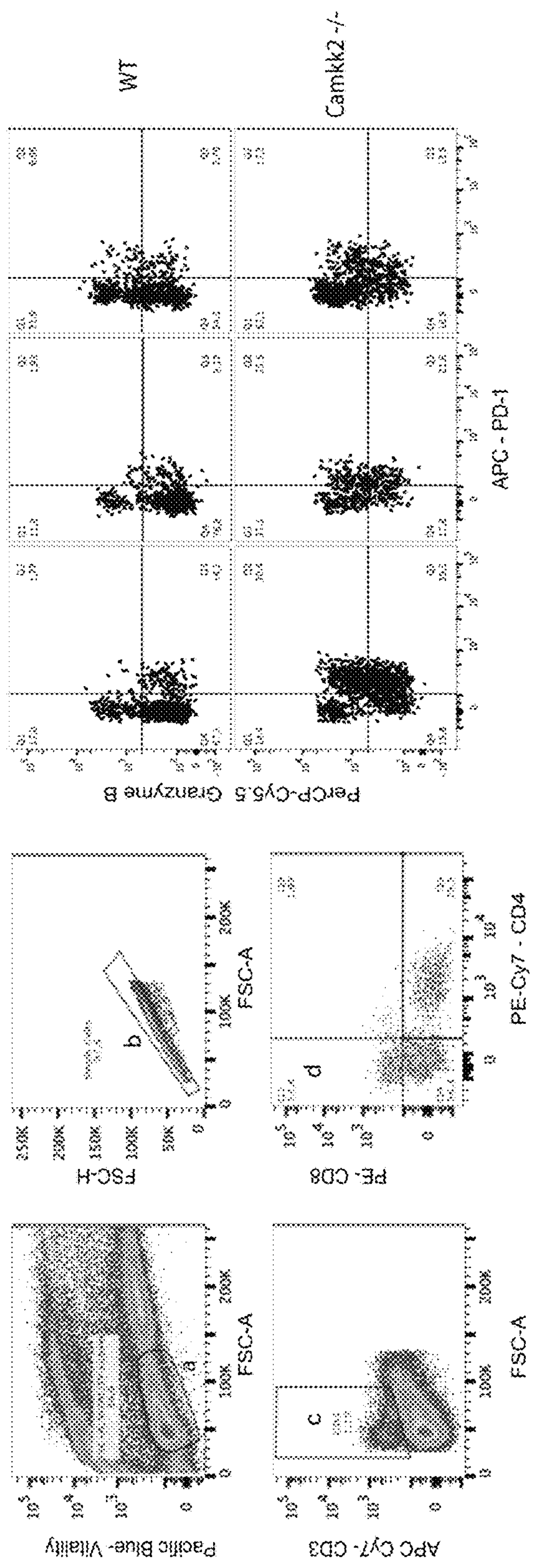
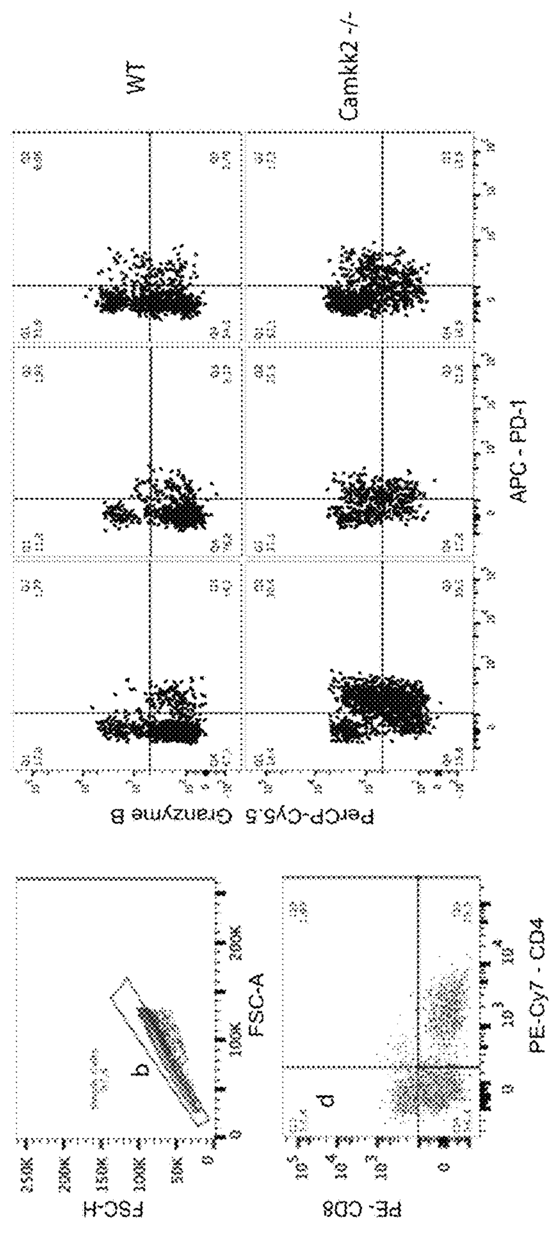
Fig. 5C
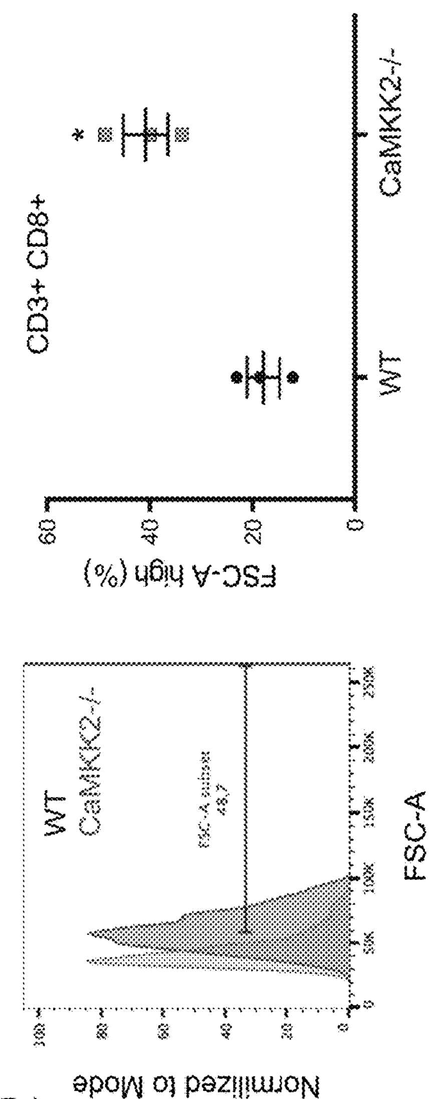

Figure 6A-B

WT
Camkk2-/-

Myeloid subsets (%parents)

Figure 10A-C
Fig. 10A
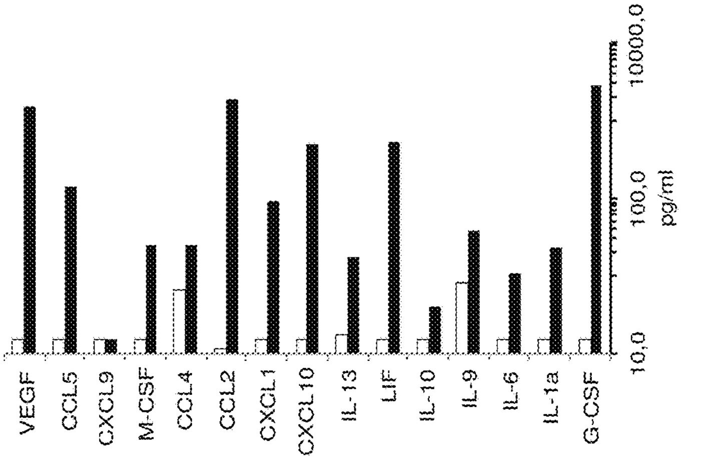
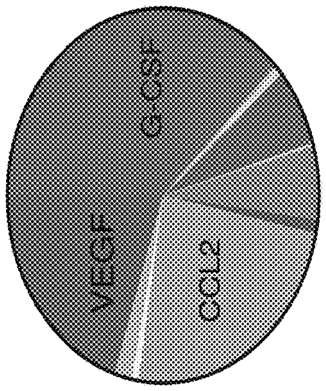
Fig. 10B
Fig. 10C
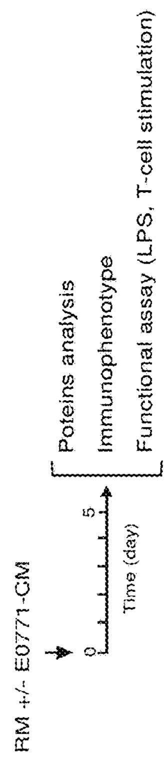

Nos2
Chil3/Ym1
Retnla/Fizz1
Fold change
WT RM
WT CM
KO RM
KO CM

WT
KO
WT
KO
M1
M1/DC
M2
Z-score
RM
TCM
Camkk2
Cxcl11
Socs1
Rssd2
Pla1a
IL2a
Nos2
Kynu
Cd40
Nod2
Cd38
Arrb1
Serpinb2
Scl7a11
Stgal6
Htr2b
Ccl5
Nr4a3
Cd86
Cxcl10
Dhx58
Ccl8
Cd80
Siglec1
Il12b
Cpy27a1
Chil3
Ccl22
Rnase6
Rassf4
Cd33
Slc13a3
Fcgr1
Myc
Egr2
Scl40a1

Reactome Cholesterol Biosynthesis

TCM
WT KO

NES: 2.123648
Norm p-value 0.000

Browne Interferon Responsive Genes

Figure 18A-D
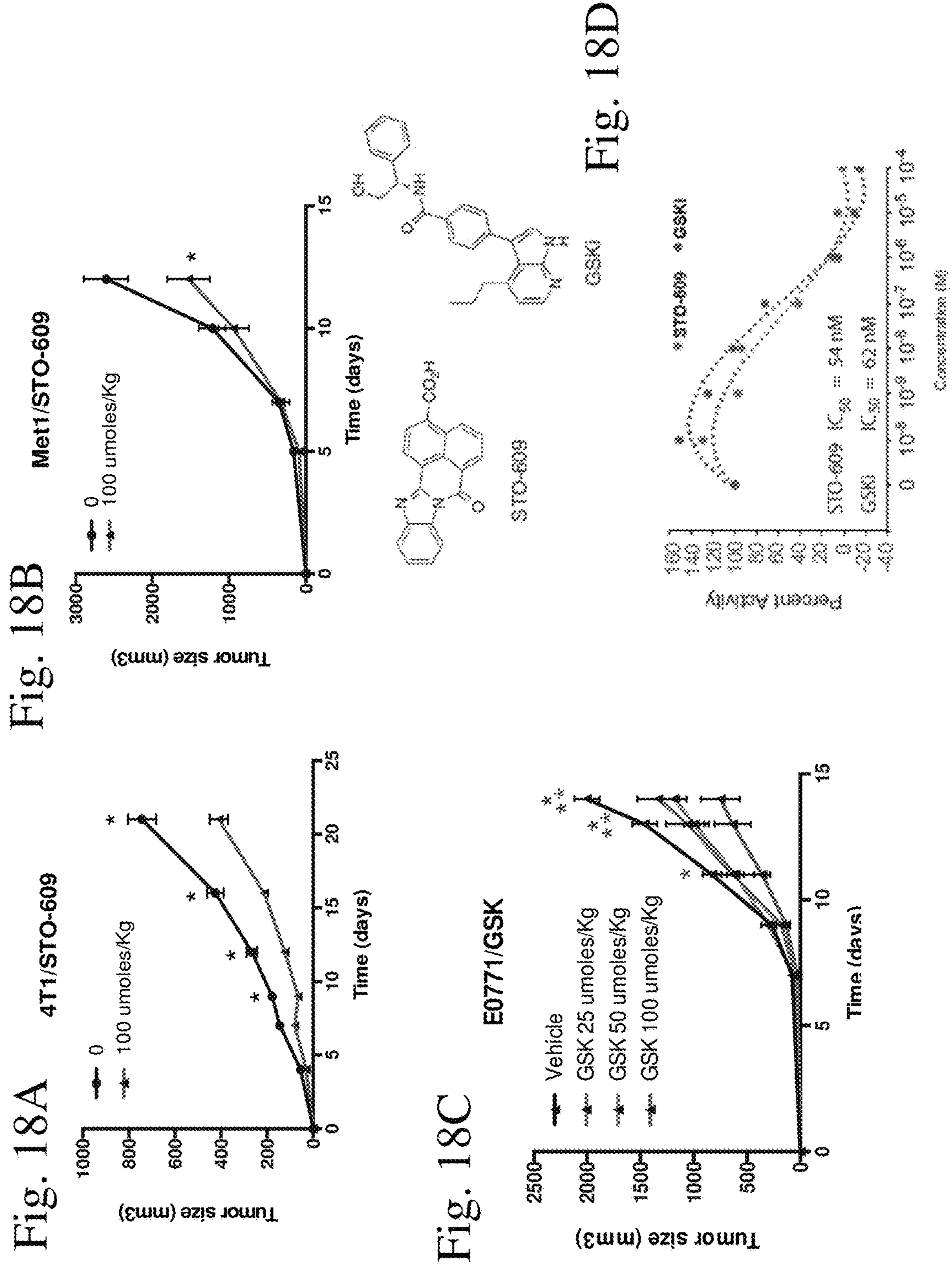

Figure 19A-C
Fig. 19A
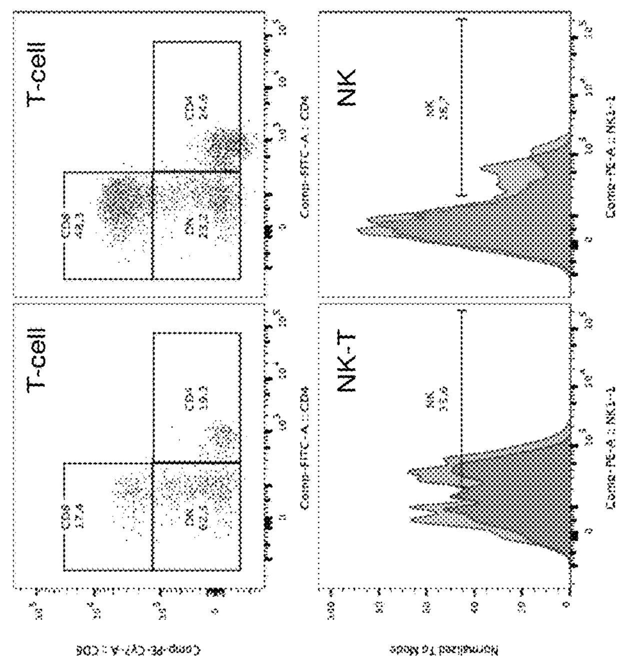
Fig. 19B
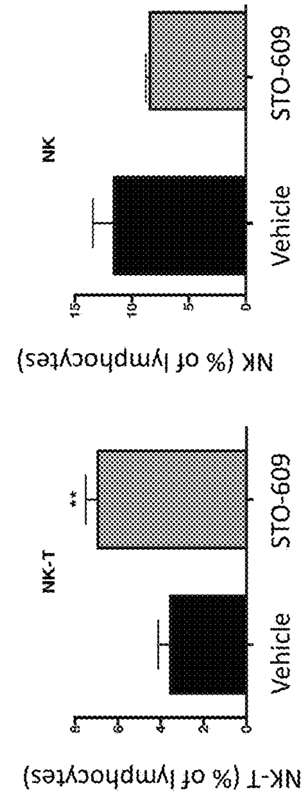
Fig. 19C
C
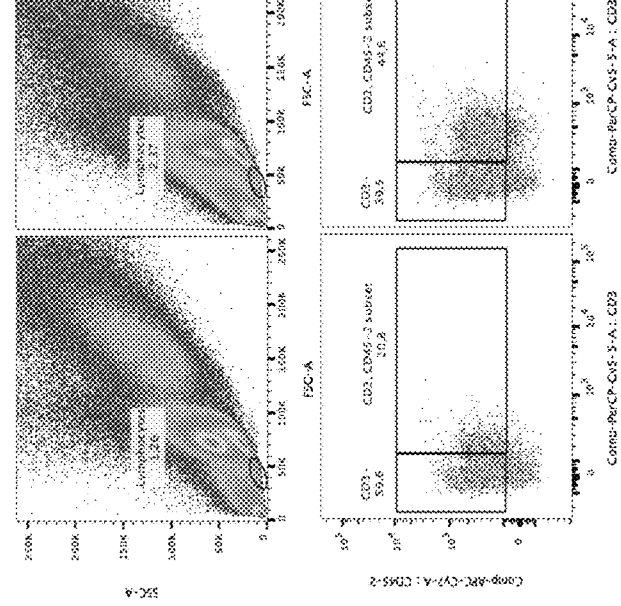
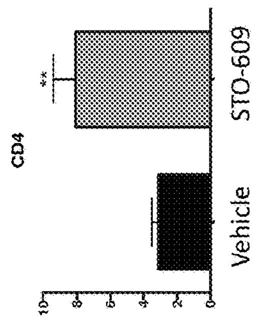

Figure 20A-C

Figure 22B-C
Fig. 22B
Ly6C+
Ly6C+
F480
Lymphocytes
0
$10^3$
$10^4$
$10^5$
Comp-FITC-A :: EGFP-CaMKK2
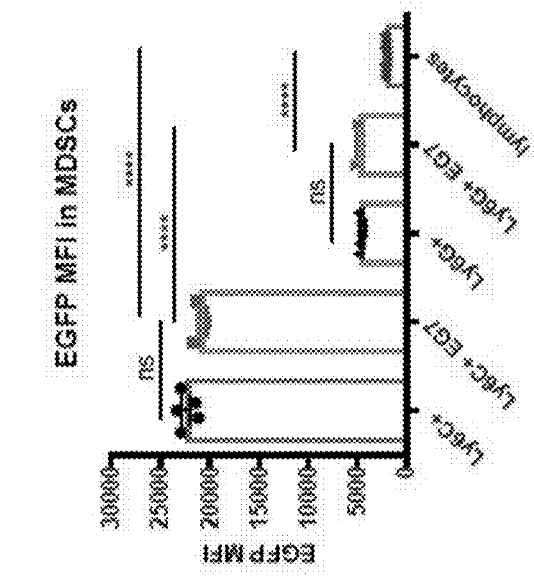
c.
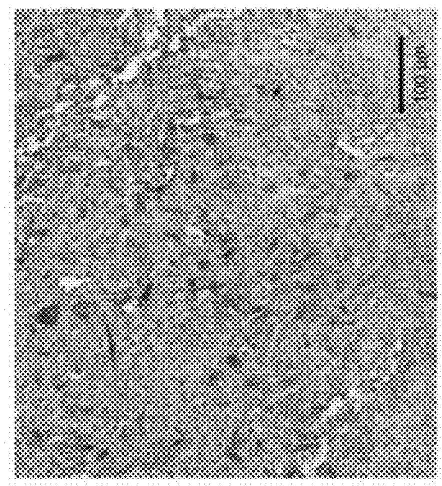
Fig. 22C d.

Figure 23A-C

Photon Counts
Days
WT
KO
P=0.01

Figure 23D-G
Fig. 23D
d.
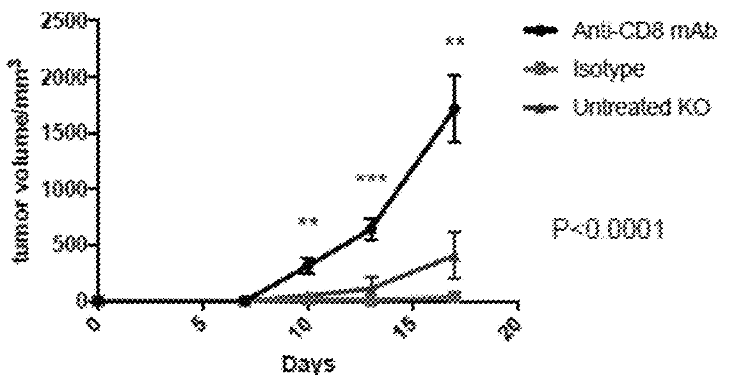
Fig. 23E
e.
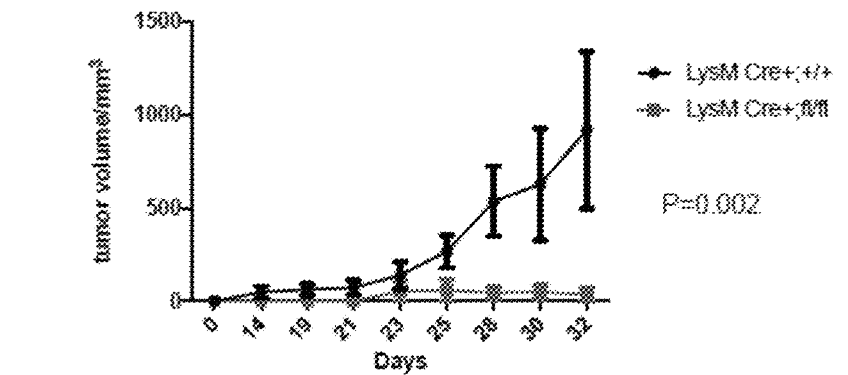
f.
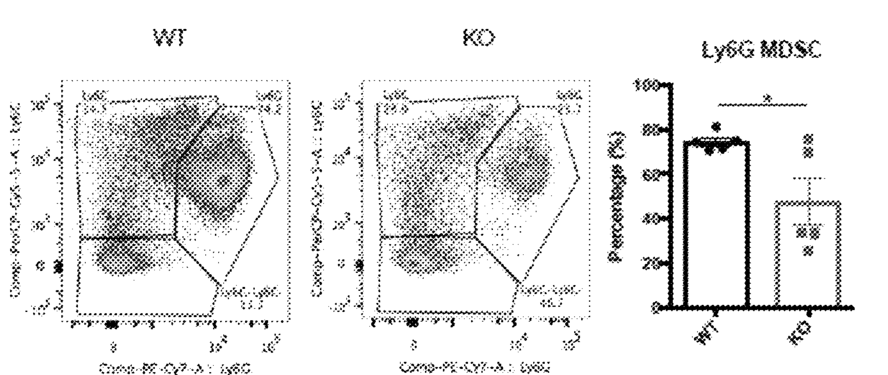
Fig. 23F
g.
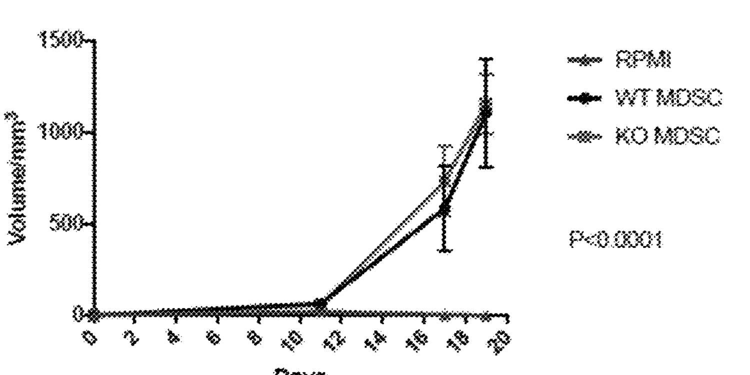
Fig. 23G Figure 24A-E
Fig. 24A
Fig. 24B
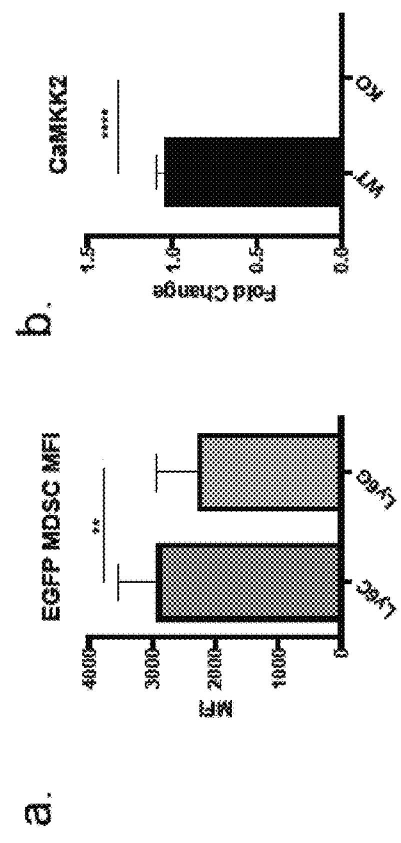
Fig. 24C
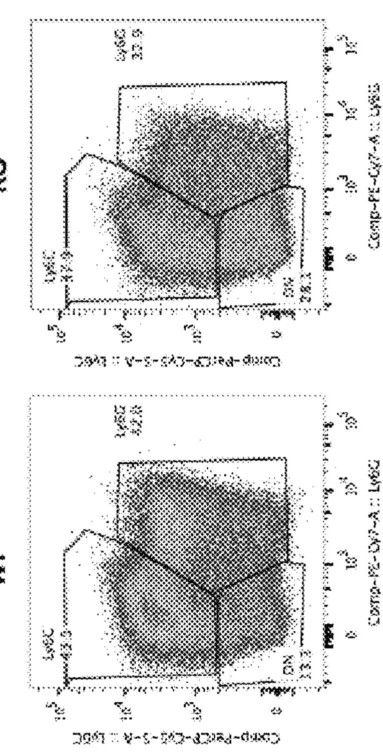
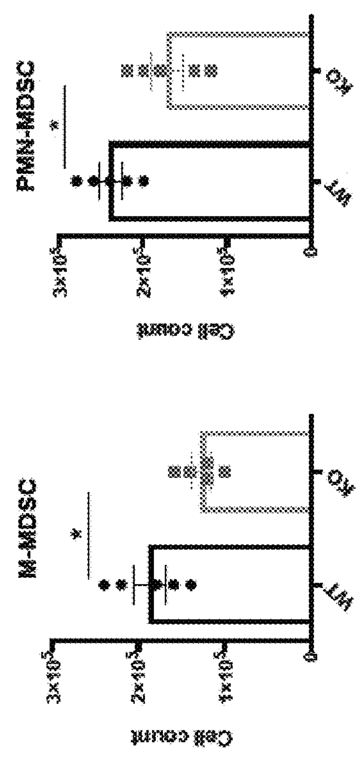
Fig. 24D
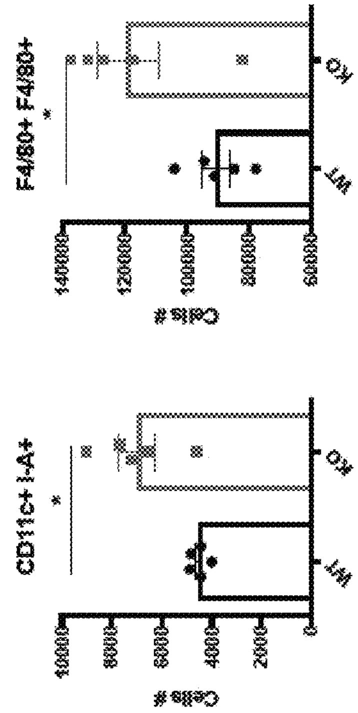
Fig. 24E

Figure 26A-C
Fig. 26A
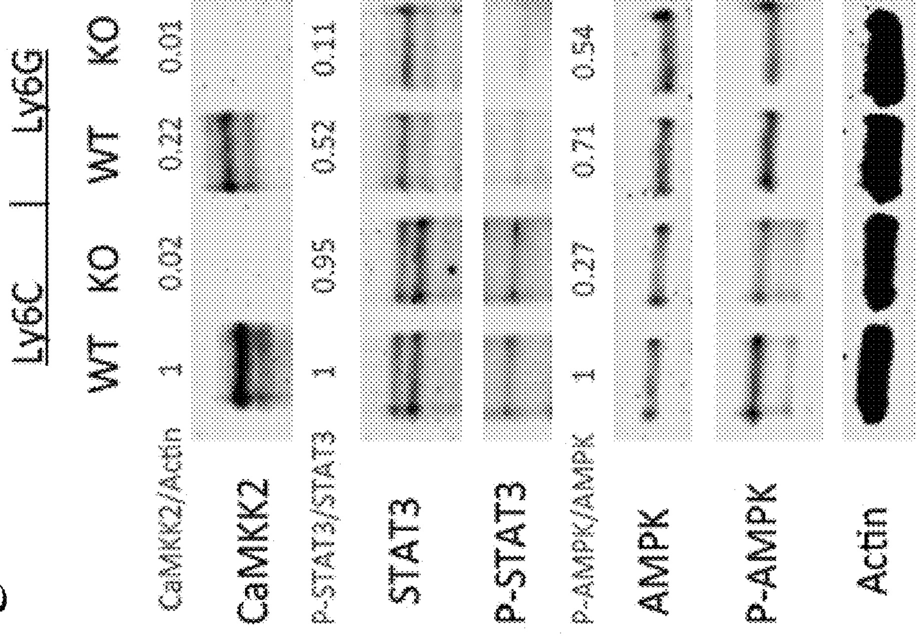
Fig. 26B
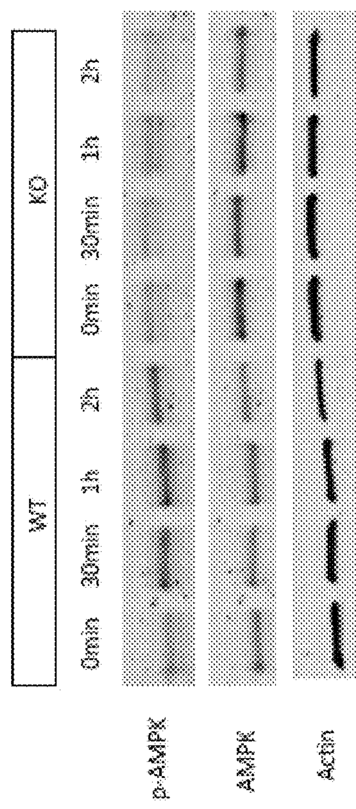
Fig. 26C

Figure 26D-H

Figure 26I-L
ROS (MFI)
WT Ly6C KO Ly6C WT Ly6G KO Ly6G
Fig. 26I
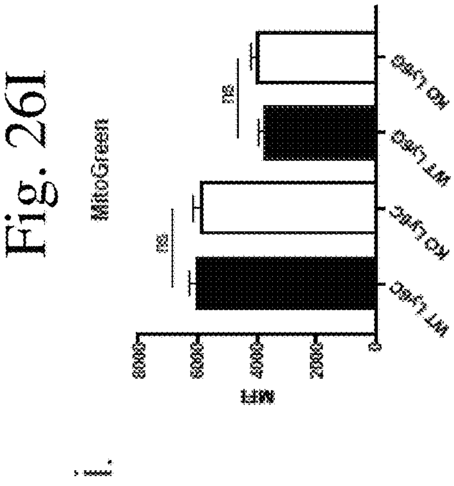
Fig. 26J
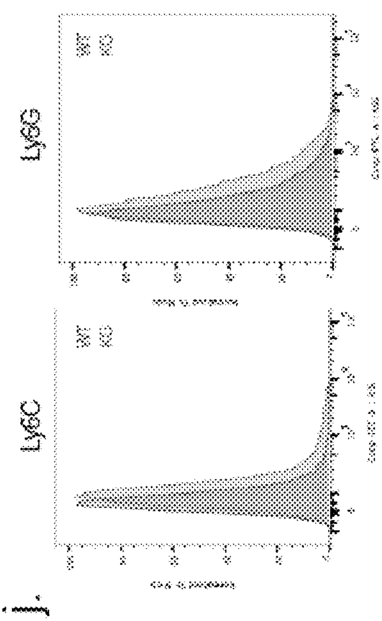
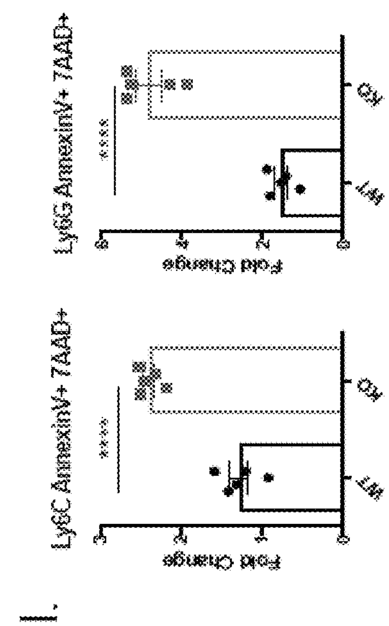
Fig. 26L
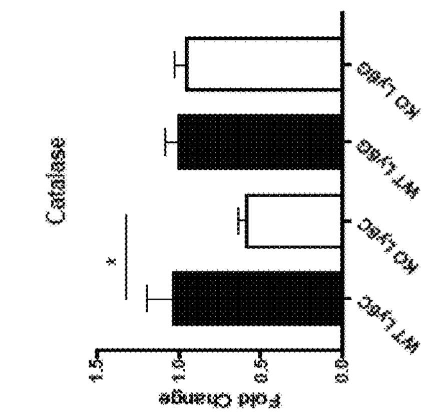
Fig. 26K Figure 27A-B
Fig. 27A
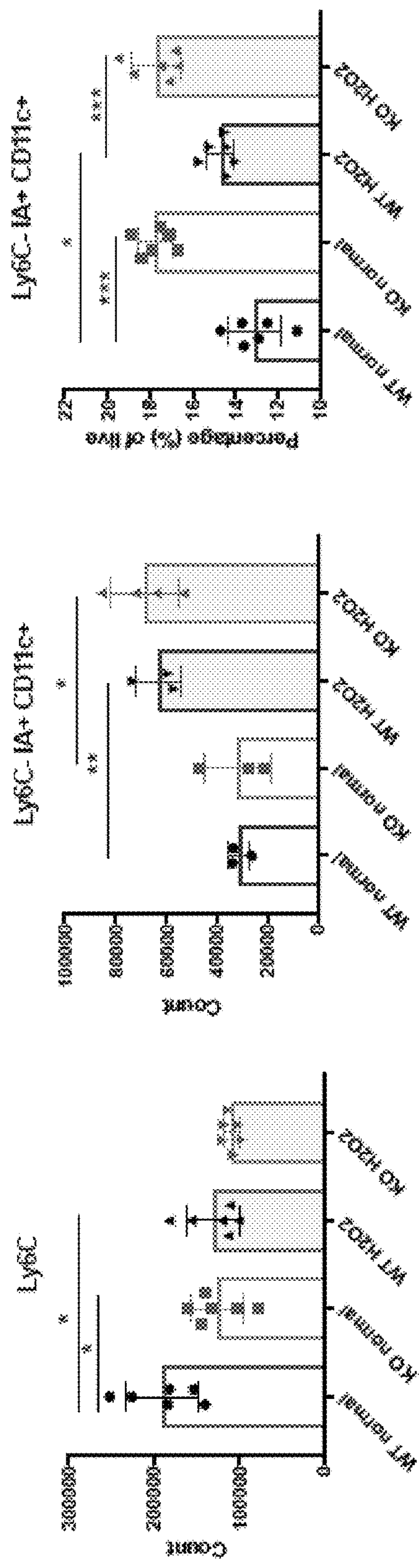
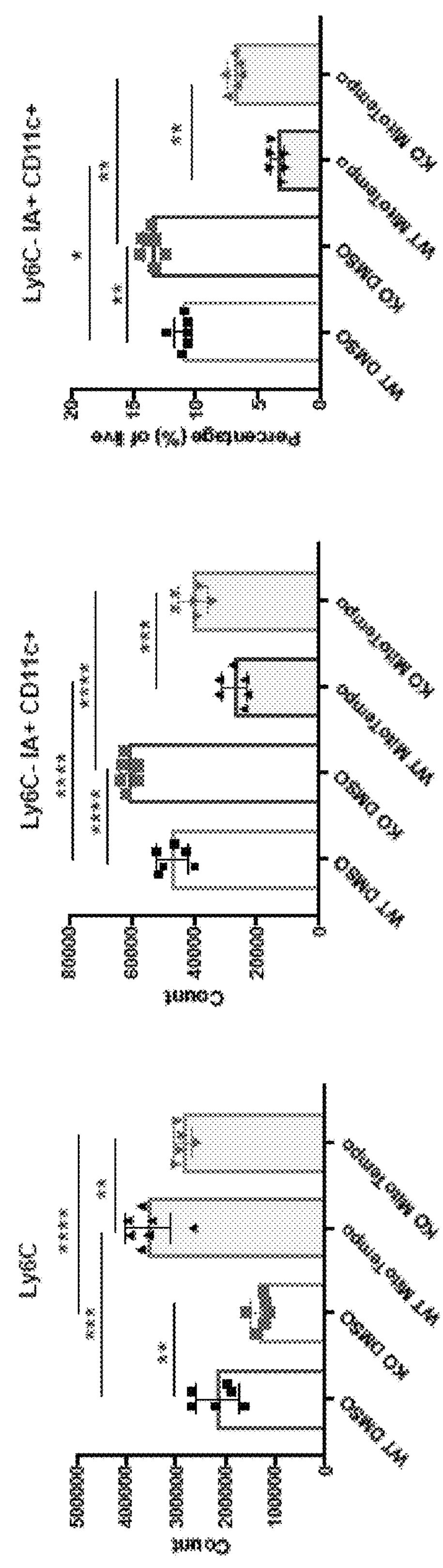
Fig. 27B

C.

Figure 28A-C
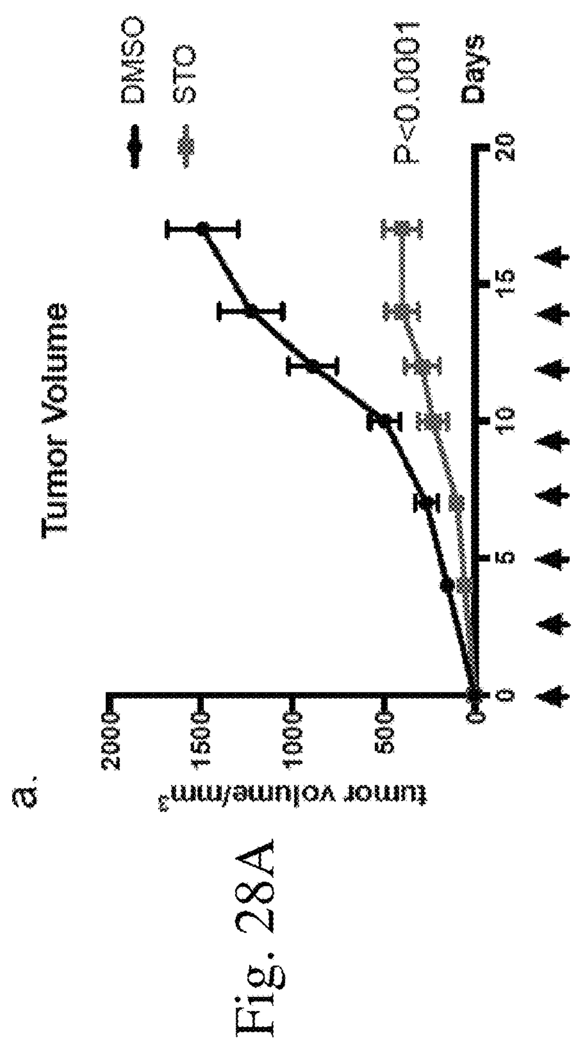
Fig. 28A
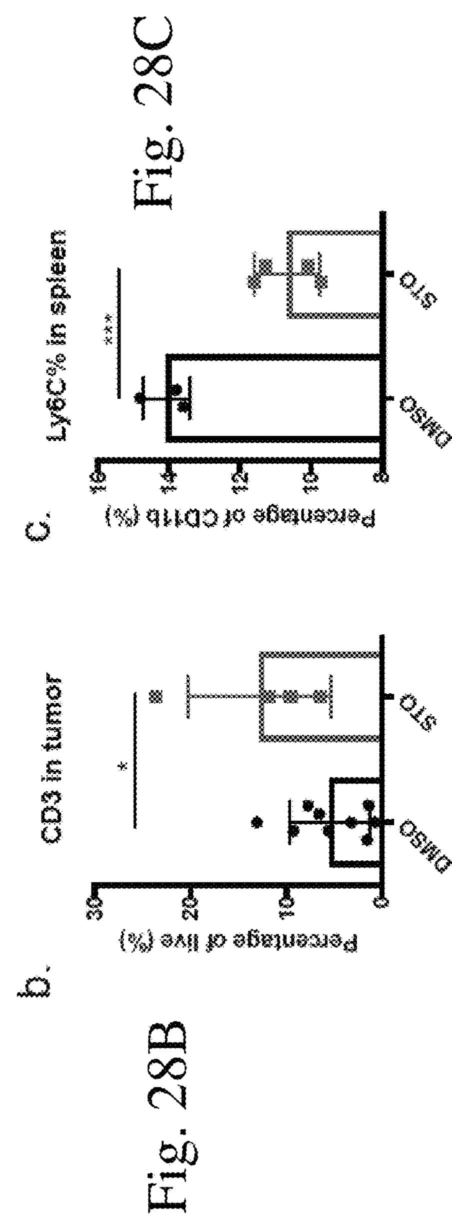
Fig. 28B
Fig. 28C

EG7
-4
-1
0
3
7
10
14
17
Days
Anti-CD8 mAb/Isotype IgG
b.

CD8 depletion
Percentage (%)
20
15
10
5
0
ns
****
***
Isotype
CD8mAb
Before Injection
Before EG7
After EG7

Figure 31A-D
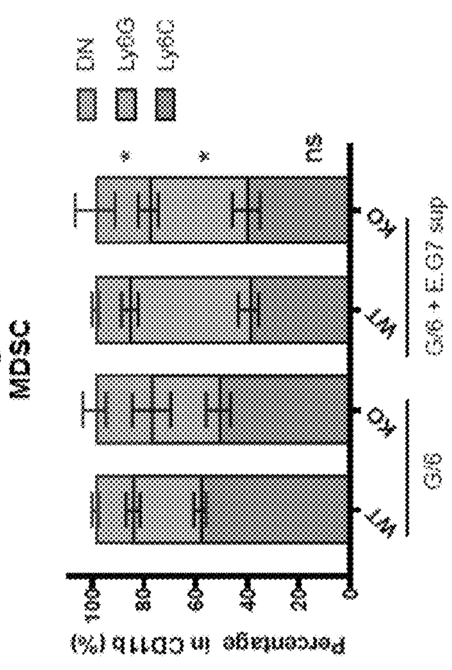
Fig. 31B
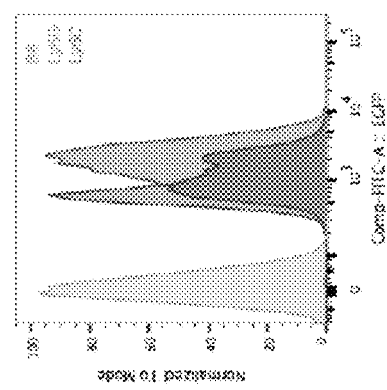
Fig. 31A
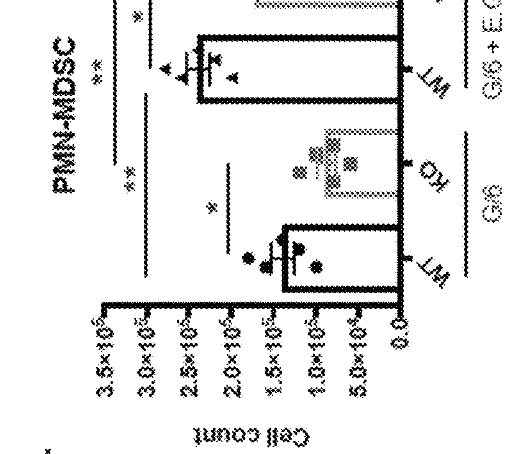
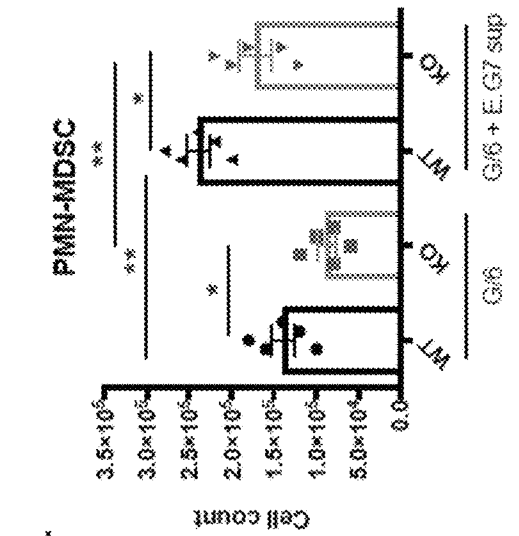
Fig. 31D
Fig. 31C Figure 32A-B
Fig. 32A
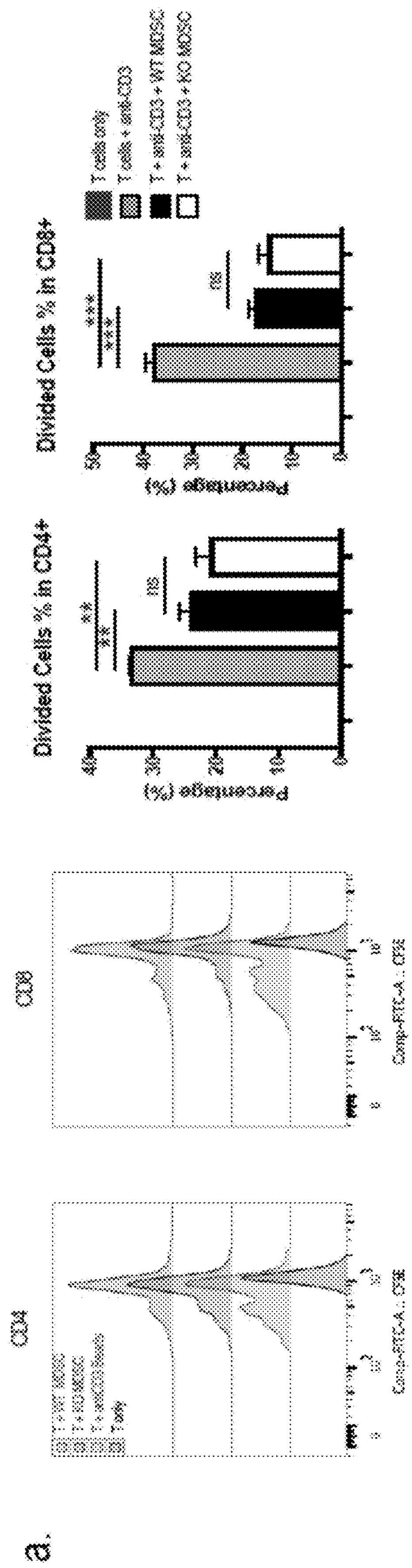
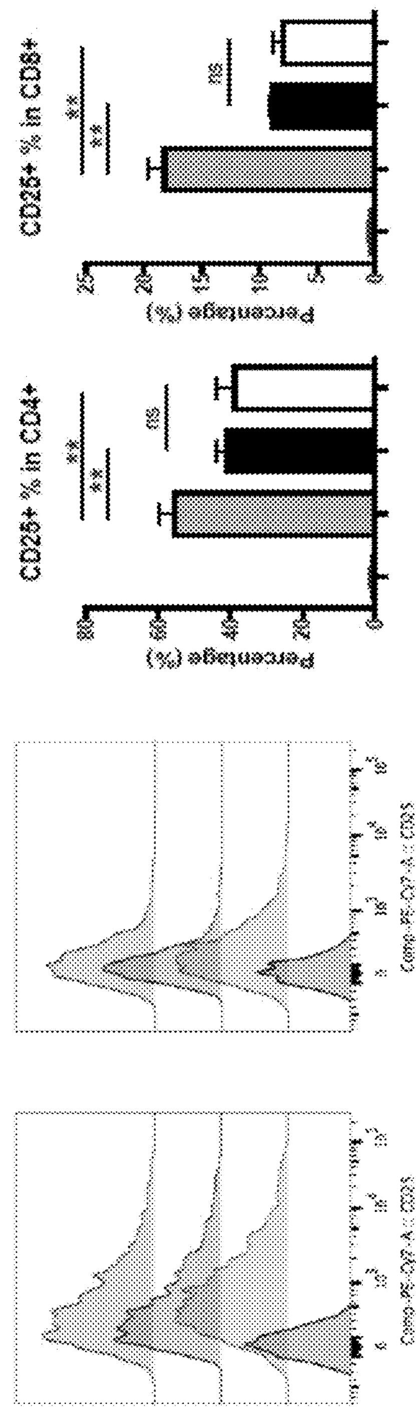
Fig. 32B Figure 32C-E
Fig. 32C
c.
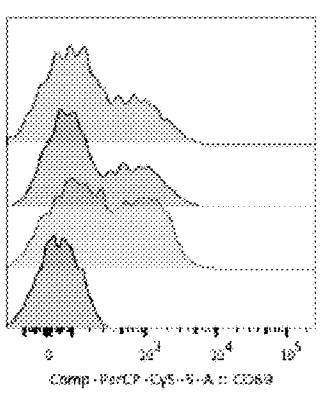
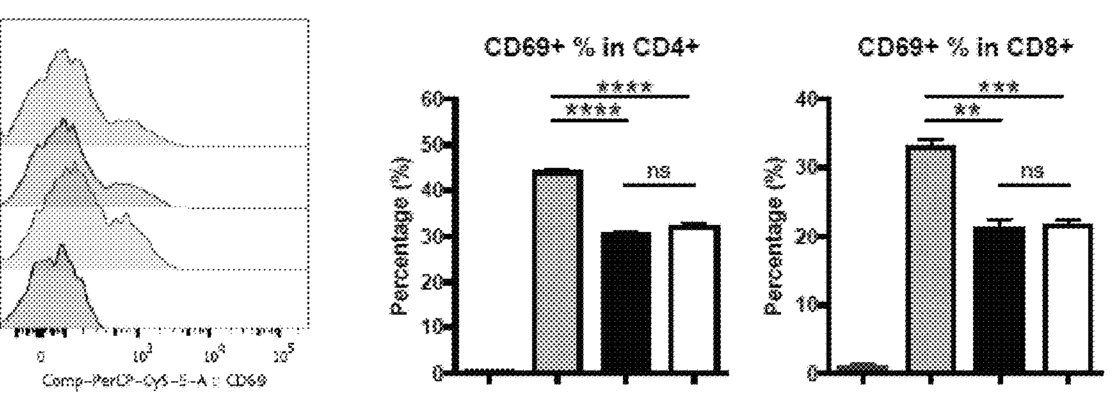
d.
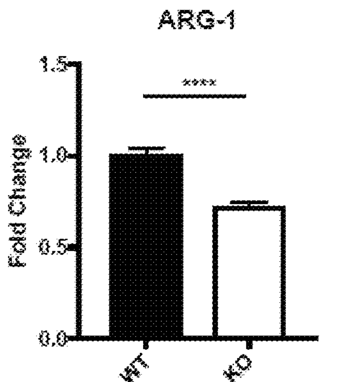
Fig. 32D
e.
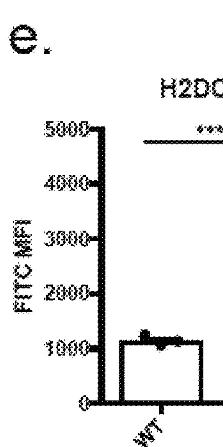
Fig. 32E

Figure 33A-B

Figure 34A-D
a. Fig. 34A
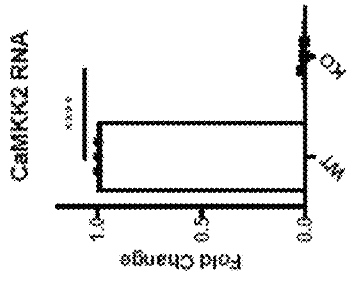
b. Fig. 34B
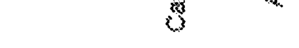
c. Fig. 34C
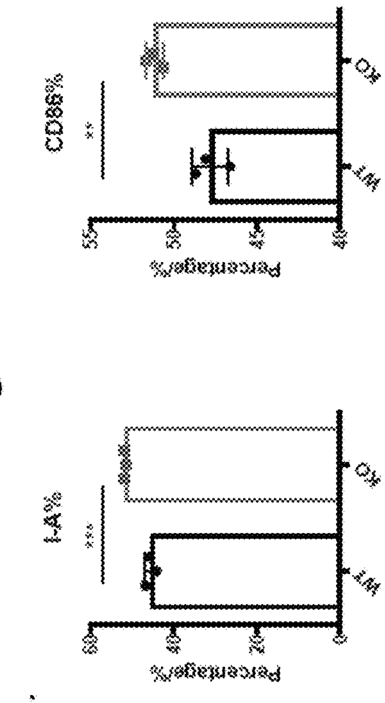
d. Fig. 34D
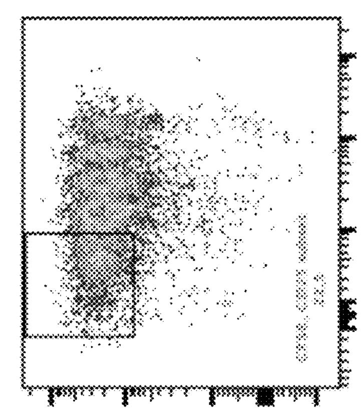
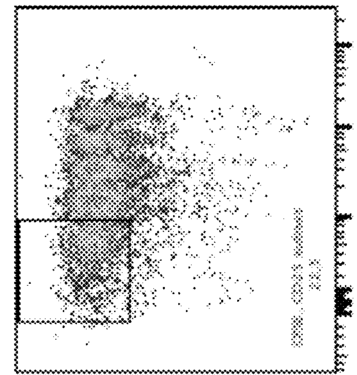
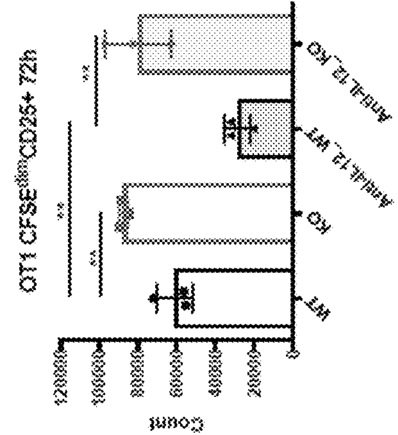

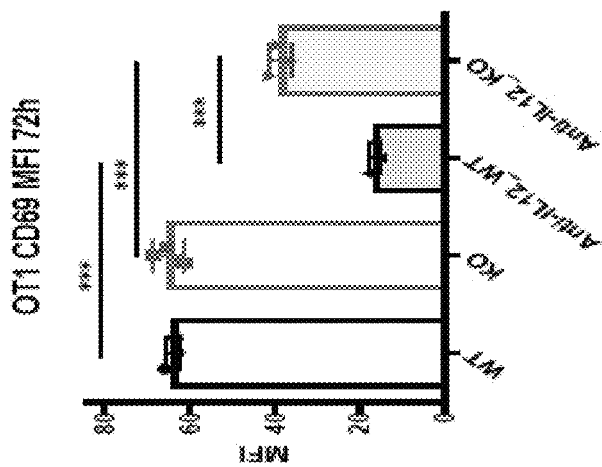
Fig. 34E
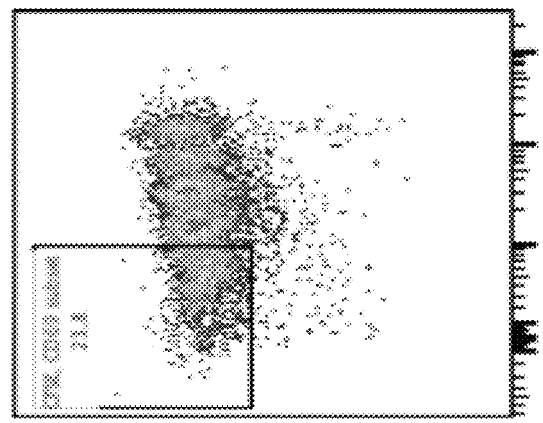
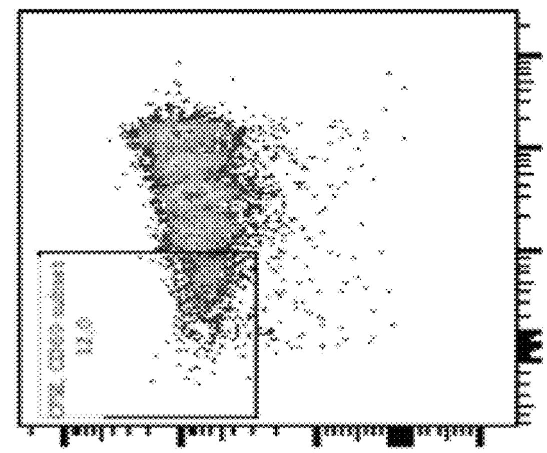
e.

Figure 35
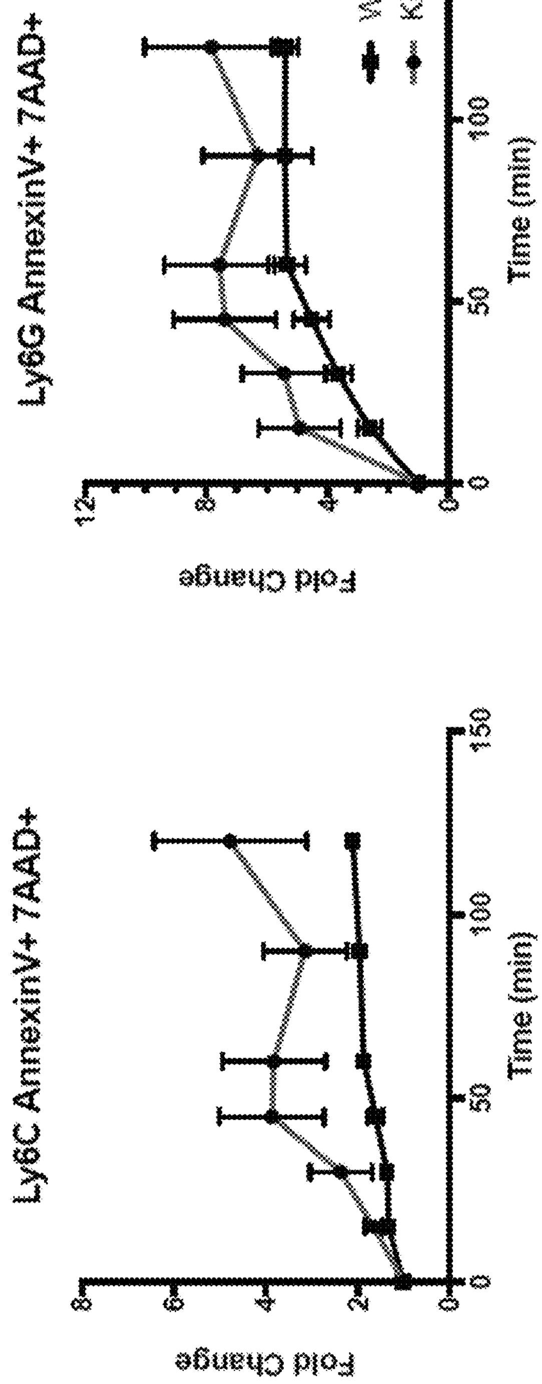
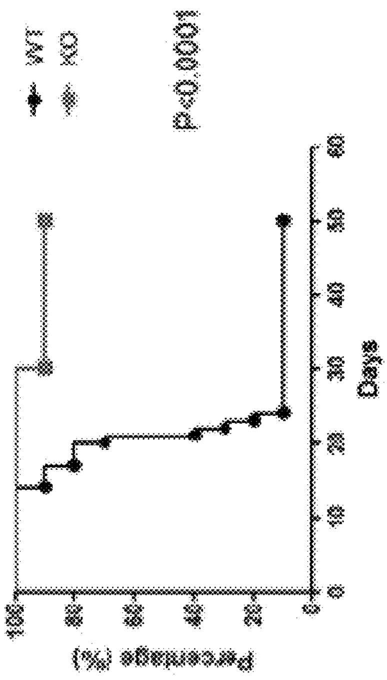
Fig. 36B
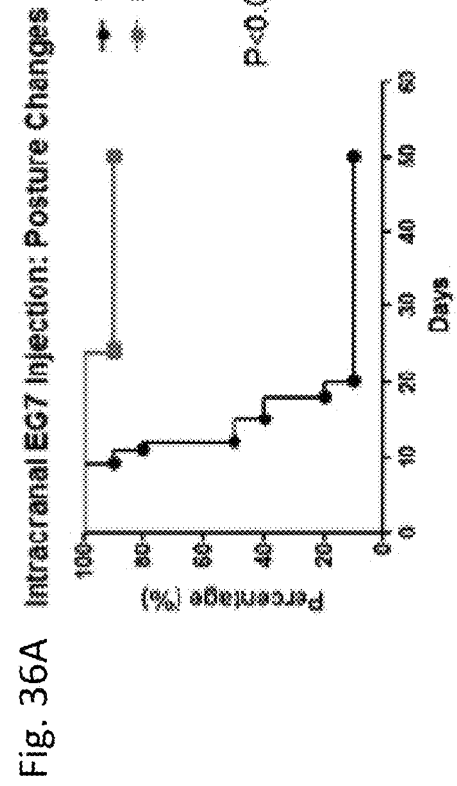
Fig. 36A

Figure 37A-B
Fig. 37A
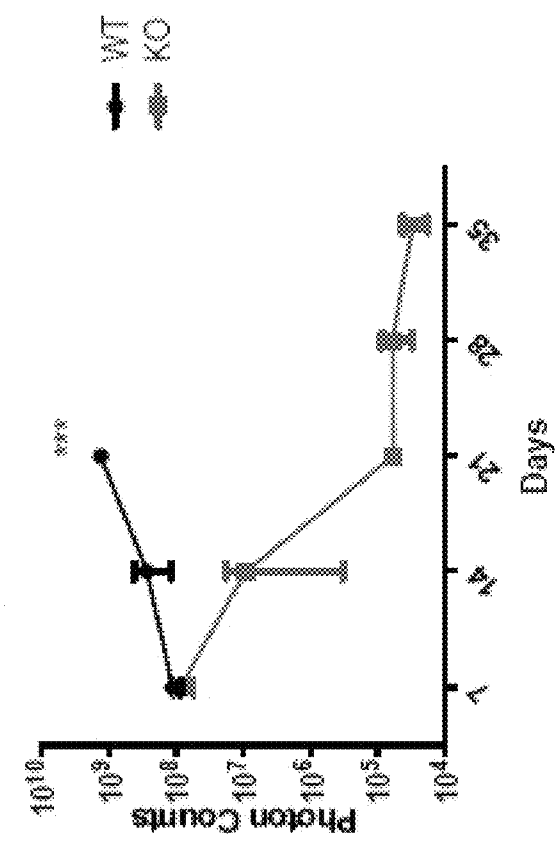
Fig. 37B
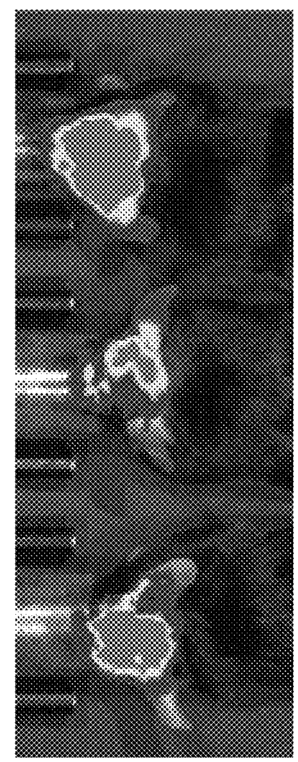
Control Luciferase
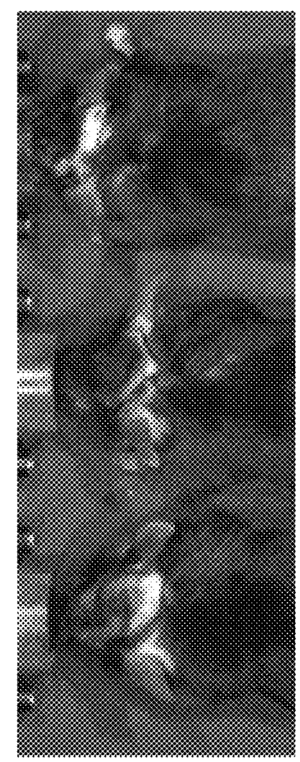
CaMKK2 -/- Luciferase

CaMKK2 INHIBITOR COMPOSITIONS AND METHODS OF USING THE SAME

CROSS-REFERENCE TO RELATED APPLICATIONS

This patent application is a national stage filing under 35 U.S.C. 371 of International Application No. PCT/US2017/045749, filed Aug. 7, 2017, which claims the benefit of priority of U.S. Provisional Patent Application No. 62/371,309, filed Aug. 5, 2016, both of which are incorporated herein by reference in their entirety.

STATEMENT REGARDING FEDERALLY SPONSORED RESEARCH

This invention was made with United States government support awarded by the National Institutes of Health grant number W81XWH-15-1-0443. The United States has certain rights in this invention.

SEQUENCE LISTING

A Sequence Listing accompanies this application and is incorporated herein by reference in its entirety. The Sequence Listing was filed with the application as a text file on Aug. 7, 2017.

INTRODUCTION

The recruitment of innate immune cells, such as macrophages, is an important process in the initial phases of cancer tumor development. In the tumor microenvironment, myeloid cells often differentiate into tumor-associated macrophages (TAMs), which have the ability to promote blood vessel formation and support tumor growth at primary and metastasis sites. TAMs also have the remarkable ability to inhibit effector T-cells and stimulate the accumulation of regulatory T-cells (Treg), thus substantially contributing to the robust immune-suppressive microenvironment found in many types of tumors. Not surprisingly, TAM density in primary tumors is strongly associated with poor outcomes in treating many types of cancers. These findings have driven the search for new anti-cancer therapeutic compositions and methods that can be used to reprogram TAMs and/or inhibit the immune-suppressive microenvironment found in tumors.

SUMMARY

In one aspect, compositions including a Calcium-calmodulin kinase kinase 2 (CaMKK2) inhibitor and an anti-cancer therapeutic agent are provided. Optionally, the compositions may be pharmaceutical compositions that may further include a pharmaceutical carrier, excipient, or diluent.

In another aspect, methods of treating cancer in a subject are provided. The methods may include administering any of the compositions or pharmaceutical compositions described herein to a subject in an amount effective to treat the cancer.

In a further aspect, the methods of treating cancer in a subject provided herein may include obtaining a sample from the subject; measuring the immune cells in the sample; and administering a CaMKK2 inhibitor to the subject. In some embodiments, the subject is administered the CaMKK2 inhibitor if the immune cell measurement in the sample is indicative of a poor prognosis or a likelihood of therapeutic resistance to an anti-cancer therapeutic agent.

In a still further aspect, the methods of treating cancer in a subject provided herein include administering to the subject a therapeutically effective amount of a CaMKK2 inhibitor, and administering to the subject a therapeutically effective amount of an anti-cancer therapeutic agent to the subject.

In yet another aspect, kits are also provided. The kits may include a CaMKK2 inhibitor and an anti-cancer therapeutic agent. The kits may also include the components required to perform any of the methods disclosed herein.

BRIEF DESCRIPTION OF THE DRAWINGS

FIG. 2 shows the growth of mammary tumors is attenuated in mice lacking CaMKK2.

FIG. 3 shows the histology of E0771 tumors in wildtype and Camkk2$^{-/-}$ mice. FIG. 3A shows murine E0771 cells ($4\times10^5$ cells/mouse) that were orthotopically grafted in WT and Camkk2$^{-/-}$ mice, and subsequently tumor volume measured as indicated (mean+/−SEM; N=5 in each group). Representative image of.

FIG. 4A shows percentage of GranzymeB+ (GZMB+) cells in CD3+ CD8+ T-cell subset. FIG. 4B shows percentage of MHC II I-A$^{high}$ cells in CD11b+ myeloid subsets. Bar graphs report the mean+/−SEM; N=17 in each group. Bar graphs report the mean+/−SEM; N=6 in each group.

FIG. 5A-C shows the gating strategy used to identify tumor-infiltrating lymphocytes in E0771 mammary tumors from WT and Camkk2$^{-/-}$ mice. FIG. 5A: Single cell suspensions from tumors were stained for T cell markers. Dead cells were identified using a pacific-blue emitting fixable dye (gate a, left). To exclude doublets Pacific-blue negative live cells were sub-gated (gate b, right panel). Cells included in gate b were further sub-gated according to CD3 expression (gate c, lower left). Gate d includes CD8$^{+}$ cells (right lower panel). FIG. 5B: Dot plots report the gating strategy used to identify GranzymeB$^{+}$ and PD-1$^{+}$ CD8$^{+}$ T cell subsets from gate d in FIG. 5A. FIG. 5C: Increased cellular volume of CD8$^{+}$ T cells infiltrating tumors of Camkk2$^{-/-}$ mice. Representative FSC-A histogram (left). Graph reports mean±SEM of FSC-A$^{high}$ percentage in CD8$^{+}$ CD3$^{+}$ T cells (gate d from FIG. 5A).

FIG. 6. Tumor-associated myeloid cell subsets in E0771 tumors from WT and Camkk2$^{-/-}$ mice. E0771 cells were inoculated into the mammary fat pad of WT and Camkk2$^{-/-}$ mice. Subsequently, tumors were removed, digested with collagenase and DNAase. In FIG. 6A single cell suspensions were stained for CD11b, Ly6G, Ly6C, I-A and F4/80. FIG. 6A Upper panels show the gating strategy used to identify tumor-associated myeloid cell subsets (I and II). FIG. 6A Lower panels show sub-gating strategy to identify M, G and DN mammary tumor-associated myeloid cell subsets.

FIG. 7B reports the mean±SEM of CD8$^{+}$ cells (as a percentage) in mouse peripheral blood collected before and 7-days after E0771 cell engraftment (day 0 and 7, respectively). Asterisks refer to *p<0.05, p<0.01, *p<0.005 and ****p<0.001, respectively.

FIG. 9A: Representative CaMKK2 immunoblot of protein lysates from macrophages isolated by peritoneal lavage of LysM-Cre$^{+}$ Camkk2$^{wt/wt}$ and LysM-Cre$^{+}$ Camkk2$^{fl/fl}$ mice (N=3 each group). Bone marrow derived macrophages (BMDM) from WT and germline Camkk2$^{-/-}$ mice were used as positive and negative controls for CaMKK2 expression (lane 1 and 2, respectively). FIG. 9B: Quantitation of immunoblot. FIG. 9C: E0771 cells were orthotopically grafted into LysMCre$^{-}$ Camkk2$^{fl/wfl}$ and LysMCre$^{+}$ Camkk2$^{fl/fl}$ mice. Tumor volume was measured (mean±SEM; N=5 for each group). Asterisks refer to *p<0.05, p<0.01, *p<0.005 and ****p<0.001, respectively.

FIG. 10 shows cytokines in E0771-conditioned medium. FIG. 10A shows representative concentrations of cytokines detected in regular medium or in cultures supernatants of E0771cells. FIG. 10B is a pie chart reporting the fraction of cytokines in E0771-conditioned supernatants. FIG. 10C shows the experimental scheme to determine the effects of E0771-conditioned medium on WT and Camkk2$^{-/-}$ bone marrow-derived macrophage development.

FIG. 11 shows CaMKK2 signaling controls the responsiveness of macrophages to tumor-derived soluble factors. BMDM were generated from WT and Camkk2$^{-/-}$ mice in the presence or absence of E0771-conditioned medium. Subsequently, BMDM were analyzed for genes and protein expression.

FIG. 12 shows the gene expression in WT and Camkk2−/− BMDM generated in the presence or absence of tumor-conditioned medium.

FIG. 13 shows the evaluation of potential downstream targets of CaMKK2 in macrophages. FIG. 13**G shows deletion of ERRα was confirmed by immunoblotting on bone marrow-derived macrophage (BMDM) isolated from ERRα$^{f/f}$ and LysM Cre$^{+}$ ERRα$^{fl/fl}$ mice.

FIG. 14A shows the gating strategy used to identify live, singlet, F4/80$^{+}$ cells in 5-day cultures of macrophages generated from WT or Camkk2$^{-/-}$ bone marrow cells. FIG. 14B shows representative FACS profiles of WT or Camkk2$^{-/-}$ macrophages generated in the presence of regular or E0771-conditioned medium (light and dark profiles, respectively).

FIG. 15 shows the phenotype and immune-stimulatory capability of WT and Camkk2−/− BMDM generated in the presence or absence of tumor-conditioned medium. FIG.

15A shows expression of MHCII I-A, CD86 and CD40 evaluated by flow cytometry. Bar graphs show mean±SEM (N=8 groups). FIG. 15B measures cytokines (IL-2, IFN-g and CXCL-10, respectively) in cell supernatants following 24 h co-cultures. FIG. 15C shows FACS profiles of T cells recovered after co-culture for 72 h. FIG. 15D is a bar graph reporting the percentage of CSFE-low $CD8^+$ T cells. N=3 for each genotype. The experiment was replicated with similar results. Asterisks refer to *p<0.05, p<0.01, *p<0.005 and ****p<0.001, respectively.

FIG. 17 shows treatment with a CaMKK2 inhibitor attenuates the growth of mammary tumors in immunocompetent mice.

FIG. 18 shows small molecule inhibitors of CaMKK2 inhibit breast cancer tumor growth, FIGS. 18A-B shows results when mammary tumor cells ($4\times10^5$/mouse) were orthotopically grafted into syngeneic wildtype mice, that were treated 3-times/week with vehicle or STO-609 (IP, 100 moles/Kg body weight), and subsequently tumor volume measured (mean+/−SEM; N=5 in each group). FIGS. 18A-B show 4T1 and Met1mammary tumor growth, respectively, are inhibited by STO-609 treatment. FIG. 18C shows E0771 mammary tumor growth is inhibited by GSKi, a CaMKK2 inhibitor. FIG. 18D shows a two-step in vitro CaMKK2 kinase assay. Top: structures of the CaMKK2 inhibitors STO-609 and GSKi. (Bottom) Purified recombinant purified GST-CaMKK2 (4 nM) was incubated with MBP-$AMPK\alpha2^{1-312}$ (200 nM) and SAMS peptide (20 mM) in the presence of [$\gamma^{32}P$]-ATP±CaMKK2 inhibitors or $\pm Ca^{2+}$/CaM as described by Green et al.[1]. Incorporation of labeled $^{32}P$ on SAMS peptide was measured by scintillation counting as a readout of CaMKK2 and/or AMPKα2 phosphorylation. Reaction controls for no CaMKK2, no AMPK or no SAMS peptide were included to determine background and signal specificity.

FIG. 19 shows a gating strategy to identify T-cells in E0771 mammary tumor in mice treated with STO-609 or vehicle. E0771 mammary tumors were removed from mice STO-609 or vehicle-treated mice. FIG. 19A shows results when tumors were dissociated as described previously and single cell suspension stained for myeloid or T-cell markers and analyzed by FACS. Lymphocytes were identified according to FSC-A and SSC-A (upper panels). T-cells were identified on lymphocyte gate using CD45.2 and CD3 staining (lower panels). FIG. 19B shows FACS analysis of CD8+ and CD4+ T-cells identified on T-cell gate (upper panels). CD4− CD8− T-cells expressing NK1.1 marker were identified as NK-T cells (lower left). NK cells were gated as CD45+ CD3− NK1.1+ cells (lower right). FIG. 19C is a set of graphs showing mean and SEM of CD4, NK-T and NK cells percentage in tumors from mice treated with STO-609 or vehicle (N=5 for each group). Asterisks refer to p<0.05, 0.01, 0.005 and 0.001 (*, , * and ****, respectively).

(FIG. 20A, Left) Negative staining breast cancer; (FIG. 20A, Right) Positive staining of tumor and stromal cells (high magnification, 400×).

FIG. 22 shows CaMKK2 promoter is active in myeloid derived suppressor cells (MDSC). FIG. 22B shows the CaMKK2-EGFP reporter activity in MDSC cells in the spleens of mice with or without E.G7 tumor. M-MDSC had higher CaMKK2 reporter activity compared to PMN-MDSC. n=5. FIG. 22C shows anti-EGFP immunohistology staining on E.G7 tumor from CaMKK2-EGFP reporter mice. 20×.

FIG. 24 shows CaMKK2 regulates MDSC generation in vitro. (FIG. 24A) Flow cytometry analysis showing that CaMKK2-EGFP reporter was on in both in vitro generated M-MDSC and PMN-MDSC in the presence of E.G7 supernatant. M-MDSC had higher reporter activity compared to PMN-MDSC. n=5. p<0.01. (FIG. 24B) Realtime PCR of CaMKK2 in in vitro generated MDSC. n=11. Combined from two experiments. (FIG. 24C) A representative flow cytometry plot to show MDSCs generated from WT and KO bone marrow in vitro with E.G7 supernatant. (FIG. 24D) Quantification of MDSCs generated in vitro from the marrow of WT and KO mice with E.G7 tumor supernatant. n=5. (FIG. 24E) Cell counts of CD11c+I-A+ cells and I-A+F4/80+ cells in Ly6C−Ly6G− compartment from in vitro generated MDSC. n=5. (FIG. 24F) showed MDSC gating. (FIG. 24G) showed with dendritic cell gating of M-MDSC culture. n=2.

FIG. 25 shows CaMKK2 regulates dendritic cell development and function in vitro.

FIG. 26 shows AMPK pathway is the downstream target of CaMKK2 in regulating myeloid cells differentiation through mitochondrial metabolism. (FIG. 26A) Western blot of in vitro generated MDSC. Cells pooled from 5 mice. (FIG. 26B) Western blot for in vitro generated MDSC stimulated with IL-6 for different timespan after cytokine deprivation for 12 h. Cells pooled from 5 mice. (FIGS. 26C-26G) Mitochondrial respiration of WT and KO MDSC measured by Seahorse XF mitostress test (n=6) combined from two individual experiments. (FIG. 26I) Flow cytometry quantification (MFI) of mitochondrial mass using MitoGreen dye in WT and KO MDSC. n=5. (FIG. 26J) Representative plots and quantification of ROS in MDSC detected by flow cytometry with H2DCFDA dye. n=5. (FIG. 26K) Realtime PCR of catalase in WT and KO MDSC. n=6. Combined from two experiments. (FIG. 26L) Fold change of apoptotic cells detected by flow cytometry after exposing MDSC to 200 μM $H_2O_2$ for 60 min. n=5. Experiments repeated once. * p<0.05.  p<0.01. * p<0.001.

FIG. 27 shows ROS regulates M-MDSC accumulation and differentiation in vitro. (FIG. 27A) MDSC in vitro generated with 0.001 mM H2O2 added. (FIG. 27B) MDSC in vitro generated with 20 μM MitoTEMPO added.

FIG. 28 shows STO609 impairs E.G7 tumor growth in mice and regulates lymphoma tumor microenvironment. (FIG. 28A) C57BL/6 mice were inoculated with E.G7 5×105 cells 10 days before treatment. Tumor implantation was confirmed by bioluminescent imaging. Mice were injected with DMSO (n=9) or STO-609 (n=6) every 2-3 days as the arrows indicated. (FIG. 28B) Quantitation of percentage of CD3 cells in tumors from mice receiving DMSO (n=9) or STO-609 (n=4). (FIG. 28C) Quantitation of percentage of Ly6C+ cells in CD11b+ population in the spleens of DMSO (n=3) or STO-609 (n=4) treated mice. Experiments repeated once.

FIG. 29 shows tumor growth in WT and KO mice.

FIG. 30 shows CD8 depletion in vivo.

FIG. 31 shows CaMKK2 regulates MDSC generation in vitro. (FIG. 31A) A representative flow cytometry plot of MDSC generated from CaMKK2-EGFP reporter mice in vitro. (FIG. 31B) Percentage of Ly6C, Ly6G, and double negative cells (DN) in CD11b+ population in in vitro generated MDSC with or without E.G7 supernatant. (FIGS. 31C and 31D) Quantification of in vitro generated MDSC from WT and KO bone marrow with or without E.G7 supernatant. n=5. Experiments repeated three times. *p<0.05. p<0.01. *p<0.001.

FIG. 32 shows CaMKK2 regulates MDSC function in vitro. (FIGS. 32A-C) Representative flow cytometry plots and quantification of in vitro generated MDSC co-cultured with CFSE-stained T cells in the presence of anti-CD3 mAb for 72 h. Detected by flow cytometry. n=3. (FIG. 32A) Percentage of CFSE labeled divided cells in CD4 and CD8. (FIG. 32B) Percentage of CD25+ cells in CD4 and CD8. (FIG. 32C) Percentage of CD69+ cells in CD4 and CD8. Experiments repeated twice. n=3. (FIG. 32D) Quantitative PCR detecting Arginase-I expression in in vitro generated WT and KO MDSC. n=17 Pooled from three experiments. (FIG. 32E) ROS in vitro generated MDSC detected by flow cytometry. n=3. Experiments repeated twice. *p<0.05. p<0.01. *p<0.001.

Figures 33A, 33B:
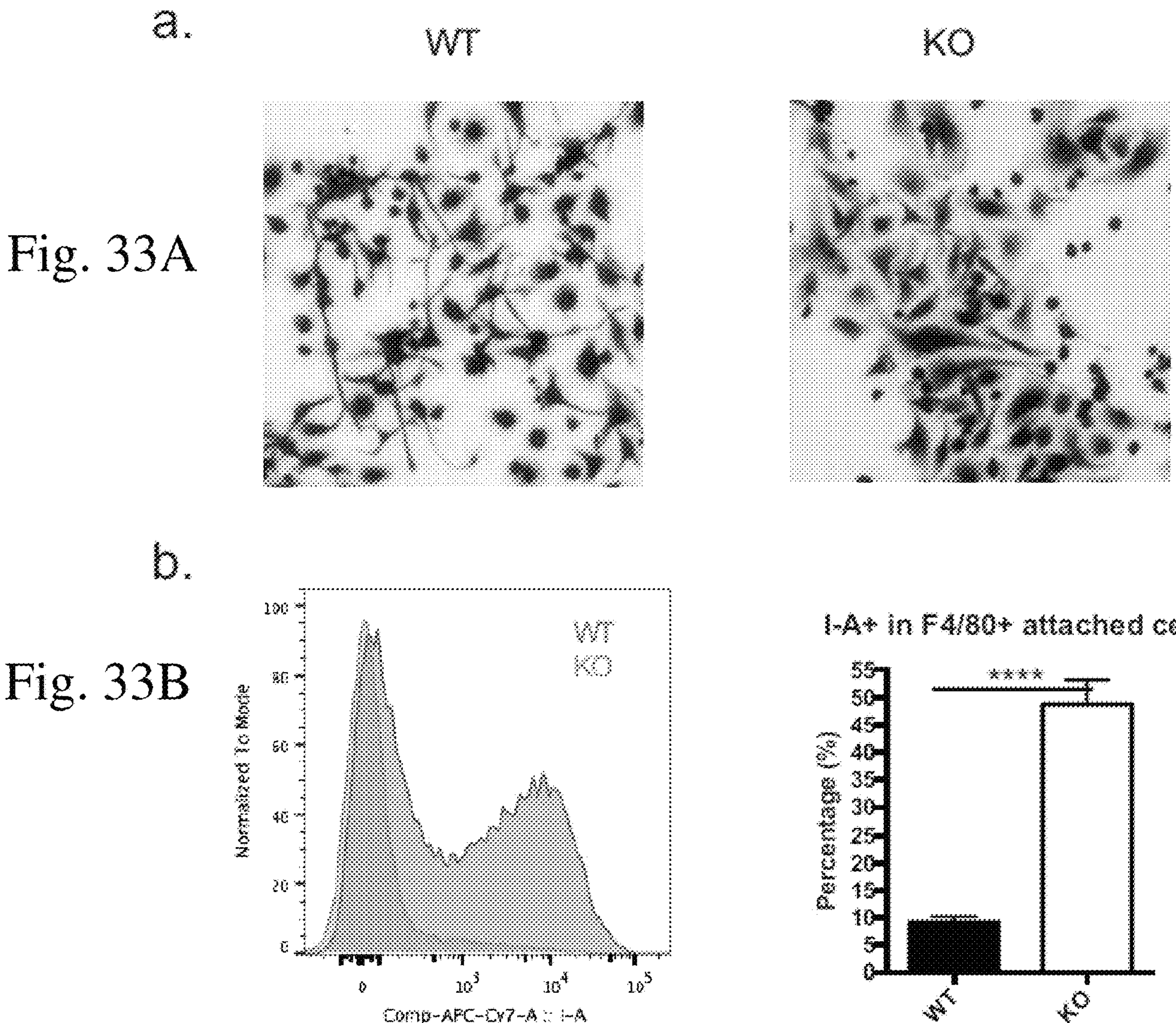
Figure 33C:
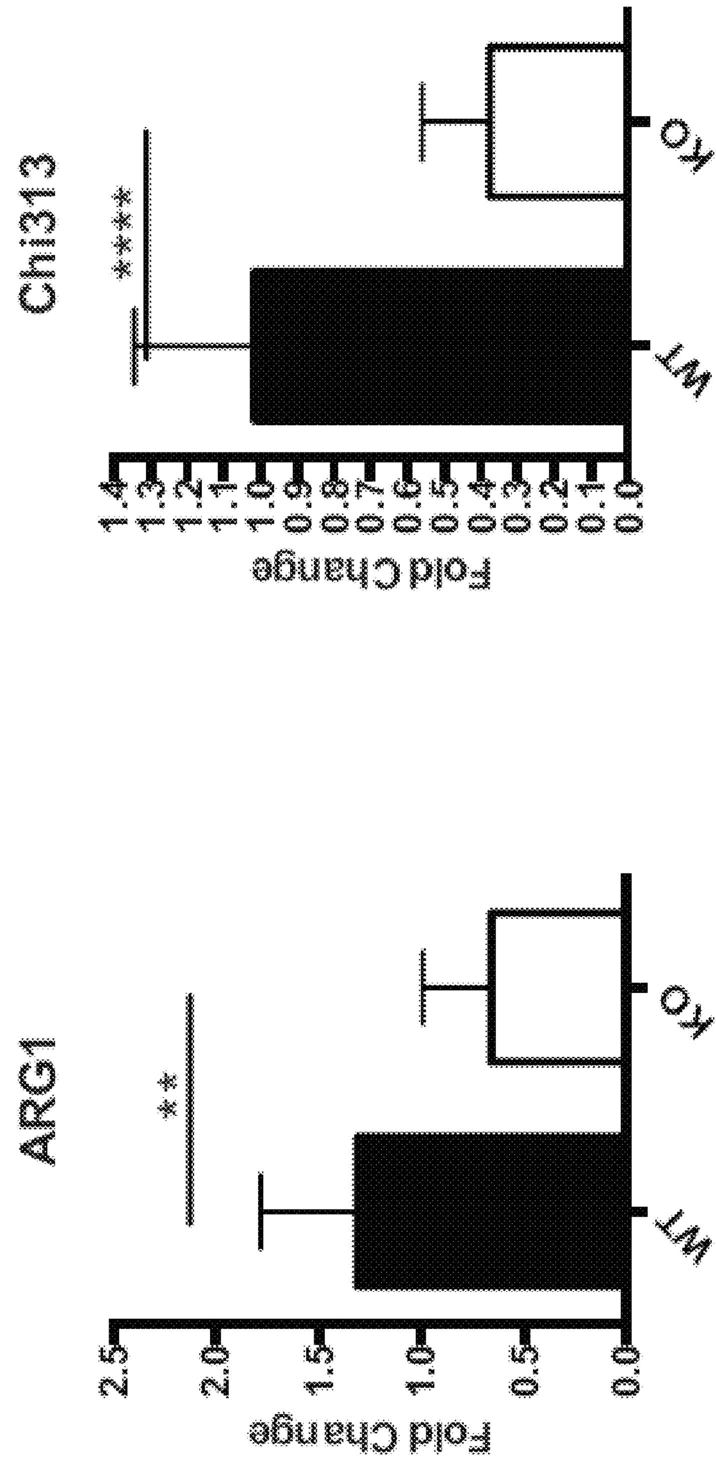

FIG. 33 shows CaMKK2 regulates macrophage cell development in vitro. (FIG. 33A) Crystal violet staining of attached cells from the wells of WT (left) and KO (right) MDSC in vitro culture. (FIG. 33B) Representative plot and quantification of I-A staining in the CD11b+Ly6C−Ly6G−F4/80+ populations of the attached cells. n=5. Repeated three times. (FIG. 33C) Realtime PCR of Arginase-1 and Chi313 in attached cells. n=11. Combined from three independent experiments. *p<0.05. p<0.01. *p<0.001.

FIG. 34 shows CaMKK2 regulates dendritic cell development and function in vitro and in vivo. (FIG. 34A) Realtime PCR and (FIG. 34B) Western Blot to confirm CaMKK2 expression in WT BMDCs but not in KO BMDCs. CaMKK2 RNA level is 10-fold higher in WT BMDCs compared to KO cells. n=3. (FIG. 34C) Splenic DCs in normal KO mice had higher percentage of I-A+ (p<0.001) and CD86+ (p<0.01) in CD11b+CD11c population. (FIGS. 34D & 34E) Splenic DCs separated from tumor bearing WT and KO mice co-cultured with CFSE-labeled primed OT1 T cells for 72 h, with or without anti-IL12 mAb. Stimulated with OVA 257-264 peptide. n=3. (FIG. 34D) Representative plots and quantification of CD25+CFSEdim OT1 cells. (FIG. 34E) Representative plots and quantification of CD69+ CFSEdim OT1 cells. Experiments repeated once. *p<0.05. p<0.01. *p<0.001.

FIG. 35 shows KO MDSC were more sensitive to $H_2O_2$ stimulation in vitro generated MDSC were challenged with 200 μM $H_2O_2$. Cells were collected and detected for apoptosis every 15 min by flow cytometry. n=3. Repeated twice.

FIG. 36 shows a set of graphs showing the number of mice with posture changes (FIG. 36A) and a survival curve (FIG. 36B) in CaMKK2 knock-out mice as compared to wild-type mice after intracranial injection with E.G7. WT and CaMKK2$^{-/-}$ mice (n=10) with $1\times10^4$ E.G7 cells intracranial injection were monitored every other day. FIG. 36A shows the graph to show mice with posture changes. Most WT mice show abnormal posture from day 10-20 after injection. FIG. 36B is a graph showing a survival curve. Mice were sacrificed when moribund. Data was pooled from two individual experiments. Log-rank (Mantel-Cox) Test was used for analysis. P<0.0001.

FIG. 37 is a set of figures showing bioluminescent imaging of mice after E.G7 intracranial injection. WT and CaMKK2$^{-/-}$ mice (n=10) were injected with $1\times10^4$ E.G7 cells i.e. and monitored by bioluminescent imaging every week. FIG. 37A is a graph showing the photon count in wild-type and CAMKK2−/− mice and the counts were calculated by imaging software. The difference in photon count between two groups was significant on Day 21. P<0.001. FIG. 37B shows bioluminescent image of mice on Day 21. FIG. 37B shows exemplary photographs of control and CaMKK2−/− mice.

DETAILED DESCRIPTION

Tumor-associated myeloid cells play a pivotal role in the regulation of processes that control tumor growth and metastasis, and their accumulation in cancer tumors has been identified as an important negative prognostic factor. Here, in part, the inventors show that depletion of Calcium-calmodulin kinase kinase 2 (CaMKK2) activity in myeloid cells inhibits tumor growth in mouse models of cancer. Depletion of CaMKK2 activity is associated with the accumulation of macrophages expressing high levels of the major histocompatibility molecule class II molecule I-A (MHC II I-A), and CD8$^+$ T-cells within the tumor microenvironment. Treatment with CaMKK2 inhibitors was also shown to block tumor growth and facilitate reprogramming of the microenvironment. The inventors further show in the Examples that in human breast cancer biopsies, CaMKK2 expression levels correlate with tumor grade, and in high-grade tumors, both tumor cells and tumor-associated macrophages express high levels of this enzyme. In aggregate, these findings implicate CaMKK2 as a macrophage specific checkpoint and demonstrate that CaMKK2 inhibition, either alone or in combination with other anti-cancer therapeutic agents such as immunotherapies, would be an innovative immunotherapeutic strategy for treating cancer through reprogramming the tumor microenvironment.

Compositions including a CaMKK2 inhibitor and an anti-cancer therapeutic agent are provided herein. As used herein, a "CaMKK2 inhibitor" is any agent capable of partially or fully blocking, inhibiting, or neutralizing one or more of the biological activities of a CaMKK2 protein including, without limitation, a polypeptide, a polynucleotide, or a small molecule. A CaMKK2 inhibitor may function in a direct or indirect manner. For example, the CaMKK2 inhibitor may directly bind to a CaMKK2 protein, thus partially or fully blocking, inhibiting or neutralizing one or more biological activities of a CaMKK2 protein, in vitro or in vivo. The CaMKK2 inhibitor may also function indirectly by (1) interacting with (e.g., activating, inducing, blocking or inhibiting) another molecule that can bind to CaMKK2 or (2) modulating or affecting the expression (i.e, transcription or translation) of a CaMKK2 protein in a cell. Alternatively, the CaMKK2 inhibitor may interfere with the calcium binding, kinase or other activity of CaMKK2 without directly binding to the protein.

Mammalian CaMKK2 proteins are 66-68-kDa kinases including unique N- and C-terminal domains, a central Ser/Thr-directed kinase domain, and a regulatory domain composed of overlapping autoinhibitory and CaM-binding regions. CaMKK2 proteins are auto-inhibited by a sequence located immediately C-terminal to its catalytic domain, and Ca2+/CaM binding causes conformational changes that stimulate kinase activity. Once activated, CaMKK2 proteins can phosphorylate CaMKIV and CaMKI increasing their enzymatic activity. 5' AMP-activated protein kinase α (AMPKα) is an additional substrate of CaMKK2 proteins, and silencing of CaMKK2 proteins in mammalian cells almost completely abolishes AMPK activation. Although CaMKK2 proteins can be detected in many areas of the brain, outside this organ the expression of CaMKK2 proteins is less clear. In the immune system, CaMKK2 proteins have been found exclusively in myeloid cells, including hematopoietic progenitors, peritoneal macrophages and bone marrow-derived macrophages. Genetic ablation of CaMKK2 proteins interferes with development and function of myeloid cells, and in turn has important effects on the inflammatory response.

CaMKK2 proteins may be any of the CaMKK2 proteins found in any mammal including, without limitation, humans or domesticated animals such as dogs, cats, horses, cows, pigs, mice, or rats. The protein sequences of exemplary CaMKK2 proteins are indicated in SEQ ID Nos: 1-11. Suitably, the CamKK2 inhibitors disclosed herein inhibit one of the at least 5 isoforms of the human CaMKK2 protein, including for example, the human CaMKK2 protein indicated in SEQ ID NO: 1. See, e.g., www.uniprot.org/uniprot/Q96RR4.

The CaMKK2 inhibitor may be a polypeptide including, without limitation, a peptide or an antibody. As used herein, the term "antibody" is used in the broadest sense used in the art to refer to polypeptide affinity agents based on antibodies. For example, the antibody may include a polyclonal antibody, a monoclonal antibody, a single chain antibody, or antibody fragments such as Fab, Fab', $F(ab')_2$, Fv fragments, diabodies, linear antibodies, or multispecific antibodies formed from antibody fragments. The antibody may be chimeric, humanized, or fully human. The antibody may be any one of the five known major classes of immunoglobulins including IgA, IgD, IgE, IgG, and IgM. In some embodiments, the CaMKK2 inhibitor may be an anti-CaMKK2 antibody that is capable of binding a CaMKK2 protein and thereby partially or fully blocking, inhibiting, or neutralizing one or more of the biological activities of a CaMKK2 protein such as its calcium binding activity or its kinase activity.

Peptides useful as CaMKK2 inhibitors may be identified using techniques well-known in the art such as phage display. Peptide-based CaMKK2 inhibitors may also include the amino acid sequence located immediately C-terminal to the catalytic domain of CaMKK2 proteins (or variants thereof), which is known to inhibit the kinase activity of CaMKK2 proteins.

The CaMKK2 inhibitor may be a polynucleotide including, without limitation, a dsRNA, a shRNA, an siRNA, a microRNA, an antisense polynucleotide (i.e., DNA or RNA), an aptamer (i.e., DNA or RNA), or a precursor polynucleotide encoding any of the previous polynucleotides. As known in the art, dsRNA, shRNAs, siRNAs, and microRNAs are small RNA molecules that function in RNA silencing and post-transcriptional regulation of gene expression. Such RNA agents are generally engineered using well-known methods to specifically modify the expression of a single or multiple genes of interest. In some embodiments, the CaMKK2 inhibitor may be a dsRNA, an shRNA, an siRNA, microRNA, or antisense polynucleotide, which includes a polynucleotide sequence that is homologous to at least a portion of a CaMKK2 mRNA transcript in a cell that either blocks the transcript's translation and/or targets the transcript for degradation.

Precursor polynucleotides may be DNA constructs encoding dsRNA, shRNA, siRNA microRNA and/or antisense polynucleotides that can be controlled by regulatory elements allowing an expression of the dsRNA, shRNA, siRNA microRNA and/or antisense polynucleotides in a target cell. Exemplary regulatory elements may include polymerase II or III promoters such as, for example, U6 or H1.

Aptamers are polynucleotides (e.g., ssDNA or ssRNA) that bind to a specific target molecule. In some embodiments, the CaMKK2 inhibitor may be an aptamer that is capable of binding a CaMKK2 protein and thereby partially or fully blocking, inhibiting, or neutralizing one or more of the biological activities of a CaMKK2 protein such as its calcium binding activity or its kinase activity.

The CaMKK2 inhibitor may be a small molecule. The small molecule may be chemical molecule having a molecular weight below about 2500 Daltons, 2000 Daltons, 1000 Daltons, or 500 Daltons. Suitable small molecule CaMKK2 inhibitors include, without limitation, STO-609 N28464-13-A1 (referred to as GSKi), or derivatives thereof. See, e.g., Table 1 below. STO-609 is disclosed, for example, in US Patent Publication No. 2013/0253035. STO-609 is a selective, cell-permeable inhibitor of CaMKK proteins. STO-609 has an approximately 5-fold higher affinity for CaMKK2 than CaMKK1 and is often used in vivo or in vitro to suppress the CaMKK2-AMPK pathway. STO-609 may be obtained from commercial suppliers (e.g., Torcis Biosciences). Other selective and targeted inhibitors of CaMKK2, such as GSKi, are in development and known to those of skill in the art.

TABLE 1

| CaMKK2 inhibitor | Structure |
| --- | --- |
| STO-609 | 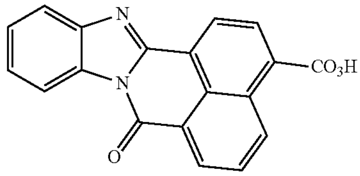  |
| N28464-13-A1 (referred to as GSKi) | 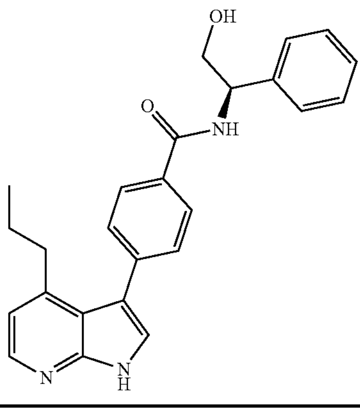  |

The anti-cancer therapeutic agent may be any therapeutic agent that is used to treat cancer in a subject. Suitable anti-cancer therapeutic agents may include, without limitation, radiation, chemotherapy agents, anti-cancer biologics, or immunotherapy agents. Chemotherapy agents are chemotherapeutic compounds that may be used to treat cancer. Suitable chemotherapy agents may include, without limitation, 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, or VM25.

Anti-cancer biologics are biomolecules (e.g., polynucleotides, polypeptides, lipids, or carbohydrates) that may be used to treat cancer. Anti-cancer biologics may include, without limitation, cytokines such as IL-1α, IL-2, IL-2(3, IL-3, IL-4, CTLA-2, IFN-α, IFN-γ, granulocyte-macrophage colony stimulating factor (GM-CSF), IL-12, IL-23, IL-15, IL-7, or any combination thereof; or anti-cancer antibodies such as Rituximab, Trastuzumab, Gemtuzumab, Alemtuzumab, Ibritumomab tiuxetan, Tositumomab, Cetuximab, Bevacizumab, Panitumumab, Ofatumumab, Brentuximab Vedotin, Pertuzumab, Adotrastuzumab emtansine, and Obinutuzumab.

The term "immunotherapy agent(s)" refers to any therapeutic that is used to treat cancer in a subject by inducing and/or enhancing an immune response in that subject. Immunotherapy agents may include, without limitation, checkpoint inhibitors, cancer vaccines, immune cells such as engineered T cells, anti-cancer viruses, or bispecific antibodies. Checkpoint inhibitors are therapeutics, such as antibodies, that block the immune checkpoint pathways in immune cells that are responsible for maintaining self-tolerance and modulating the degree of an immune response. Tumors often exploit certain immune checkpoint pathways as a major mechanism of immune resistance against T cells that are specific for tumor antigens. Many of the immune checkpoints are initiated by receptor-ligand interactions and thus may be blocked by antibodies to either the ligand or receptor or may be modulated by soluble recombinant forms of the ligands or receptors. Such immune checkpoint blockade allows tumor-specific T cells to continue to function in an otherwise immunosuppressive tumor microenvironment. Checkpoint inhibitors, however, are not effective against all cancer types. Furthermore, not every patient that is expected to respond to immune checkpoint blockade actually benefits from treatment with such agents. In part, the present inventors have found that CaMKK2 inhibitors result in the accumulation of more active macrophages and T-cells within a tumor resulting in a more inflamed tumor microenvironment that would be expected to work in synergy with checkpoint inhibitors to make tumors vulnerable to attack and elimination by the immune system. Thus, patients that do not respond to the administration of checkpoint inhibitors alone may benefit from administration of a checkpoint inhibitor(s) and a CaMKK2 inhibitor.

Exemplary checkpoint inhibitors include, without limitation, antibodies or other therapeutics targeting programmed cell death protein 1 (PD1, also known as CD279), programmed cell death 1 ligand 1 (PD-L1, also known as CD274), PD-L2, cytotoxic T-lymphocyte antigen 4 (CTLA4, also known as CD152), A2AR, CD27, CD28, CD40, CD80, CD86, CD122, CD137, OX40, GITR, ICOS, TIM-3, LAG3, B7-H3, B7-H4, BTLA, IDO, KIR, or VISTA. Suitable anti-PD1 antibodies include, without limitation, lambrolizumab (Merck MK-3475), nivolumab (Bristol-Myers Squibb BMS-936558), AMP-224 (Merck), and pidilizumab (CureTech CT-011). Suitable anti-PD-L1 antibodies include, without limitation, MDX-1105 (Medarex), MEDI4736 (Medimmune) MPDL3280A (Genentech/Roche) and BMS-936559 (Bristol-Myers Squibb). Exemplary anti-CTLA4 antibodies include, without limitation, ipilimumab (Bristol-Myers Squibb) and tremelimumab (Pfizer).

Cancer vaccines stimulate the body's immune system to attack cancer cells. Cancer vaccines generally include a tumor antigen in an immunogenic formulation that activates tumor antigen-specific helper T cells and/or cytotoxic T cells and B cells. Vaccines can be in a variety of formulations, including, without limitation, dendritic cells, monocytes, viral, liposomal and DNA vaccines. Suitably, the dendritic cells are autologous and transfected with tumor cells or tumor antigens. Dendritic cells are immune cells that present antigens to T cells, which prompted their application in therapeutic cancer vaccines. Following the loading of dendritic cells with tumor antigens ex vivo, the dendritic cells may be administered as a cellular vaccine which has been found to induce protective and therapeutic anti-tumor immunity. Exemplary cancer vaccines include, without limitation, Sipuleucel-T (Provenge®, or APC8015). Sipuleucel-T is an FDA-approved cancer vaccine developed from autologous dendritic cells (DC) loaded with engineered fusion protein of prostatic acid phosphatase (PAP) and granulocyte-macrophage colony-stimulating factor (GM-CSF).

In the Examples, the present inventors have presented results that suggest that inhibiting CaMKK2 in a tumor environment, such as a lymphoma, can be a new strategy to induce DC maturation and enhance DC functions, thus augmenting the DC vaccine efficacy. For example, the present inventors have shown that CaMKK2−/− dendritic cells, including in BMDCs and splenic DCs, showed better maturation and T-cell stimulation functions. See Appendix. When stimulating BMDCs with LPS to activate TLR signaling, they observed a significant increase in the secretion of activating chemokines and cytokines in CaMKK2−/− cells. IL-12 and IL-15, the two important cytokines that stimulate T-cell activation and expansion, were significantly elevated; while IL-4 and IL-10, the two inhibitory factors for TH1 differentiation and IL-12 secretion, remained stable. The present inventors also demonstrate that when co-cultured with T cells, CaMKK2−/− BMDCs yielded higher IL-12 secretion, better induced IFN-γ from T cells, and better stimulated T-cell activation and proliferation.

An immunotherapy agent may include immune cells (i.e., T cells or B cells) that are adoptively transferred into a subject to attack or reduce cancer cells or cancer cell growth. The immune cells may be autologous or derived from a subject that is different from the subject receiving the immune cells and modified to reduce rejection. The immune cells may also have a natural or genetically engineered reactivity to a subject's cancer. For example, natural autologous T cells have been shown to be effective in treating metastatic cancers. See, e.g., Rosenberg S A et al., *Nat. Rev. Cancer* 8 (4): 299-308 (2008). Natural autologous T cells may be found within a resected subject's tumor. Such T cells can be induced to multiply in vitro using high concentrations of IL-2, anti-CD3 and allo-reactive feeder cells. These T cells are then transferred back into the subject along with, for example, exogenous administration of IL-2 to further boost their anti-cancer activity.

The T cells may also include engineered T cells. Engineered T cells are T cells that have been genetically modified so as to direct T cells to specifically destroy a subject's cancer cells. Engineered T cells may, for example, include T cells that have been genetically modified to express chimeric antigen receptor (CAR) proteins or "CAR T cells." See, e.g., Liddy et al., *Nature Med.* 18:980-7 (2012); Grupp et al., *New England J. Med.* 368:1509-18, (2013). The CAR proteins may include a targeting moiety such as an extracellular single-chain variable fragment (scFv) capable of binding a tumor-associated antigen(s), a transmembrane domain, and intracellular signaling/activation domain(s). The intracellular signaling/activation domain(s) may include, without limitation, CD3ζ signaling domain, 41BB-signaling domains, CD28-signaling domains, or combinations thereof. Suitable tumor-associated antigens include, without limitation, CD19, carcinoembryonic antigen (CEA), diganglioside GD2, mesothelin, L1 cell adhesion molecule (L1CAM), human epidermal growth factor receptor 2 (HER2), fibroblast activation protein (FAP), interleukin 13 receptor α (IL13Rα), EGFR, or EGFR variant 3 (EGFRvIII).

CAR T cells have demonstrated remarkable success in treating blood-borne tumors such as certain kinds of leukemias. CAR T cells, however, have not been as effective at treating solid tumors, which present a number of unique barriers that are absent in blood-borne malignancies. For example, unlike the environment of blood-borne malignancies, CAR T cells must successfully traffic to solid tumor sites in spite of tumor signaling attempting to inhibit such trafficking. Furthermore, once trafficked to a tumor, CAR T cells must infiltrate into the solid tumor in order to elicit tumor-associated antigen-specific cytotoxicity. Even after successful trafficking and infiltration, CAR T cells must evade the immunosuppressive microenvironment of the tumor conferred by, for example, suppressive immune cells (regulatory T cells (Tregs), myeloid-derived suppressor cells (MDSC), tumor-associated macrophages (TAMs), and/or neutrophils (TAN). The present inventors have demonstrated that inhibiting CaMKK2, for example in myeloid cells, is a crucial driver of the immunosuppressive microenvironment in tumors such as breast tumors. Given this ability to dampen the immunosuppressive microenvironment in tumors, the present inventors expect that T cell therapy such as CAR T cell therapy could be improved by also inhibiting CaMKK2 activity by, for example, co-administering a CaMKK2 inhibitor or administering a CaMKK2 inhibitor in advance of the administration of the CAR T cells.

An immunotherapy agent may include an oncolytic virus. As used herein, an "oncolytic virus" refers to any virus that may be used to treat cancer. Exemplary oncolytic viruses include, without limitation, PVS-RIPO, T-VEC, and Onyx-015. PVS-RIPO is a genetically modified oral poliovirus that has been fast-tracked by the FDA for the treatment of recurrent glioblastoma multiforme (GBM). T-VEC (Imlygic) is an FDA-approved oncolytic virus for the treatment of melanoma in patients with inoperable tumors. Onyx-015 is an oncolytic adenovirus.

Bispecific antibodies may also be used as an immunotherapy agent in accordance with the present invention. A bispecific antibody is an antibody having binding sites for a tumor-associated antigen and for a T-cell surface receptor that can direct the lysis of specific tumor cells by T cells. Bispecific antibodies have been used, for example, to successfully treat brain tumors in human patients. See, e.g., Nitta et al., *Lancet* 355:368-371 (1990). Numerous methods to produce bispecific antibodies are known in art including, without limitation, the quadroma method (See, e.g., Milstein and Cuello, *Nature,* 305:537-540 (1983)), use of heterobifunctional cross-linkers to chemically tether two different antibodies or antibody fragments (See, e.g., Staerz et al., *Nature* 314:628-631 (1985); European Patent Application 0453082), or DOCK-AND-LOCK methods (See, e.g., U.S. Pat. Nos. 7,550,143; 7,521,056; 7,534,866; 7,527,787 and 7,666,400).

A bispecific antibody may include a trifunctional antibody that includes two heavy and two light chains, one each from two different antibodies. The two Fab regions are directed against two antigens while the Fc region is made up from the two heavy chains and forms the third binding site, which typically may elicit effector functions. A bispecific antibody may include chemically linked Fab regions, various types of bivalent and trivalent single-chain variable fragments (scFvs), or fusion proteins mimicking the variable domains of two antibodies. Suitable bispecific antibodies include, without limitation, Removab (Trion Pharma), Blincyto (Amgen), AMG-110 (Amgen), ABT-122 (Abbvie), ABT-981 (Abbvie), AFM13 (Affimed Therapeutics), MM-111 (Merrimack Pharmaceuticals), SAR156597 (Sanofi), RG7221 (Roche), RG6013 (Roche), RG7597 (Roche), ALX-0761 (Ablynx), MCLA-128 (Merus), MEDI-565 (AMG-211), MGD006 (Macrogenics), and REGN1979 (Regeneron).

Pharmaceutical compositions including any of the compositions described herein are also provided. The pharmaceutical compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

Methods of treating cancer in a subject are also provided. The methods may include administering any of the compositions or pharmaceutical compositions described herein to a subject in an amount effective to treat the cancer. As used herein, the "subject" may be any mammal, suitably a human, or domesticated animal such as a dog, cat, horse, cow, pig, or a mouse or rat. Exemplary cancers in accordance with the present invention include, without limitation, primary and metastatic breast, ovarian, lymphoma, myeloma, pancreatic, prostate, bladder, lung, osteosarcoma, pancreatic, gastric, esophageal, colon, skin cancers (basal and squamous carcinoma; melanoma), testicular, colorectal, urothelial, renal cell, hepatocellular, leukemia, and central nervous system cancers or pre-cancers.

Treating cancer includes, without limitation, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

An "effective amount" or a "therapeutically effective amount" as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions and pharmaceutical compositions described herein may be administered by any means known to those skilled in the art, including, without limitation, intravenously, intratumoral, intra-lesional, intradermal, topical, intraperitoneal, intramuscular, parenteral, subcutaneous and topical administration. Thus the compositions may be formulated as an injectable, topical or ingestible, suppositions tory formulation. Administration of the compositions and pharmaceutical compositions to a subject in accordance with the present invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage of a CaMKK2 inhibitor and/or anti-cancer therapeutic agent administered in any given case will be adjusted in accordance with the composition or compositions being administered, the volume of the composition that can be effectively delivered to the site of administration, the disease to be treated or inhibited, the condition of the subject, and other relevant medical factors that may modify the activity of the compositions or the response of the subject, as is well known by those skilled in the art. For example, the specific dose of a CaMKK2 inhibitor and/or anti-cancer therapeutic agent for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol. The compositions can be given in a single dose schedule, or in a multiple dose schedule.

The maximal dosage of a CaMKK2 inhibitor and/or anti-cancer therapeutic agent for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will treat cancer by, for example, by reducing tumor size or decreasing the rate of tumor growth by least 10%, 20%, 30%, 40%, 50%, 60%, 70%, 80%, 90%, 100% or more as compared to no treatment.

The effective dosage amounts of a CaMKK2 inhibitor and/or anti-cancer therapeutic agent herein refer to total amounts administered, that is, if more than one composition is administered, the effective dosage amounts of a CaMKK2 inhibitor and/or anti-cancer therapeutic agent corresponds to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The compositions and pharmaceutical compositions described herein may be administered one time or more than one time to the subject to effectively treat cancer. Suitable dosage ranges for a CaMKK2 inhibitor and/or anti-cancer therapeutic agent may be of the order of several hundred micrograms of the inhibitor and/or agent with a range from about 0.001 to 10 mg/kg/day, preferably in the range from about 0.01 to 1 mg/kg/day. Precise amounts of a CaMKK2 inhibitor and/or anti-cancer therapeutic agent required to be administered depend on the judgment of the practitioner and may be peculiar to each subject. It will be apparent to those of skill in the art that the therapeutically effective amount of the compositions and pharmaceutical compositions described herein will depend, inter alia, upon the administration schedule, the unit dose of agent administered, whether the composition is administered in combination with other therapeutic agents, the status and health of the recipient, and the therapeutic activity of the particular composition.

The effectiveness of an anti-cancer therapeutic agent may be enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% when combined with a CaMKK2 inhibitor and relative to a control treated with the anti-cancer therapeutic agent alone. Suitably, the compositions and methods described herein may reduce the size of a tumor or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as saline or relative to administration of the anti-cancer therapeutic agent alone.

The methods of treating cancer in a subject provided herein may include obtaining a sample from the subject; measuring the immune cells in the sample; and administering a CaMKK2 inhibitor to the subject. The methods of treating cancer in a subject provided herein may also include administering to the subject a therapeutically effective amount of a CaMKK2 inhibitor provided that the subject was selected for treatment based on an immune cell infiltration measurement of a tumor sample from the subject. Optionally, such methods may further include administering an anti-cancer therapeutic agent to the subject.

As used herein, a "sample" may include, without limitation a blood sample, bone marrow sample, or a tumor sample from any of the cancers described herein. The immune cells may be any of the immune cells of the immune system in the subject. Preferably, the immune cells may be myeloid cells, B cells or T cells.

The immune cells in the sample may be measured using any techniques that may be used to determine the identity, number, and/or density of immune cells in the sample. Typical techniques include, without limitation, Fluorescence-activated cell sorting (FACS), immunoisolation, and/or immunohistochemistry. Molecular analysis, including liquid biopsy, can also be used to identify cancer molecular type as well as the repertoire of immune cells. Such techniques may employ the use of one or more antibodies that are specific for one or more proteins expressed by an immune cell such as immune cell surface markers. Exemplary immune cell markers include, without limitation, CD3 (T cells), CD8, GZMB (cytotoxic T cells), PD-1, FoxP3 (Treg), RORgamma (Th17), CD4 (T helper cells), CD45RO, (memory T cells), and/or CD20. Two or more markers may also be detected in accordance with the present invention. In some embodiments, the following combinations may be used: CD3+CD8, CD3+CD45RO, CD3+CD20, CD3+GZMB, CD8+CD20, CD8+GZMB, CD8+CD45RO, CD20+GZMB, CD20+CD45RO, GZMB+CD45RO, CD4+CD8, CD4+CD45RO, CD4+GZMB, CD4+CD20, CD8+PD-1+ and all the combinations of 3 markers among the CD3, CD8, CD20, CD45RO, CD4, PD-1 and GZMB markers.

Antibodies used in accordance with the present invention are typically commercially available and can be sourced using available directories, such as Linscott's. Anti-CD3 antibodies may include the 2GV6 antibody commercially available from Roche Ventana Medical Systems (Tucson, Ariz., USA). Anti-CD8 antibodies may include the C8/144B antibody commercially available from Dako (Denmark).

In some embodiments, the immune cells in a tumor sample from a subject may be measured in order to determine the level of immune cell infiltration in the sample. Such levels of immune cell infiltration have been found to be a useful prognostic marker for determining whether a particular cancer will respond to treatment with an anti-cancer therapeutic agent. See, e.g., Galon et al., Journal of Translational Medicine 10:205 (2012); Kirilovsky et al., International Immunology (2016) doi: 10.1093/intimm/dxw02. Generally, it has been appreciated in the art that if the immune cell infiltration of a tumor sample from a subject is low, it is unlikely that the subject will respond effectively to an anti-cancer therapeutic agent such as an immunotherapy agent. For example, it is known in the art that subjects having tumor samples with low immune cell infiltration will be less likely to benefit from the administration of checkpoint inhibitors, T cell therapy, or other immunotherapies. See Kirilovsky et al., International Immunology (2016) doi: 10.1093/intimm/dxw02. To address this problem, the present inventors have found that such subjects may nevertheless benefit from administration of an anti-cancer therapeutic agent such as an immunotherapy agent if the subject is also administered a CaMKK2 inhibitor. As shown in the present application, inhibition of CaMKK2 leads to a dramatic inhibition of the immune-suppressive microenvironment in tumors. By inhibiting this immune-suppressive microenvironment using a CaMKK2 inhibitor, the present inventors have discovered a potential new way of increasing the effectiveness of anti-cancer therapeutic agents such as immunotherapy agents in subjects that would otherwise not respond to such agents.

Given this discovery, in some embodiments, the subject may be administered the CaMKK2 inhibitor if the immune cell measurement in the sample is indicative of a poor prognosis (cancer recurrence after resection and or treatment with a single chemotherapeutic) or a likelihood of therapeutic resistance to an anti-cancer therapeutic agent. One, but not the only potential way of determining whether the immune cell infiltration in the tumor sample is indicative of a poor prognosis or a likelihood of therapeutic resistance to the anti-cancer therapeutic agent, may be to determine an Immunoscore. The present methods, thus, may further include determining an Immunoscore based on the immune cells measured in a tumor sample.

Immunoscore is becoming one validated prognostic factor for quantitating the immunosuppressive microenvironment in a given tumor sample. See, e.g., Galon et al., *Science* 313:5795 1960-1964 (2006); Pages et al., *New Engl. J. Med.* 353:2654-2666 (2005). Methods for determining an Immunoscore are known in the art as described, for example, in U.S. Patent Application 2015/0153349 and WO 2007/045996. An Immunoscore may be 0, 1, 2, 3, or 4. Typically, a lower Immunoscore indicates a higher the likelihood of a poor prognosis or resistance to a desired anti-cancer therapeutic agent. In some embodiments of the present methods, the subject is administered the CaMKK2 inhibitor if the Immunoscore for the sample is 0, 1, 2, 3, 1 or below, 2 or below, or 3 or below.

The methods of the present invention also include methods of treating cancer in a subject including administering to the subject a therapeutically effective amount of a CaMKK2 inhibitor and administering to the subject a therapeutically effective amount of an anti-cancer therapeutic agent to the subject. The CaMKK2 inhibitor may be administered before, after, or concurrently with the anti-cancer therapeutic agent. In some embodiments, the CaMKK2 inhibitor is administered at least 6 hours, 12 hours, 18 hours, 1 day, 2 days, 3 days, 4 days, 5 days, or more prior to the anti-cancer therapeutic agent. In some embodiments, the anti-cancer therapeutic agent is administered at least 6 hours, 12 hours, 18 hours, 1 day, 2 days, 3 days, 4 days, 5 days, or more prior to the CaMKK2 inhibitor.

Kits are also provided. The kits may include a CaMKK2 inhibitor and an anti-cancer therapeutic agent. The kits may also include the antibodies or other reagents needed for determining the Immunoscore of the cancer. The kits may further include the components required to perform any of the methods disclosed herein.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms “a”, “an”, and “the” mean “one or more.” For example, “a protein” or “an RNA” should be interpreted to mean “one or more proteins” or “one or more RNAs,” respectively.

As used herein, “about,” “approximately,” “substantially,” and “significantly” will be understood by persons of ordinary skill in the art and will vary to some extent on the context in which they are used. If there are uses of these terms which are not clear to persons of ordinary skill in the art given the context in which they are used, “about” and “approximately” will mean plus or minus ≤10% of the particular term and “substantially” and “significantly” will mean plus or minus >10% of the particular term.

The following examples are meant only to be illustrative and are not meant as limitations on the scope of the invention or of the appended claims.

EXAMPLES

Example 1: Calcium-Calmodulin Dependent Kinase Kinase 2 in Myeloid Cells is a Key Driver of the Immune-Suppressive Microenvironment in Breast Cancer Tumor-associated myeloid cells play a pivotal role in the regulation of processes that control tumor growth and metastasis, and their accumulation in breast tumors has been identified as an important negative prognostic factor. Here, we show that depletion of Calcium-calmodulin kinase kinase 2 (CaMKK2) in myeloid cells inhibits tumor growth in mouse models of mammary cancer. This activity is associated with the accumulation of macrophages expressing high levels of the major histocompatibility molecule class II molecule I-A (MHC III-A), and CD8$^+$ T-cells within the tumor microenvironment. Treatment with CaMKK2 inhibitors was also shown to block tumor growth and facilitate reprograming of the microenvironment. In human breast cancer biopsies, CaMKK2 expression levels correlate with molecular type, and in the most malignant tumors both tumor cells and tumor-associated macrophages were shown to express high levels of this enzyme. In aggregate, these findings implicate CaMKK2 as a macrophage specific checkpoint, the inhibition of which may have utility in the immunotherapy of breast cancer.

Materials and Methods

All studies involving the use of animals were conducted after prior approval by the Duke institutional animal care and use committee (IACUC).

Mice

Tg(Camkk2-EGFP)DF129Gsat reporter mice were originally provided by the Mutant Mouse Regional Resource Centers (MMRRCC) (S. Gong et al., A gene expression atlas of the central nervous system based on bacterial artificial chromosomes. *Nature* 425, 917-925 (2003)). This transgenic strain contains the coding sequence for enhanced green fluorescent protein (EGFP), followed by a polyadenylation signal, inserted into the mouse genomic bacterial artificial chromosome RP23-31J24 at the ATG transcription initiation codon of the calcium/calmodulin-dependent protein kinase kinase 2 β (Camkk2) gene so that expression of the reporter mRNA/protein is driven by the regulatory sequences of the mouse gene. Tg(Camkk2-EGFP)BL/6Gsat were generated backcrossing Tg(Camkk2-EGFP)DF129Gsat for at least 4 generation. C57BL/6 mice were purchased from the Jackson Laboratory (CA, USA). Wildtype (WT) and Camkk2$^{-/-}$ mice have been described previously (K. A. Anderson et al., Hypothalamic CaMKK2 contributes to the regulation of energy balance. *Cell metabolism* 7, 377-388 (2008)). LysM-Cre+ CaMKK2$^{fl/fl}$ and littermates controls LysMCre+; CaMKK2$^{wt/wt}$ were generated by crossing B6.129P2-Lyz2$^{tm1(cre)Ifo/J}$ mice from the Jackson Laboratory with CaMKK2$^{loxp}$ mice (K. A. Anderson et al., Hypothalamic CaMKK2 contributes to the regulation of energy balance. *Cell metabolism* 7, 377-388 (2008)). Mice were backcrossed to C57BL/6 at least four times during their generation. Genotypes were confirmed by PCR. All the mice were used between 8-16 weeks, with gender and age matched in experimental groups and control groups. The animals were housed in Duke University animal facilities under a 12-hour light/12-hours dark cycle with food and water ad libitum provided. All animal care and experimental procedures were approved by National Institute of Health and Duke University Institutional Animal Care and Use Committee, and in compliance with the guidelines.

Murine Mammary Tumors

MMTV-PyMT grafts: MMTV-PyMT mice were backcrossed onto a C57BL/6 background (C. T. Guy, R. D. Cardiff, W. J. Muller, Induction of mammary tumors by expression of polyomavirus middle T oncogene: a transgenic mouse model for metastatic disease. *Mol Cell Biol* 12, 954-961 (1992)). Resulting mammary tumors were excised, washed in PBS and diced into equal sized pieces. Tumor pieces were orthotopically grafted into the mammary fat pad of wildtype or Camkk2$^{-/-}$ mice. Resulting tumor growth was assessed by direct caliper measurement.

E0771, 4T1 and Met1 grafts: 200,000 of the indicated cells were grafted orthotopically into the mammary fat pad of mice. 4T1 and Met1 cells were grafted in 50% matrigel. Resulting tumors were assessed by direct caliper measurement. To get sizable tumors in Camkk2−/− mice for IHC and flow cytometry studies, a higher number of E0771 ($4\times10^5$) where grafted. This information has been reported in the corresponding figures.

MMTV-PyMT growth: MMTV-PyMT mice on an FVB background (Jackson Laboratory) were bred in-house. Treatment with STO609 was initiated after primary tumors were palpable, and results reported as fold change from initial tumor burden.

Drug Treatments: STO609 was synthesized at Duke University Small Molecule Synthesis Facility, and N28464-13-A1 (referred to as GSKi) was provided by GSK (GlaxoSmithKline). These drugs were administered intraperitoneally daily. STO609 treatment was initiated at post-graft day 1 for E0771, day 7 for Met1 and day 2 for 4T1. These experiments were repeated independently by a different investigator using a different batch of STO-609 (Tocris Biosciences, Bristol, UK). GSK treatment was initiated at post-day 2.

Statistics: Statistical differences in tumor volumes were assessed by two-way ANOVA followed by a Bonferroni's multiple comparison test. $P<0.05$ was considered statistically significant.

Murine Tumor Dissection

Tumors were removed from mice and minced with a surgical scalpel. Minced tissues were added to 5 ml HBSS containing $Ca^{2+}$ and $Mg^{2+}$ (ThermoFisher Scientific, MA, USA), and supplied with collagenase 2 mg/ml and DNase 0.1 mg/ml (Roche, Basel, Switzerland). Subsequently, they were transferred in gentleMACS C tubes, dissected with gentleMACS dissociator (Miltenyi, Bergisch Gladbach, Germany) and incubated for 45 at 37° C. At the end of this incubation, tumors were dissected again with gentleMACS dissociator, and cell suspension passed through 70 μm-cell strainers (Coring, NY, USA), washed twice in PBS w/2% FBS and used for FACS analysis.

Flow Cytometry

Staining of tumor-infiltrating E0771 tumors: $5\times10^6$ cells suspension from dissected tumors were surface stained with APC Cy7-CD3, PE-CD8, PE Cy7-CD4, APC PD-1 (all from BioLegend, CA, USA). Cells were incubated for 15 min at 4° C., washed with PBS-2% FCS. PerCP/Cy5.5 PD-1 antibody (BioLegend, CA, USA) was used for intracellular staining on fixed and permeabilized cells, according with manufacture's protocol (BioLegend). For myeloid cells staining, cells were incubated with PE anti-mouse/human CD11b, PE-Cy7 anti-mouse Ly6G, APC anti-mouse F4/80 (all from BioLegend), PerCpCy5.5 anti-mouse Ly6C, APC Cy7-I-A and Fixable Viability Dye eFluor 450 (eBioscience, CA, USA) at 4° C. for 15 min in dark. Subsequently, cells were washed with PBS w/2% FBS and analyzed by FACS. Bone marrow-derived macrophages ($1\times10^6$) were stained with PE anti-mouse/human CD11b, APC anti-mouse F4/80 (BioLegend), APC Cy7-I-A and Fixable Viability Dye eFluor 450 (eBioscience). The stained cells were analyzed using a BD FACSCanto flow cytometer (BD, NJ, USA). Data is analyzed using FlowJo (TreeStar, OR, USA).

CD8+ Cell Depletion

To deplete CD8+ cells, mice were injected intra-peritoneally with anti-mouse CD8 monoclonal antibody or its IgG control isotype (BioXCell, NH, USA) each at 200 μl at the concentration of 1 mg/ml 4 days and 1 day before tumor inoculation, and every 3 days after tumor cell injection. The effect of CD8 depletion was monitored by flow cytometry using 50 μl peripheral blood staining with APC anti-mouse CD8, APC-Cy7 anti-mouse CD45.2 (BioLegend) at the same time.

Bone Marrow-Derived Macrophages (BMDM)

Protocol used for generating BMDM has been described previously (L. Racioppi, P. K. Noeldner, F. Lin, S. Arvai, A. R. Means, Calcium/calmodulin-dependent protein kinase kinase 2 regulates macrophage-mediated inflammatory responses. *J Biol Chem* 287, 11579-11591 (2012)). Briefly, hind limb bones were removed from mice and crushed in a mortar with 5 ml of Hanks' balanced salt solution (Mediatech, Manassas, VA), plus 2% FBS (Gemini Bio-Products, West Sacramento, CA) supplemented with 2 mM EDTA. Bone marrow (BM) cell suspensions were passed through a 70-μm strainer (BD Falcon) and stratified on Lympholyte (Cedarlane, Burlington, NC). The low-density fraction containing BM nucleated cells was collected, and the concentration was adjusted to $2\times10^6$ cells/ml in complete medium (10% fetal calf serum DMEM, high glucose, supplemented with glutamine, pyruvate, and HEPES, no-phenol red) containing 30% L929-conditioned medium (differentiation medium). Subsequently, BM cells were cultured 5 days in Corning® Costar® Ultra-Low attachment multiwell plates (Sigma). To establish the purity of BMDM, cells were double-stained with anti-CD11b and anti-F4/80 antibodies. Based on this analysis, more than 95% of cells co-expressed these markers, which is typical for macrophages. In same experiments, tumor-conditioned medium (20% v/v) was added to differentiation medium.

Immunoblot

BMDM were washed three times with 2 ml of ice-cold PBS and lysed with 0.15 ml of M-PER mammalian protein extraction reagent with Halt protease and phosphatase inhibitor (Thermo Scientific). Equal amounts of protein sample/lane were denatured and resolved by SDS-PAGE. Proteins were transferred to Immobilon-FL membrane (Millipore, Billerica, MA), and quantitative Western blotting was performed using the Odyssey infrared Western blotting detection system (LI-COR Biosciences, Lincoln, NE). Primary antibodies used were anti-CaMKK (BD Biosciences); anti-actin (Sigma-Aldrich); anti-phospho-CaMKK1 ($Thr^{177}$; Santa Cruz Biotechnology, inc.); anti-AMPKα ($Thr^{172}$), and AMPKα from Cell Signaling (Danvers, MA). Secondary antibodies used were anti-mouse IgG Alexa Fluor 680 (Invitrogen) and anti-rabbit IgG IRDye800-conjugated antibody (Rockland Immunochemicals, Gilbertsville, PA).

Stimulation of BMDM with Lipopolysaccharide

BMDM generated as described above, were harvested, washed and cultured in complete medium for 24 hours at a density of $5\times10^4$ cells/well on 24-well plates, in the presence or absence of LPS (100 ng/ml, Sigma). After 24-hours, supernatants fluids were collected for cytokines detection.

BMDM-T-Cell Co-Culture

T cells were separated from spleens of C57BL/6 mice. The spleens were removed using sterilized sectioning scissors and smashed with the end of the plugs from the 1.5 ml syringes on a 70 μm cell strainers (Coring). Cells were flushed into 50 ml centrifuge tubes (BD falcon, Mass., USA) using PBS with 2% FBS and 2 mM EDTA. After spinning down the cells, the erythrocytes were removed using the red blood cell lysis buffer (Biolegend) followed by two washes. The T cells were further enriched using the Pan T Cell Isolation Kit II (Miltenyi, Bergisch Gladbach, Germany). T cells were stained with FITC anti-mouse CD3 (Biolegend) and detected by flow cytometry for enrichment purity. After two washings in PBS with 2% FBS and 2 mM EDTA, $1\times10^7$ T cells were re-suspended in 1 ml plain PBS with 2 μM CFSE (MitoSciences, OR, USA) and incubated at 37° C., 5% $CO_2$ for 20 min. 35 ml RPMI with 10% FBS were subsequently added to the cells and incubated for additional 10 min. Subsequently, T-cells were washed twice in 2% FBS and 2 mM EDTA. Cell number was determined and $1\times10^5$ CFSE-labeled T cells and $1\times10^3$ BMDM were seeded into 96-well plates (Corning) with 200 μl complete media in the presence or absence of 10 ng/ml purified NA/LE hamster anti-mouse CD3e (BD Biosciences). After 24-hours supernatants fluids were collected for cytokines detection. T-cell proliferation was measured at 72-hours by flow cytometry.

Cytokine Detection

Cytokines were detected in supernatants fluid using MILLIPLEX® 32-MAP Mouse Cytokine/Chemokine Magnetic Bead Panel (EMD Millipore, Darmstadt, Germany) and Luminex® (Luminex, TX, USA).

Tumor-Conditioned Medium

E0771 mouse breast cancer cell line was purchased from ATCC. Cells were cultured in RPMI-1640 (Gibco, MA, USA) supplied with 2 mM L-glutamine, 1.5 g/L sodium bicarbonate, 1.0 mM sodium pyruvate (all from Gibco, MA, USA), and 8% fetal bovine serum (FCS, Hyclone, MA, USA). Cells were kept in humidified 37° C. $CO_2$ incubator and passed at 70% confluence. To generate conditioned medium, medium was removed from 70%-confluent culture and replaced with fresh RPMI-1640 8% FCS. After 3 days, culture supernatants were collected, and aliquots stored at −80°. Cytokines in conditioned medium were analyzed as described above.

Human Tissues

We used tissue microarrays that included duplicate 1 mm cores of formalin-fixed, paraffin embedded primary human breast carcinomas from a group of 47 interpretable tumors from Vienna, Austria (G. Heller et al., Downregulation of TSLC1 and DAL-1 expression occurs frequently in breast cancer. *Breast Cancer Res Treat* 103, 283-291 (2007)); and 68 samples from Roswell Park Cancer Institute (RPCI), NY (A. K. Sood et al., Expression characteristics of prostate-derived Ets factor support a role in breast and prostate cancer progression. *Hum Pathol* 38, 1628-1638 (2007)). For all tumors, grade and ER/PR/HER2 biomarker data were available.

CaMKK2 IHC Analysis

TMA sections were deparaffinized, treated with sub-boiling antigen retrieval buffer (citrate, pH 6) for 20 minutes, and then reacted with an anti-CaMKK2 rabbit monoclonal antibody ( ) at 1:500 for 2 hours. The detection reaction utilized the rabbit Envision kit from Dako. Diaminobenzidine (DAB) was used as chromogen, with hematoxylin as counterstain. The IHC experiments were performed on an automated immunostainer (Intellipath from Biocare). Paraffin-embedded cells blocks of THP cells served as external positive controls. Positive cells showed granular cytoplasmic reactivity. Positive cells showed granular cytoplasmic reactivity. A board certified pathologist performed all analysis including cell type identification and staining intensity. Macrophages, endothelial cell and lymphocytes were identified by morphology. Staining intensity in tumor cells was scored as 0 (absent), 0.5 (borderline), 1 (weak), 2 (moderate) or 3 (strong). For statistical analysis, the tumors were categorized as weak (0, 0.5, 1), and overexpressed (2,3). Ordinal logistic regression was used for binary outcomes and proportional odds regression was used for Grade and molecular class (TN, LA, LB). Score was modeled as a binary predictor with levels weak and overexpressed. For outcomes with low cell counts a Fisher's exact test of association was used. Analyses were conducted in SAS version 9.3 (SAS Institute, Cary, NC) and the R environment for statistical computing.

Statistics

Figures 2A, 2B, 2C:
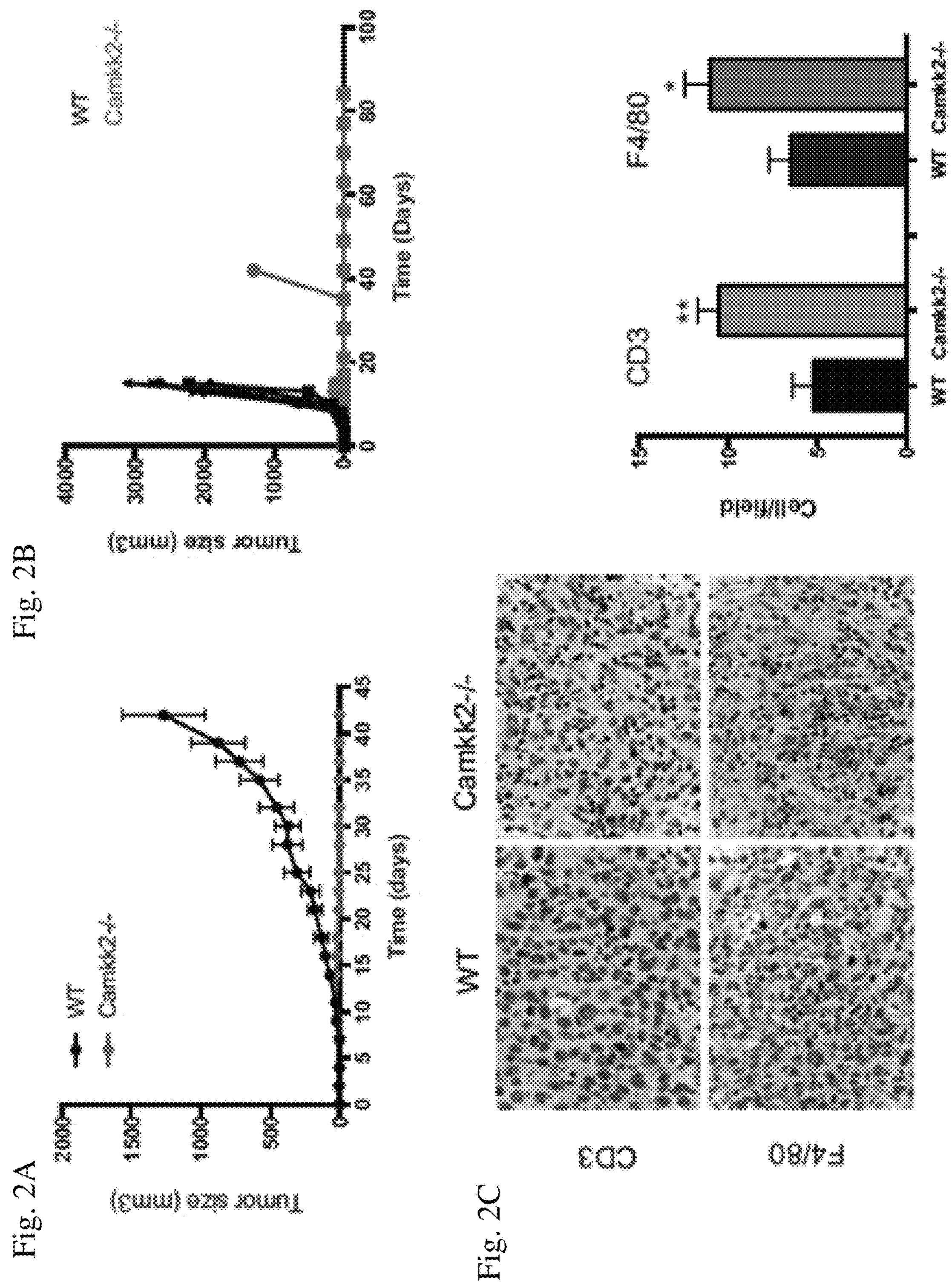
FIG. 2A shows mammary tumors from MMTV-PyMT mice propagated in a C57BL/6 background were harvested, diced and orthotopically grafted into syngeneic C57BL/6 mice that were wildtype or knockout for CaMKK2 (WT and Camkk2$^{-/-}$, respectively; mean+/−SEM; N=10 in each group).
FIG. 2B shows murine E0771 ($2\times10^5$) cells were orthotopically grafted in WT and Camkk2$^{-/-}$ mice, and subsequently tumor volume measured as indicated (mean+/−SEM; N=5 in each group).
FIG. 2C shows increased accumulation of macrophages and T-cells in E0771 tumors propagated in Camkk2$^{-/-}$ mice. Representative CD3 and F4/80 staining of E0771 tumor sections of tumors grown in WT and Camkk2$^{-/-}$ mice (Left). Quantitation of CD3+ and F4/80+ cells in high-power optic fields in stained sections (six fields for each section) (N=3 in each group) (Right). Asterisks refer to $p<0.05$, 0.01, 0.005 and 0.001 (*, , * and ****, respectively).
Figure 3A:
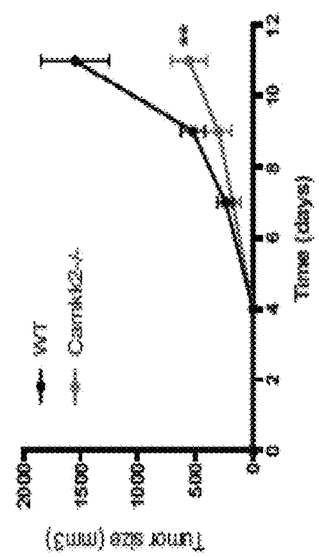
Figure 3B:
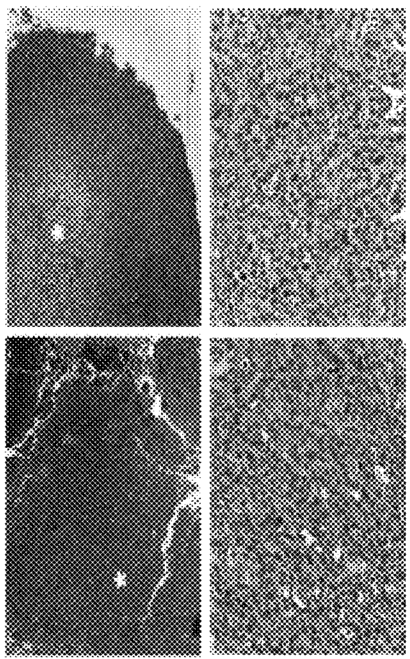
(FIG. 3B) tumor sections stained with hematoxylin and eosin (H & E) at low and high power optic field images (upper and lower panel, respectively)
Figure 3C:
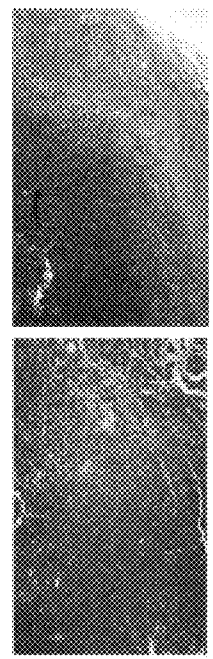
(FIG. 3C) Trichrome staining (low power optic field images)
Figure 6B:
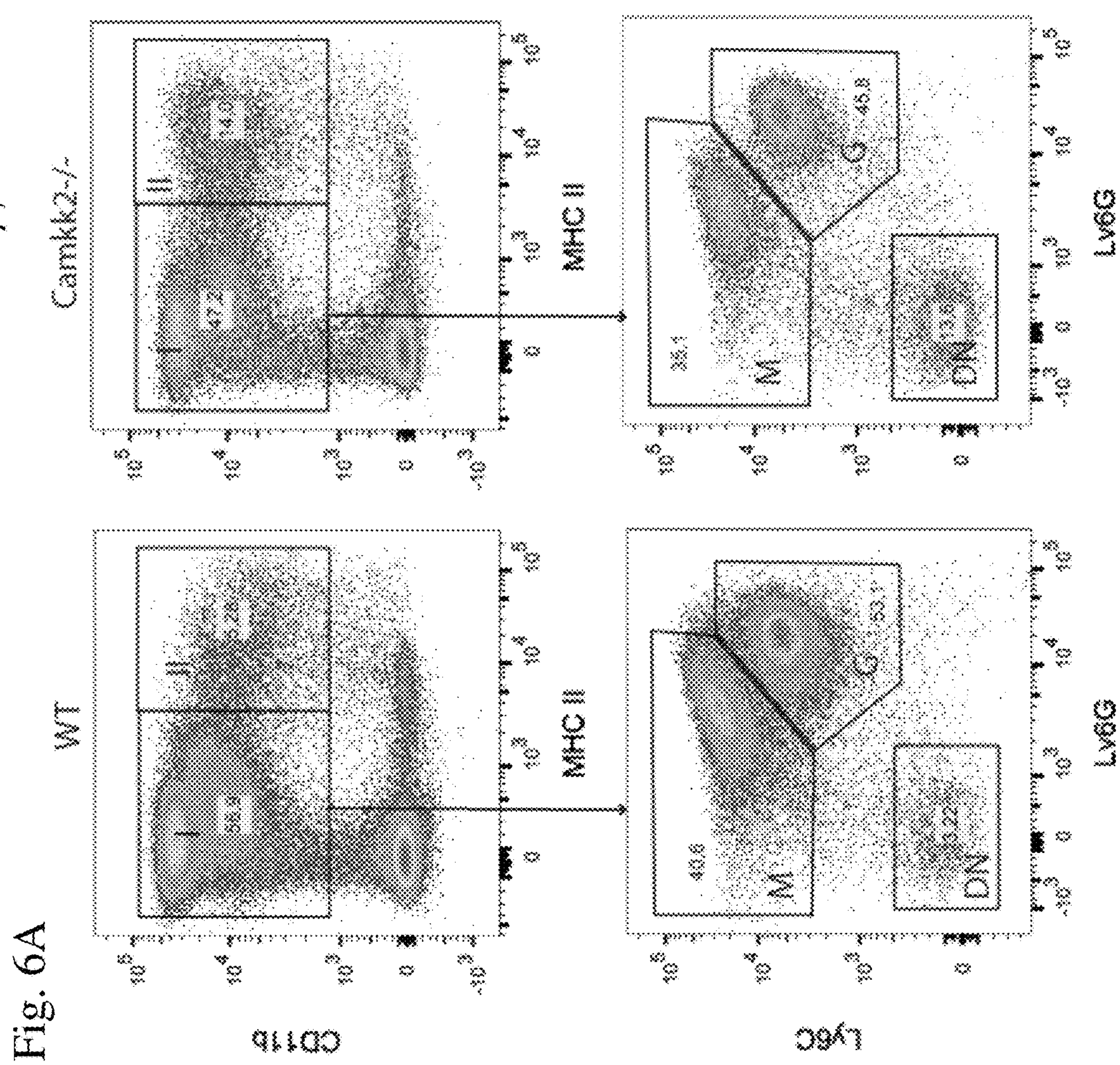
FIG. 6B is a Bar graph reporting mean±SEM (N=6) of M, G and DN subsets (as a percentage) in gate I (n=3 tumors). The experiment was replicated with similar results. Asterisks refer to *p<0.05, p<0.01, *p<0.005 and ****p<0.001, respectively.
Figure 7A:
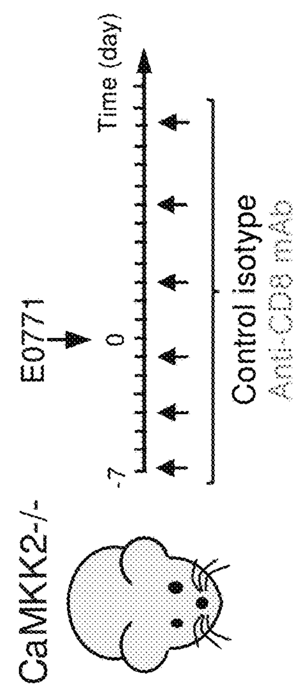
FIG. 7A-B shows depletion of CD8$^{+}$ cells in Camkk2$^{-/-}$ mice using an anti-CD8 antibody. Anti-CD8 or isotype control antibodies were inoculated intraperitoneally, according to the regime outlined (FIG. 7A).
Figure 7B:
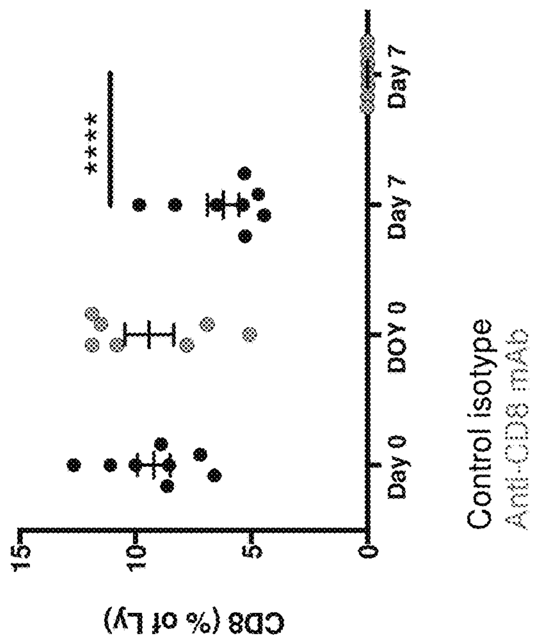
Figure 8A:
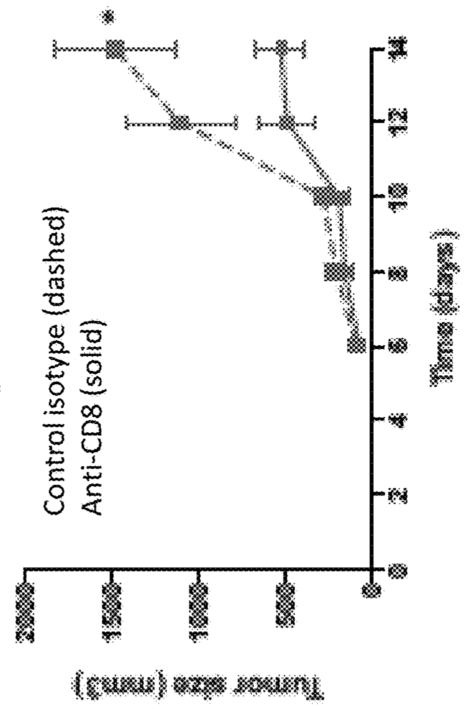
FIG. 8A shows mammary tumor growth in Camkk2−/− mice depleted of CD8+ T-cells. Camkk2−/− mice were treated with anti-CD8 antibody or control isotype each 3 days starting a week before tumor cell inoculation. At day 0, mice E0771 cells were orthotopically grafted, and treated with antibodies every 4 days. Graph shows tumors size (mean+/−SEM; N=6 in each group).
Figure 8B:
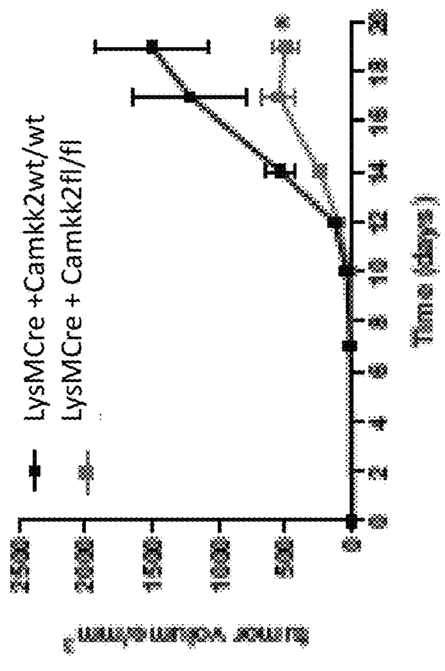
FIG. 8B: Mammary tumors fail to grow in mice lacking CaMKK2 expression in myeloid cells. E0771 cells were orthotopically grafted into LysMCre+ CaMKK2wt/wt and LysMCre+ CaMKK2fl/fl mice. Tumors volumes were measured (mean+SEM; N=8 each group). Asterisks refer to p<0.05, 0.01, 0.005 and 0.001 (*, , * and ****, respectively).
Figure 9A:
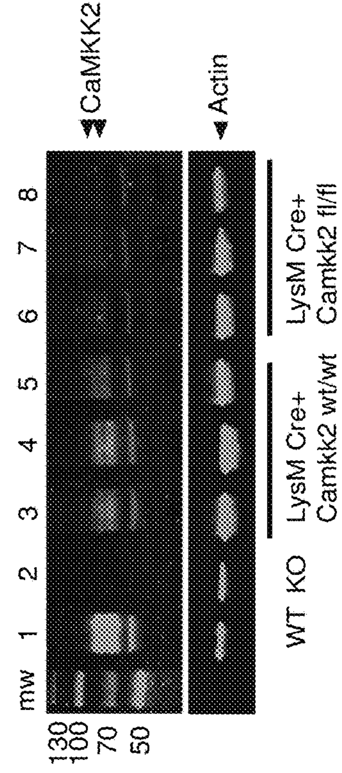
FIG. 9A-C. Characterization of LysM-Cre Camkk2$^{loxP}$ mice.
Figure 9B:
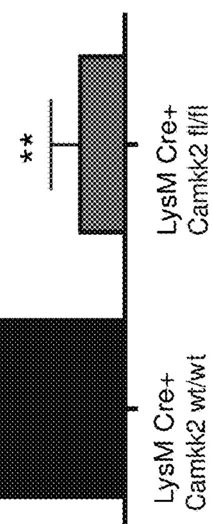
Figure 9C:
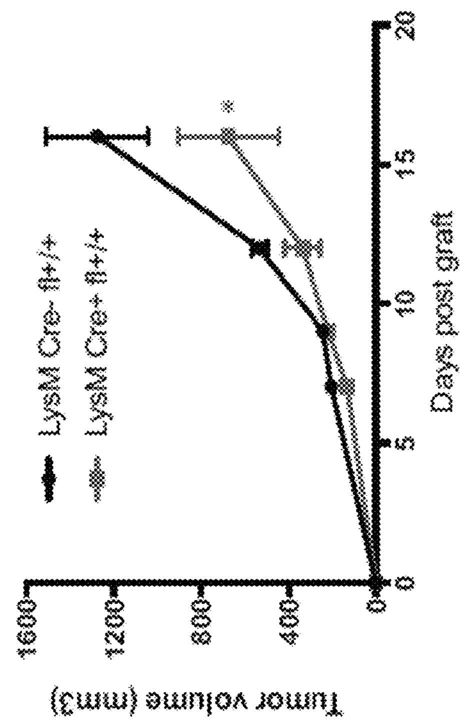
Figure 13A:
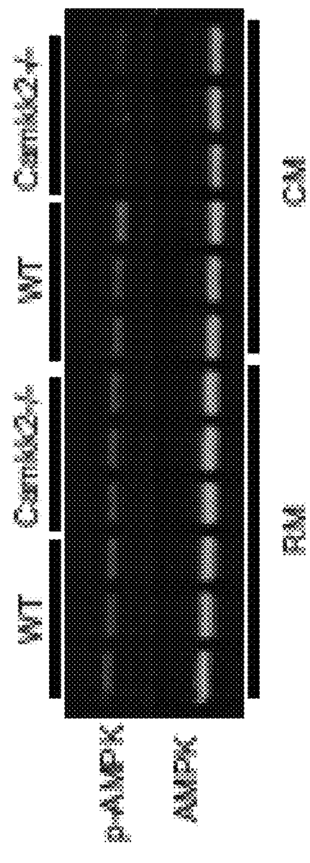
FIG. 13A shows expression of phosphorylated (T-172; p-AMPK) and total AMPKα was assessed by immunoblot.
Figure 13B:
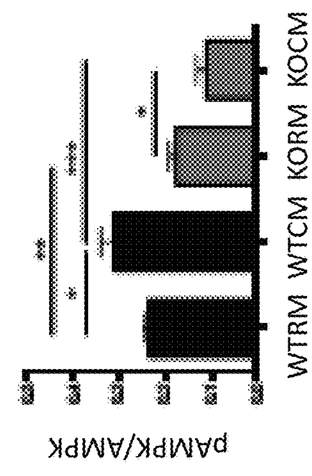
FIG. 13B shows quantification of p-AMPK/AMPK ratio. RM and CM refer to BMDM generated in regular or E0771-conditioned medium, respectively. Asterisks refer to *p<0.05, p<0.01, *p<0.005 and **p<0.001, respectively.
Figure 13C:
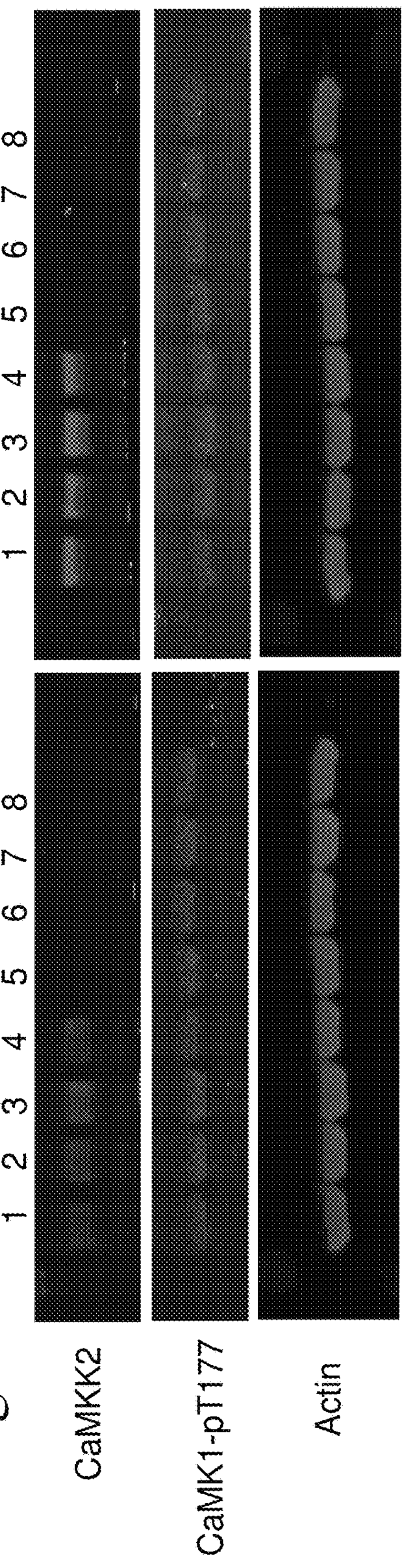
FIG. 13C shows CaMKK2 and phospho-CaMK1 expression in macrophages generated from bone marrow isolated from WT and Camkk2$^{-/-}$ mice. Immunoblots of protein lysates from WT and Camkk2$^{-/-}$ bone marrow-derived macrophages generated in regular differentiation medium in the presence or absence of E0771-conditioned medium.
Figure 13D:
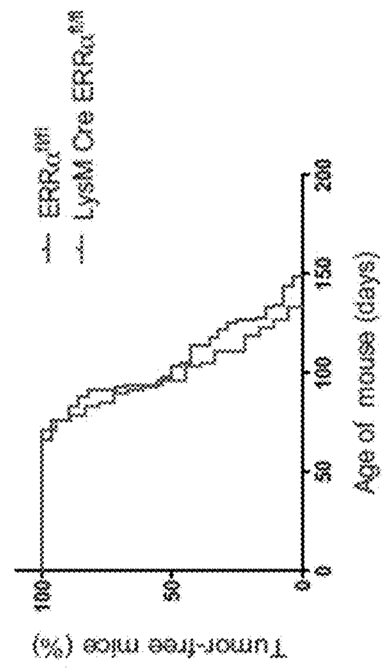
FIG. 13D-G show myeloid cell-specific deletion of ERRα in the MMTV-PyMT mouse model of breast cancer. Tumor latency (FIG. 13D), tumor growth (FIG. 13E), and primary tumor weight at the time of harvest (FIG. 13F) were measured in mice with myeloid cell-specific deletion of ERRα (LysM Cre$^{+}$ ERRα$^{fl/fl}$ n=30) and controls (ERRα$^{fl/fl}$ n=21).
Figure 13E:
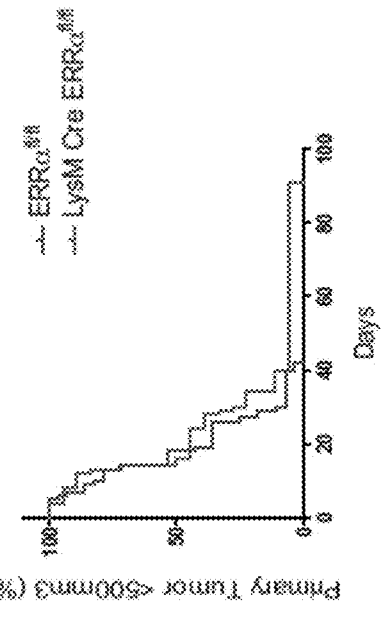
Figure 13F:
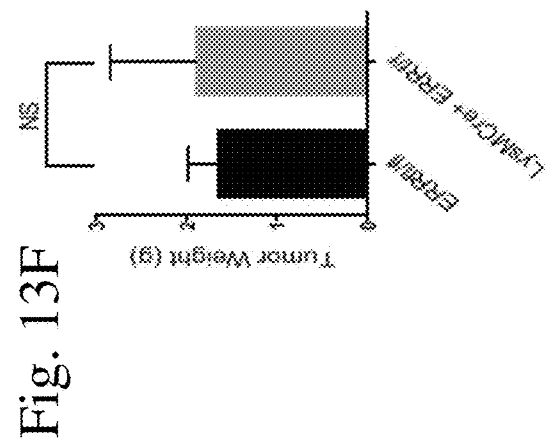
Figure 13G:
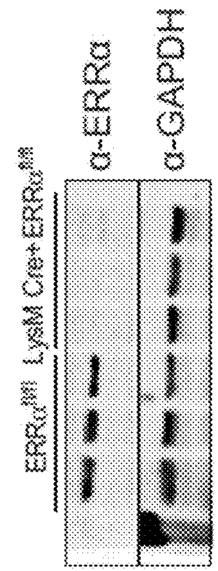
Figure 14A:
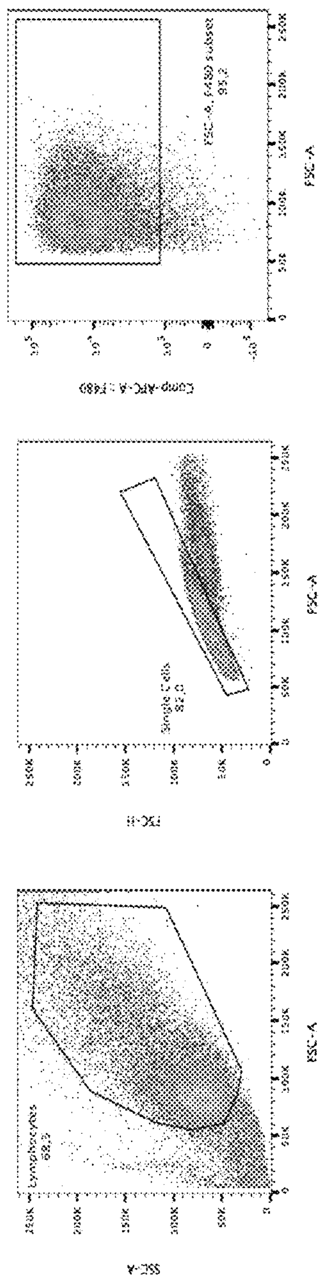
FIG. 14A-B show immuno-phenotype of WT and Camkk2$^{-/-}$ BMDM generated in the presence of regular or E0771-conditioned medium.
Figure 14B:
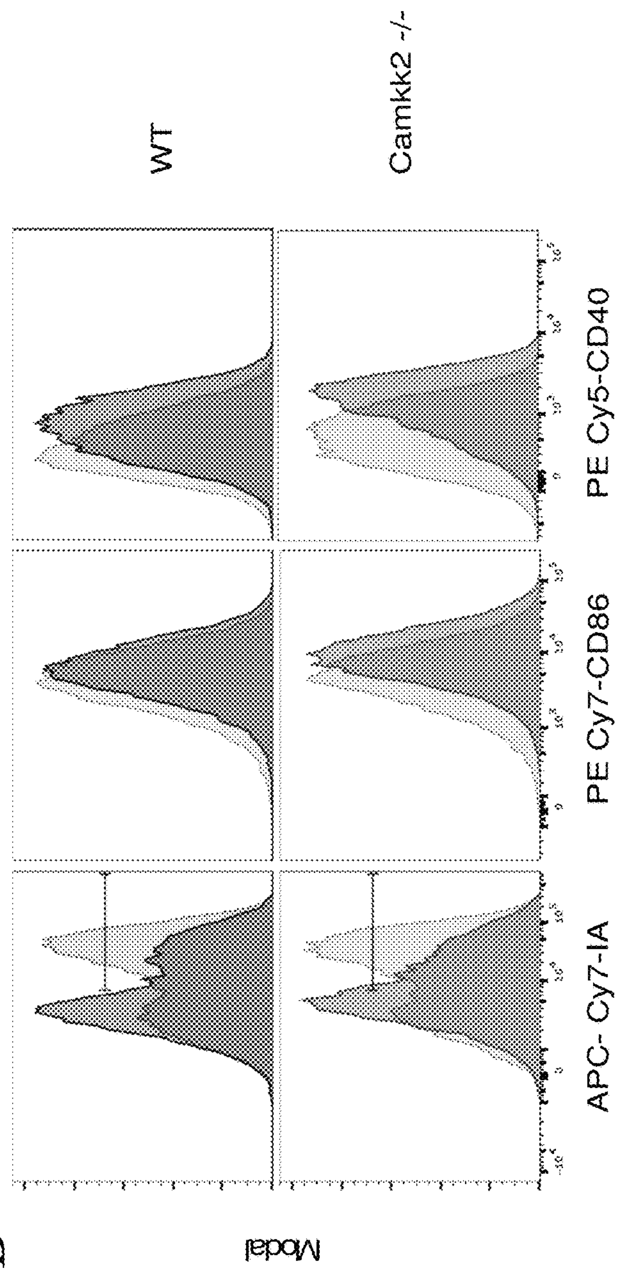
Figures 15A, 15B, 15C, 15D:
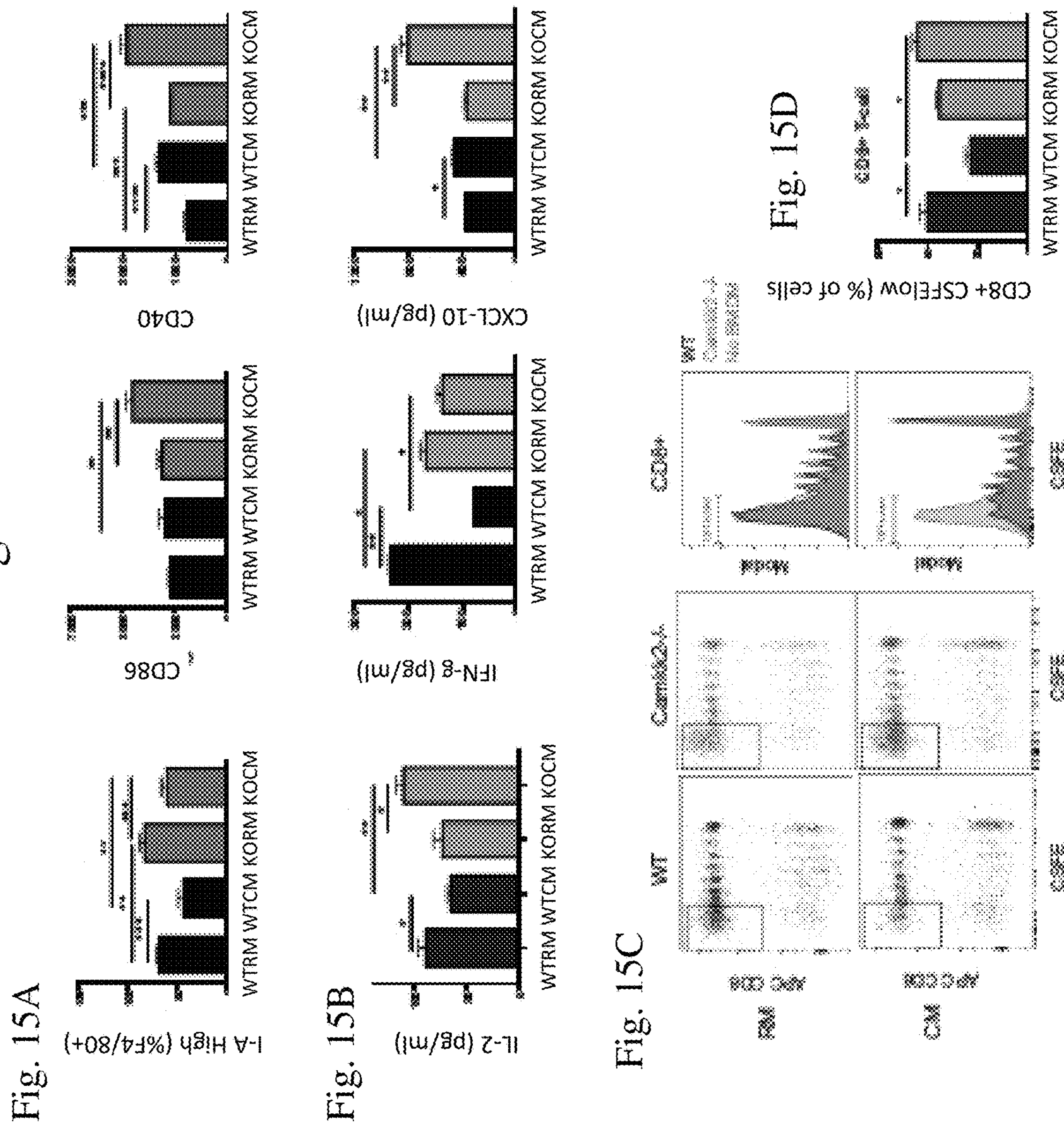
FIG. 15B-D BMDM were cultured with CSFE-labeled T cells isolated from wildtype mice (1:100 BMDM/T-cell ratio), in the presence of an optimal amount of anti-CD3 antibody.

Values were assessed for normality and where appropriate either ln-transformed or a non-parametric test was selected. FIGS. 1A, B, F and G; FIG. 3A, D; FIG. 14: 2-way ANOVA followed by Bonferroni's post-hoc t-test. FIGS. 1C, D, E FIGS. 2B, C, D, F; FIG. 3B-C; FIG. 6C; FIG. 7A-B, FIG. 8B; FIG. 9B-C; FIG. 13; FIG. 15C: unpaired two-tailed student's t-test compared between two groups; FIG. 17: Kaplan-Meier curves compared to each other using log rank test. Graphpad Prism was used for analysis unless otherwise stated. Statistical approaches for Table 2 and Table 3 have been described under CaMKK2 IHC Analysis.

Results

The recruitment of innate immune cells, notably macrophages, is an important process in the initial phases of tumor development[2,3]. In response to cues within the tumor microenvironment, myeloid cells can differentiate into tumor-associated macrophages (TAMs), cells that have the ability to promote blood vessel formation, and which can support both primary tumor growth and distal metastasis. TAM are also responsible for the establishment of a robust immune-suppressive tumor ecosystem by inhibiting the differentiation and function of effector T-cells, and stimulating the intratumoral accumulation of regulatory T-cells (Tregs) and myeloid derived suppressor cells (MDSCs)[4-6]. Not surprisingly, TAM density in primary tumors is strongly associated with poor outcome in breast cancer[7-9]. These findings have driven the search for therapeutic targets the manipulation of which will reprogram TAMs in a manner that will enable them to exhibit pro-immunogenic activities[10,11].

CaMKK2 is a 66-68-kDa kinase that contains unique N- and C-terminal domains, a central Ser/Thr-directed kinase domain, and a complex regulatory domain composed of overlapping autoinhibitory and calmodulin (CaM)-binding regions[12]. The kinase activity of CaMKK2 is auto-inhibited by a sequence located immediately C-terminal to its catalytic domain and this is relieved by a conformational change in the enzyme that occurs upon binding $Ca^{2+}$/CaM. Once activated, CaMKK2 can phosphorylate and increase the activity of CaMKIV and CaMKI, its primary targets. More recently, however, it has been demonstrated that CaMKK2 also phosphorylates 5' AMP-activated protein kinase α (AMPKα) and that silencing of CaMKK2 expression, or inhibition of its catalytic activity, results in a quantitative inhibition of AMPK activity[13,14]. Initially, identified and studied in the brain where it is expressed primarily in the cerebellum, we have recently determined that it is also expressed in the immune system and within prostate cancer epithelial cells[15,16]. Within the immune system CaMKK2 is expressed exclusively in myeloid cells, including hematopoietic progenitors, peritoneal macrophages and bone marrow-derived macrophages. Genetic ablation of CaMKK2 revealed that it plays a significant role in the development and function of myeloid cells and that it regulates their ability to mount inflammatory responses to various stimuli[15,17]. These latter findings prompted us to investigate potential roles for CaMKK2 within immune cells in mammary tumors.

Figure 1:
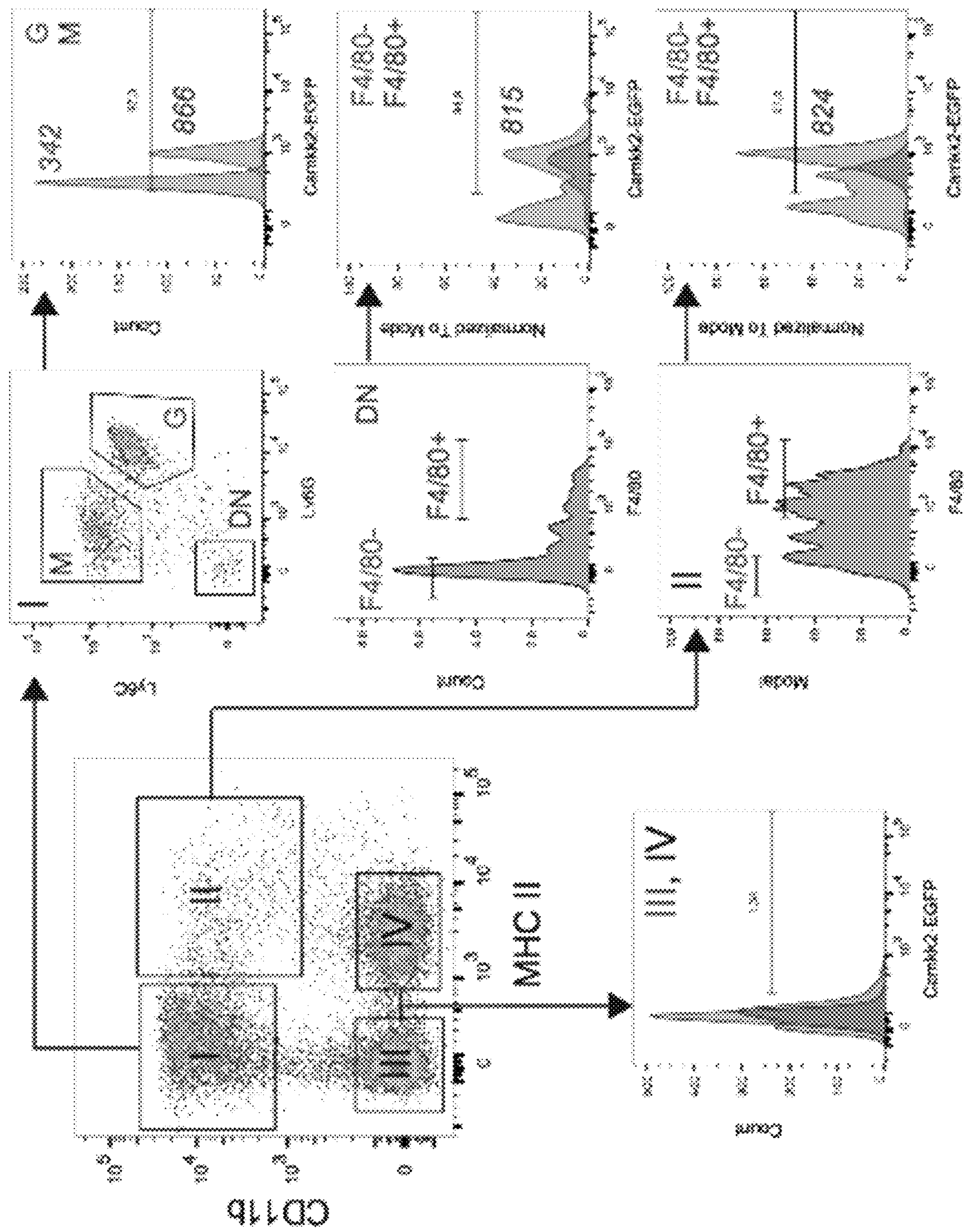
FIG. 1 shows that Camkk2 promoter is active in myeloid cells associated with mammary tumors. E0771 cells ($2\times10^5$ cells/mouse) were inoculated into the mammary fat pad of (Tg)-Camkk2-EGFP reporter mice. Subsequently, tumors were removed, digested with collagenase and DNAase. Single cell suspensions were stained for CD11b, Ly6G, Ly6C, I-A and F4/80. (Upper left) Gating strategy used to identify myeloid (I-II) and non-myeloid (III-IV) cells subsets. (Left) Sub-gating strategy of tumor-associated myeloid subsets. The numbers in the histograms refer to the mean fluorescence intensity (MFI) of the Camkk2-EGFP reporter in the different tumor-associated cell populations. Similar results have been obtained in 6 mammary tumors.

The expression of CaMKK2 within immune cells that infiltrate mammary tumors was assessed in a well-validated model of estrogen receptor-alpha (ERα) positive, luminal breast cancer. Specifically, E0771 breast tumor cells were engrafted into the mammary fat pad of a [Tg(Camkk2-EGFP) BLBL/6J] Camkk2-reporter mouse model[18]. Subsequently, tumors were removed and the immune cell repertoire was analyzed by flow cytometry using the gating strategy outlined in FIG. 1. Robust Camkk2-reporter activity was detected in CD11b+ myeloid cells with minimal activity detectable in CD11b-non-myeloid cells (FIG. 1, gates I-II and gates III-IV). Further analysis of the CD11b+ population, using additional markers to distinguish between different subsets of myeloid cells, revealed substantial Camkk2-reporter activity in tumor associated macrophages ($CD11b^{high}$ $F4/80^{high}$, gate II and gate I/sub-gate DN) that express either high or low levels of the Major Histocompatibility Molecule class II (TAM-$MHCII^{high}$ and TAM-$MHCII^{low}$)[19,20]. The Camkk2-reporter was also active in monocytes/MDSC ($Ly6C^{high}$ Gate I/subgate M) but was barely detectable in granulocytes and eosinophils ($Ly6G^{high}$ compartment; Gate I/subgate G). Considering these data, and our previously published results, we hypothesized that CaMKK2 may impact TAM function and influence the pathobiology of tumors.

Figure 3D:
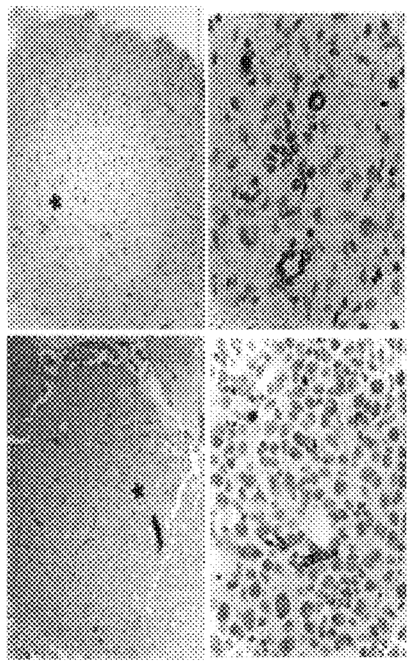
(FIG. 3D) CD31 antibody staining at low and high power optic field images (upper and lower panel, respectively).

The impact of host-cell disruption of CaMKK2 expression on mammary tumor growth was evaluated in murine models of breast cancer. To this end, mammary tumors from MMTV-PyMT mice were removed, diced, and grafted orthotopically into syngeneic Camkk2$^{-/-}$ and WT animals. In this manner it was determined that MMTV-PyMT tumors were unable to grow within the mammary pad of Camkk2$^{-/-}$ mice (FIG. 2A). These studies were repeated in a second model using E0771 mammary cancer cells that were engrafted orthotopically into WT or Camkk2$^{-/-}$ mice. Similar to what was observed in the MMTV-PyMT model, ablation of CaMKK2 in the host impaired the growth of E0771 cell derived tumors (FIG. 2B, FIG. 3A). Pathological analysis of hematoxylin and eosin (H&E) stained tumors indicated that, unlike tumors in WT mice which exhibited key hallmarks of malignancy, a significant fraction of the cells propagated as tumors in Camkk2$^{-/-}$ mice were found to be highly condensed and/or anucleated, features that are attributable to apoptosis and necrosis (FIG. 3B). Masson's trichrome staining revealed significant fibrosis in tumors from Camkk2$^{-/-}$ mice but not in tumors from WT mice (FIG. 3C). Finally, a comparable number of CD31+ endothelial cells were detected in tumors harvested from WT and Camkk2$^{-/-}$ mice, suggesting that CaMKK2 knockdown does not impact neo-angiogenesis in these models of mammary cancer (FIG. 3D).

Figure 4A:
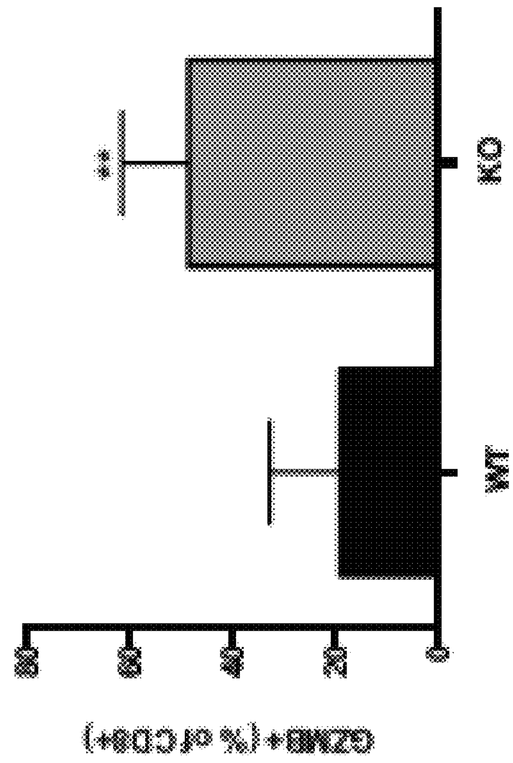
FIGS. 4A-B show tumor associated T-lymphocytes and myeloid cell subsets within E0771 cell derived mammary tumors grown in WT and CaMKK2$^{-/-}$ mice (KO). Tumors from WT and Camkk2−/− mice were harvested digested with collagenase and DNAase. Single cells suspensions were stained for lymphoid and myeloid markers.
Figure 4B:
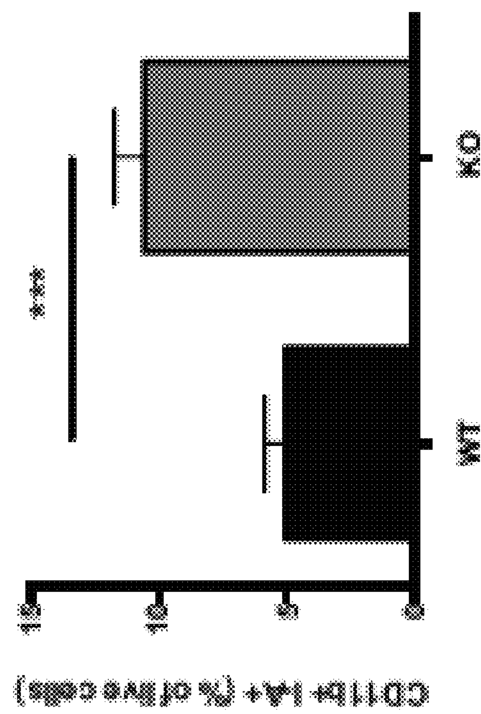

Considering that CaMKK2 is expressed in myeloid cells within tumors, we reasoned that the decreased growth of mammary tumors observed in Camkk2$^{-/-}$ mice may reflect an attenuation of immunosuppressive activities within tumors. Indeed, an immuno-morphometric analysis revealed that a significantly higher number of T-cells (CD3+) and macrophages (F4/80+) accumulated in the non-necrotic areas of tumors removed from Camkk2$^{-/-}$ mice when compared to those isolated from WT animals (FIG. 2C). These findings were confirmed and extended using FACS which indicated that the percentage of CD8+ tumor infiltrating T-lymphocytes (TILs) expressing Granzyme B (GZMB), a marker of effector cytotoxic T-cells, was significantly higher in tumors from Camkk2$^{-/-}$ compared to WT mice (FIG. 4A and FIGS. 5A-B). The percentage of CD8+ TILs having a larger cellular size, a feature that correlates with state of activation, was also significantly higher in tumors from Camkk2$^{-/-}$ mice, when compared to WT (FIG. 5C). The myeloid cell compartment was analyzed using CD11b, F4/80 and MHCII I-A antibodies, according to the gating strategy outlined above. These experiments revealed that TAM MHCII IA$^{high}$ accumulate preferentially in tumors from Camkk2$^{-/-}$ mice (FIGS. 4B and 6). Of note, this subset of macrophages has been identified as TAM showing M1-like features and decreased ability to penetrate hypoxic regions. Interestingly, accumulation of TAM MHCII IA$^{high}$ in tumors also correlates with tumor regression[21,22]. Similarly, in breast cancer the number of CD8+ T-cells in tumors positively correlates with better therapeutic response and prognosis[23,24]. Accordingly, our findings indicate that depletion of CaMKK2 in stromal cells determines major changes in immune cells repertoire accumulating in tumor, suggestive of a more immunogenic microenvironment.

We next evaluated the extent to which the decreased tumor growth in observed Camkk2$^{-/-}$ mice could be attributed to the increased number of cytotoxic T-cells within tumors in these mice. To address this, Camkk2$^{-/-}$ mice were treated with an anti-CD8 antibody or an isotype-matched control as outlined (FIG. 7A). As expected, treatment with the anti-CD8 antibody resulted in a profound depletion of CD8+ T-cells (FIG. 7B), and more importantly CD8 depletion was accompanied by a dramatic increase in tumor growth in the Camkk2$^{-/-}$ background (FIG. 8A). This result confirmed that CD8+ T-cells are responsible, at least in part for the impaired tumor growth observed in Camkk2$^{-/-}$ mice. The observation that Camkk2 is not expressed in CD3+ cells, but is restricted to the myeloid lineage, suggests that the positive effects on CD8+ T-cell induced by CaMKK2 ablation is largely mediated by changes in myeloid cell functions. To test this possibility in a more direct manner, we developed a LysM-Cre-Camkk2$^{fl/fl}$ mouse and demonstrated that the macrophages isolated from this model expressed significantly less CaMKK2 protein than those isolated from LysM Cre Camkk2$^{wt/wt}$ littermates (FIG. 9A-B). As observed in the whole body knockout of CaMKK2, the growth of E0771 cell derived tumors was significantly attenuated when propagated in LysM Cre+ Camkk2$^{fl/fl}$ mice when compared to tumors grown in LysM Cre+ Camkk2$^{wt/wt}$ littermates (FIG. 8B; 9C). We conclude from the results of the studies presented, thus far, that ablation of CaMKK2 in myeloid cells facilitates the accumulation of more immunogenic macrophages, an activity which results in reduced tumor growth.

Figure 11B:
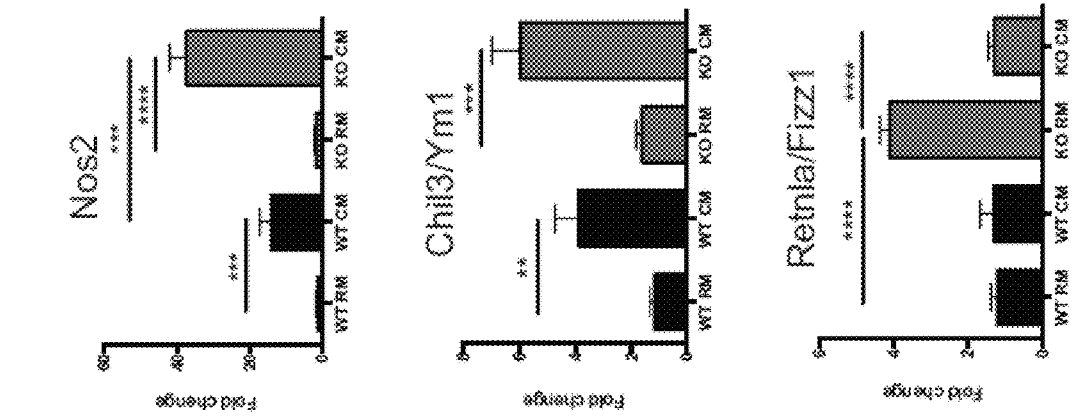
FIG. 11B shows Real time qPCR analysis of M1 and M2 genes (4 biological and 3 technical replicates were analyzed for each genotype).
Figure 11A:
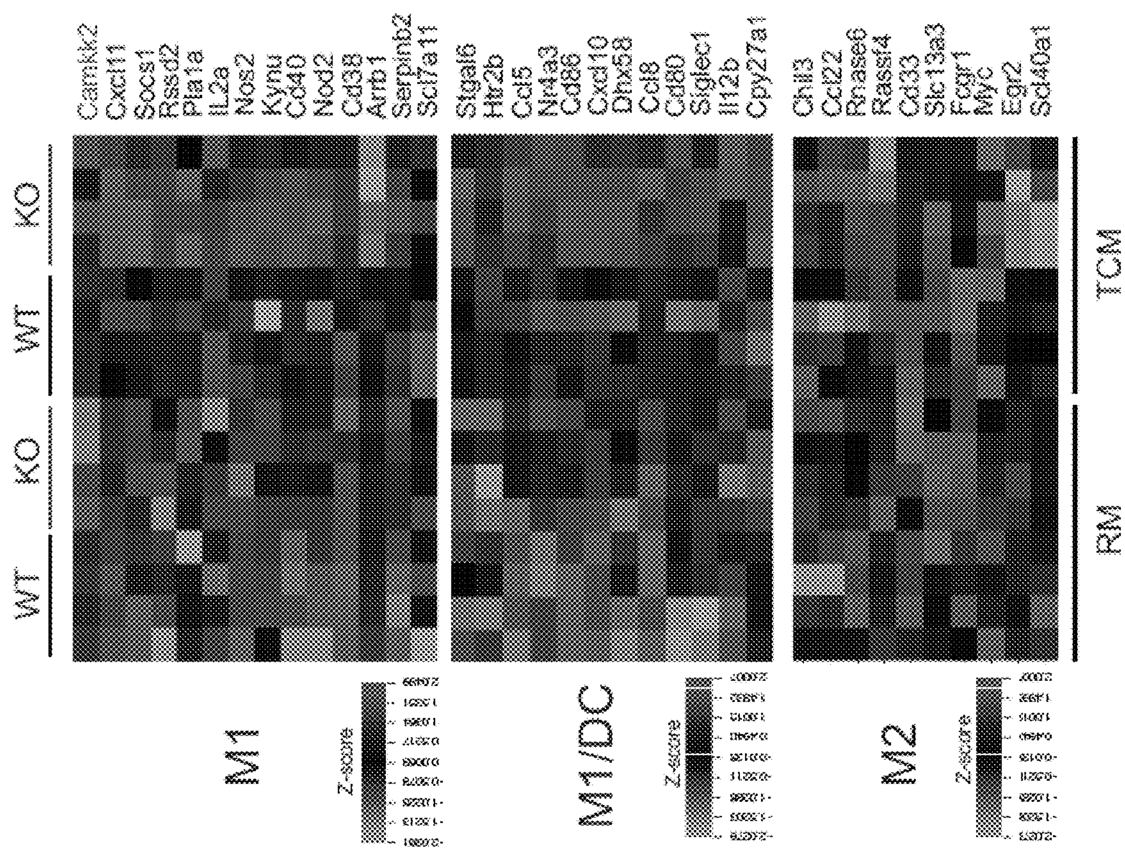
FIG. 11A shows expression profile of genes associated with myeloid cell polarization and differentiation toward M1, dendritic cells (DC) and M2 phenotype. The heat map shows mRNAs changed 2-fold or greater between WT and Camkk2−/− BMDM (P<0.01).
Figure 12B:
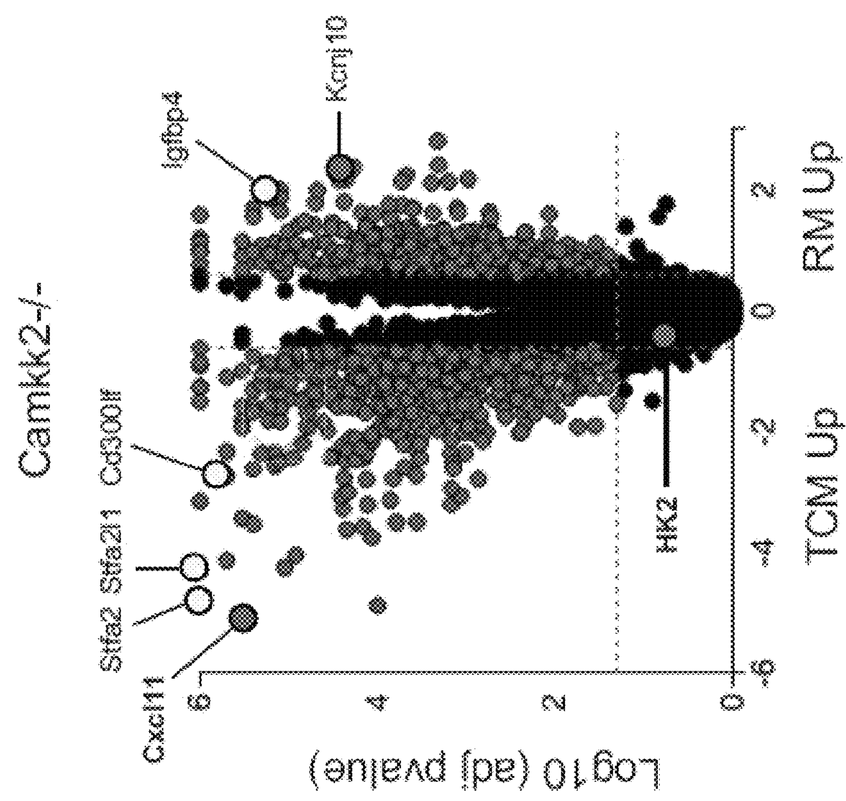
FIG. 12A-B shows Volcano plot of differentially expressed genes (DEGs) in WT and Camkk2−/− BMDM generated in the presence or absence of tumor-conditioned medium (TCM and RM, respectively).
Figure 12A:
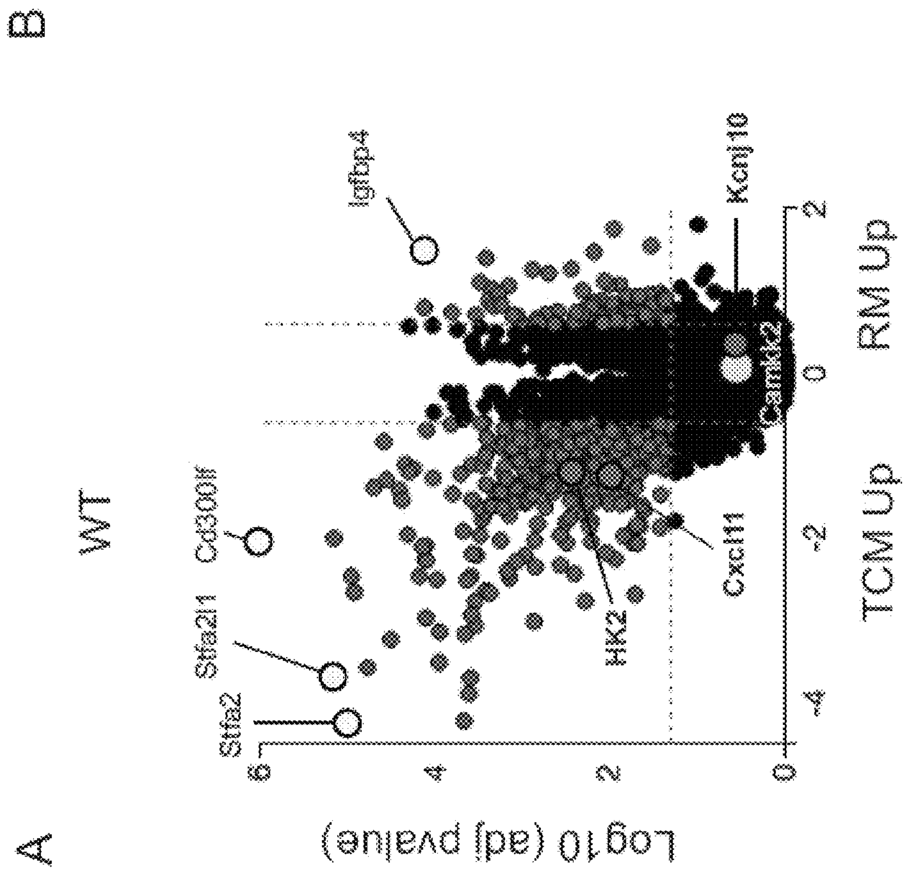
Figures 12C, 12D:
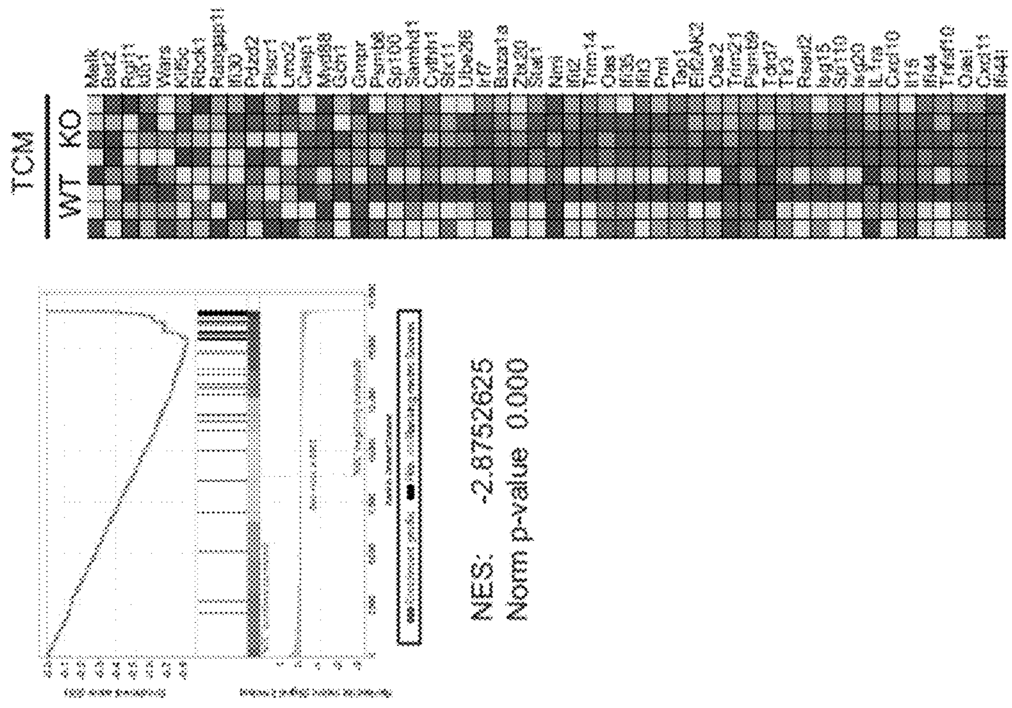
FIG. 12C-D shows gene enrichment analysis of DEGs in WT and Camkk2−/− BMDM generated in the presence of TCM.

Cancer cells secrete factors that can influence myeloid cell differentiation resulting in an increase in the number/activity of TAMs and other myeloid cell subsets that suppress immunogenic responses to tumors[5,11]. Thus, we reasoned that the deletion of CaMKK2 might influence macrophage differentiation and/or activity in a manner that increases their immunogenic phenotype. A quantitative analysis of the immune-regulatory cytokines produced by E0771 cells confirmed, that absent any provocative stimuli, they secreted high levels of VEGF, G-CSF and CCL2 among others (FIGS. 10A and 10B). Next BMDM were isolated from WT and Camkk2$^{-/-}$ mice and differentiated in vitro in the presence of (a) regular media (RM) or (b) E0771 conditioned media (CM). Evaluation of gene expression, signal protein analysis, immune-phenotype and ability to activate syngeneic T-cells was then assessed (FIG. 11-16). An increased expression of genes associated with M1 and DC phenotypes were found in Camkk2−/− BMDM generated in the presence of TCM compared to WT (FIG. 11A and B). The differential responsiveness of Camkk2−/− BMDM to TCM were also confirmed by volcano plot and genes enrichment analysis (FIG. 12). Regardless of the presence of tumor-conditioned medium, CaMKK2 protein was expressed at detectable level in BMDM generated from WT mice. On the contrary, this protein was undetectable in Camkk2−/− BMDM (FIG. 13C). Furthermore, comparable levels of phospho-CaMK1 were detected in BMDM-RM and BMDM-CM, from both WT and Camkk2$^{-/-}$ mice an important finding, which indicates that tumor-derived factors are not increasing all aspects of CaMKK2 signaling in BMDM (FIG. 13C). When analyzed in a similar manner, it was observed that a second target of CaMKK2, AMPKα, was phosphorylated at higher degree in WT BMDM-RM compared to Camkk2$^{-/-}$ BMDM-RM (FIG. 13A). Further, increased AMPKα phosphorylation was observed in WT BMDM-CM compared to BMDM-RM (FIGS. 13A-B), However, the most significant finding was the dramatic decrease in pAMPKα in Camkk2$^{-/-}$ Mac-CM compared to WT BMDM-CM. This is a significant, finding indicating that CaMKK2 is required for coupling signal triggered by tumor-conditioned factors to AMPK activation. This is an important result, given the well-established inhibitory function of AMPK in the mechanisms that control immune-stimulatory properties of macrophages and dendritic cells[25-29].

Figure 16A:
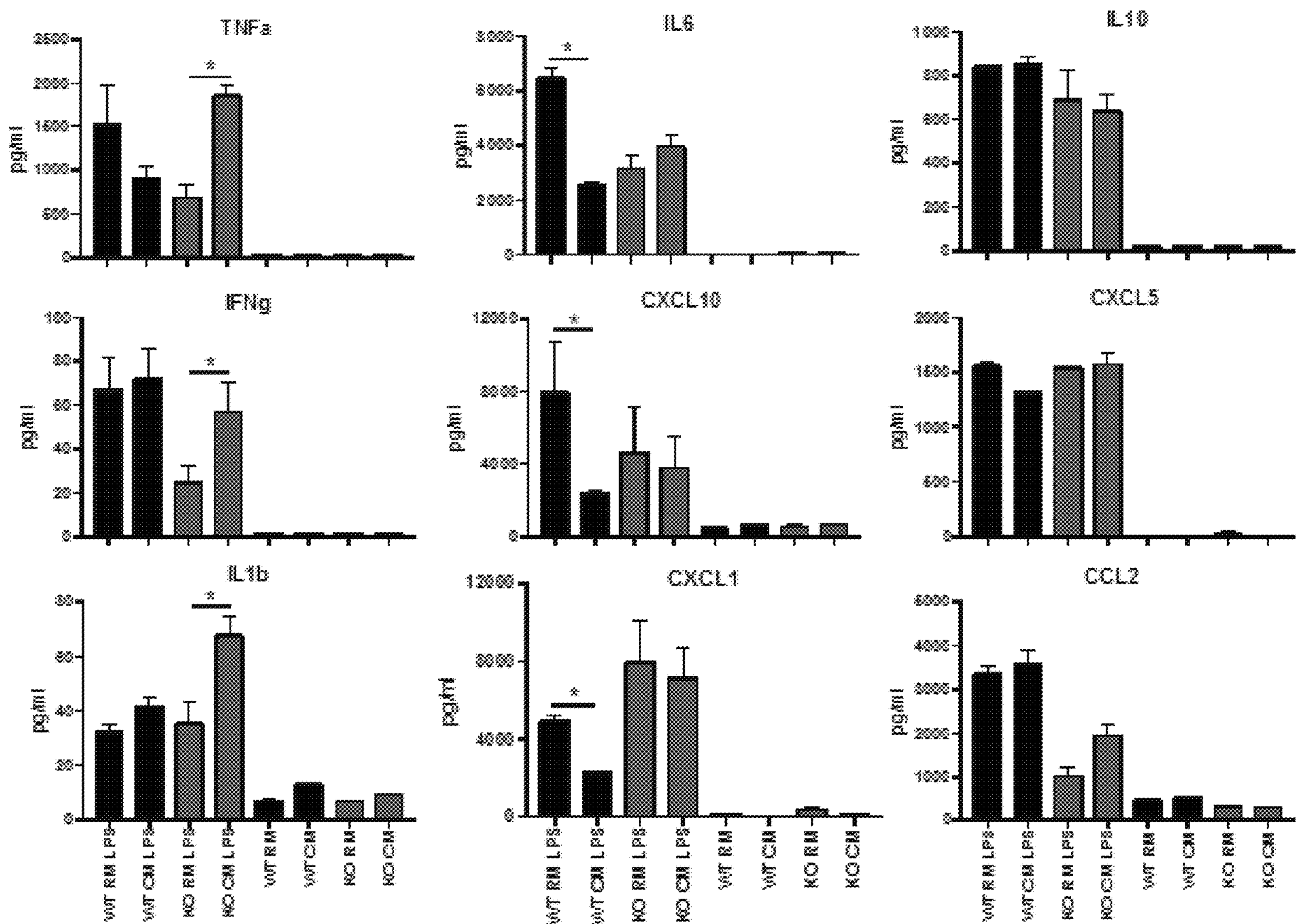
FIG. 16A shows responsiveness to bacterial endotoxin of WT and $Camkk2^{-/-}$ BMDM generated in the presence of regular or E0771-conditioned medium. WT and $Camkk2^{-/-}$ BMDM were generated in the presence of regular or E0771-conditioned medium. After 5-days of culture, cells were collected and grown for an additional 24 h in the presence or absence of lipopolysaccharide (100 ng/ml). Subsequently, cytokine concentrations were measured in cell culture supernatants. Bar graphs report mean±SEM (N=3).
Figure 16B:
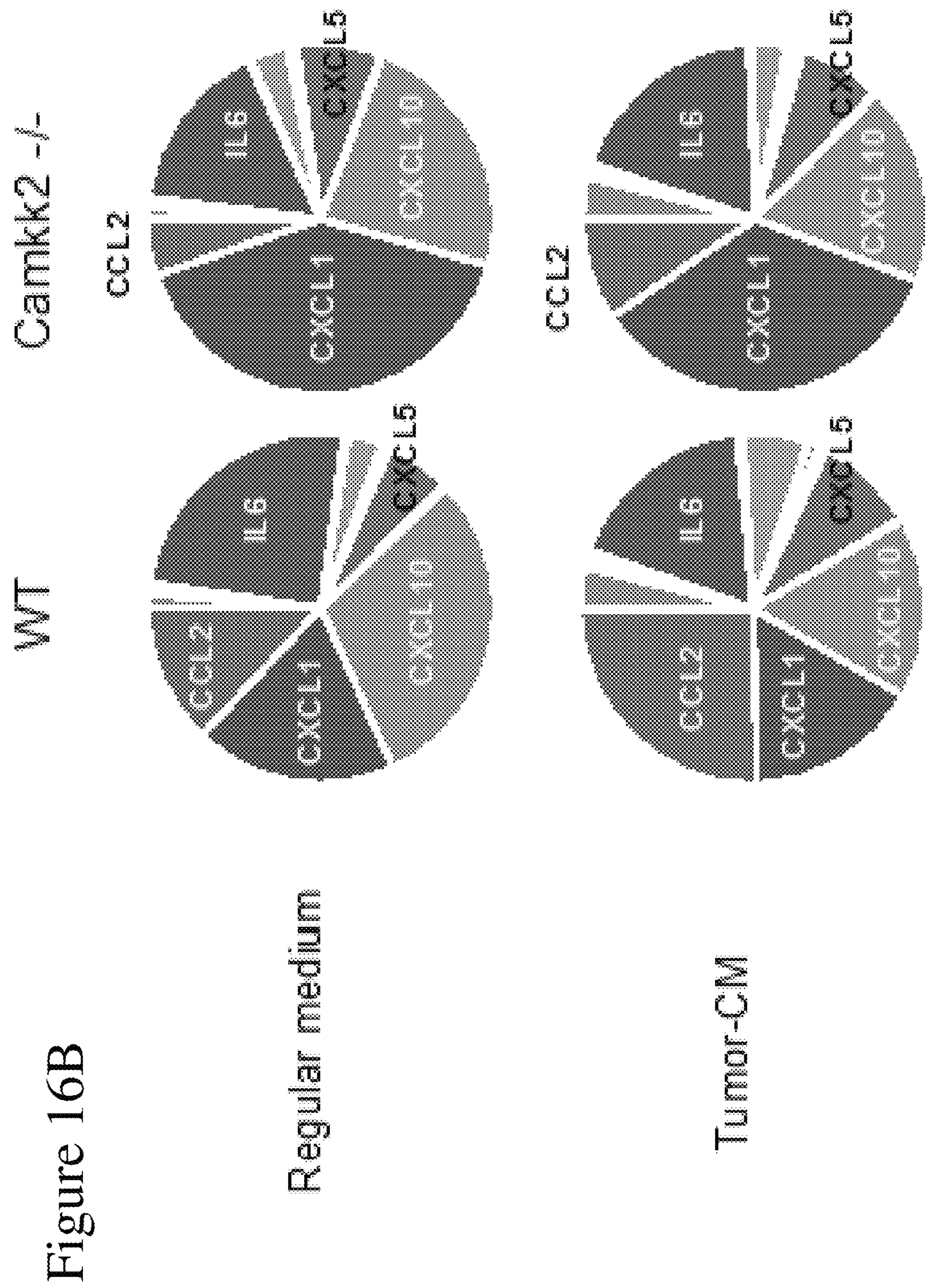
FIG. 16B shows Pie charts showing the fraction of each cytokine in the supernatants from LPS-stimulated macrophages. This experiment was replicated 3 times with similar results. Asterisks refer to *p<0.05.

MHC II and co-stimulatory molecules play key roles in antigen presentation and in T-cell activation. The expression of these molecules also defines functionally distinctive subsets of TAMs with those that express high levels of MHC II and co-stimulatory molecules (CD80, CD86 and CD40) exhibiting increased ability to secrete pro-inflammatory cytokines and support T-cell activation[5,21]. Thus, we analyzed the expression of MHC II, CD86 and CD40 in WT and Camkk2$^{-/-}$ BMDM generated in the presence or absence of CM. Regardless of differentiation medium, Camkk2$^{-/-}$ BMDM expressed significantly higher levels of MHCII I-A compared to WT, and this protein was down-regulated in both cell populations in response to CM (FIG. 14 and FIG. 15A). While CD86 and CD40 were expressed at comparable levels on WT and Camkk2–/– BMDM-RM, higher levels of these co-stimulatory molecules were detected in Camkk2–/– BMDM generated in CM compared to WT (FIG. 15A). Considering this finding we assessed bacterial lipopolysaccharide (LPS, 100 ng/ml) dependent induction of selected cytokines in WT and Camkk2–/– BMDM. As we have reported previously[15], Camkk2 BMDM exhibit decreased sensitivity to LPS, with Camkk2$^{-/-}$ BMDM-RM secreting lower amounts of TNFα, IL-6 and CXCL-10, compared to WT Mac-RM (FIG. 13). Surprisingly, a completely opposite response was observed in BMDM generated in the presence of tumor-conditioned medium, where it was noted that Camkk2–/– BMDM-CM released higher amounts of TNFα, IL-6, CXCL-10, IFNγ and IL1β in response to LPS compared to WT Mac-CM (FIG. 16A-B). This data prompted us to investigate the immune-stimulatory ability of WT and Camkk2–/– BMDM on T-cells. For this study, syngeneic T-cells were isolated from the spleen of WT mice, stained with fluorescent dye (5- (and 6)-carboxyfluorescein diacetate succinimidyl ester (CSFE)), and subsequently co-cultured with BMDM, in the presence of a mitogenic anti-CD3 antibody. A significantly higher amount of IFNγ was detected in T-cell stimulated in the presence of WT BMDM-RM compared to Camkk2$^{-/-}$ BMDM-RM (FIG. 15B-D). Despite this, WT and Camkk2–/– BMDM generated in RM had a comparable ability to stimulate IL-2, CXCL-10 secretion, and induce T-cell proliferation (FIGS. 15B-D). The presence of CM in the differentiation medium impaired the ability of WT BMDM to stimulate IL-2 and IFNγ secretion when co-cultured with T-cells, and this phenomenon was associated to a remarkable decrease in the ability of stimulate proliferation of CD8+ T-cells (FIGS. 15C-D). Importantly, Camkk2$^{-/-}$ BMDM were found to be relatively insensitive to CM-induced immune-suppression and indeed exhibited an increased ability to stimulate cytokine secretion to Camkk2$^{-/-}$ BMDM-RM, as well as to WT BMDM generated in the presence of CM (FIGS. 15C-D). Accordingly, Camkk2$^{-/-}$ BMDM generated in the presence or absence of CM have comparable ability to stimulate the proliferation of CD8+ T-cells (FIGS. 15C-D). Together these findings highlight the importance of CaMKK2 in the differentiation of TAMs, confirming the key role of this protein in the immune-regulatory mechanisms triggered by tumor-derived factors in macrophage. Importantly, these results implicate that the pharmaceutical inhibitors of CaMKK2 may have therapeutic utility in breast cancer by modulating the tumor microenvironment in a manner that increases anti-tumor immune responses.

Figure 17A:
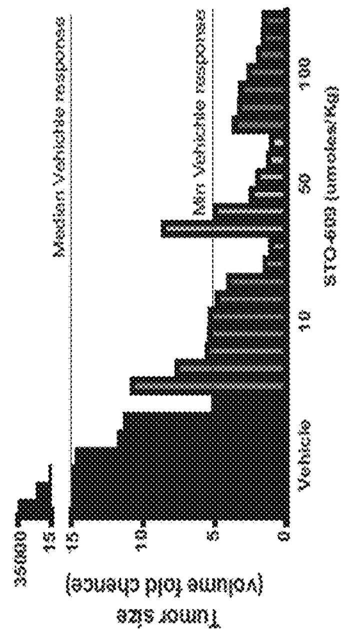
FIG. 17A shows waterfall-plot reports fold change in tumor volume of mice bearing MMTV PyMT mammary tumor being treated daily with vehicle or indicated dose of STO-609, a CaMKK2 inhibitor.
Figure 17B:
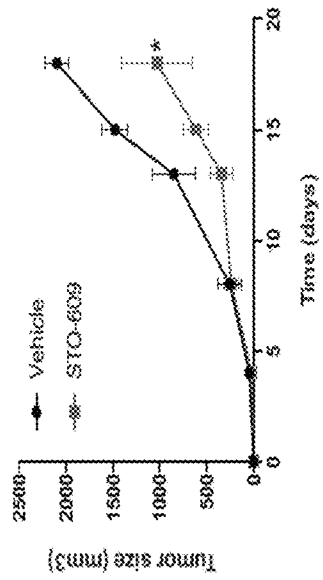
FIG. 17B shows E0771 ($4\times10^5$) cells were orthotopically grafted into syngeneic wildtype mice, that were treated 3-times/week with vehicle or STO-609 (IP, 50 moles/Kg body weight), and subsequently tumor volume measured (mean+/−SEM; N=6 in each group).
Figure 17C:
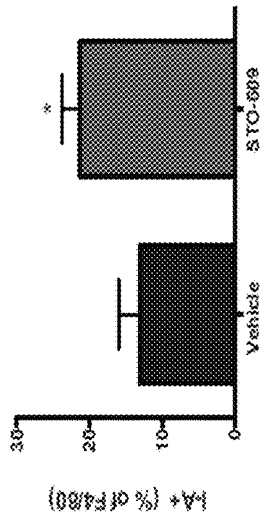
FIGS. 17C-D shows tumor associated myeloid cells and T-lymphocytes subsets within E0771 mammary tumors treated with STO-609 or vehicle. Tumors were removed, digested with collagenase and DNAase. Single cells suspensions were stained for myeloid and lymphoid markers. Treatment with STO-609 resulted in accumulation of F4/80+I-A+ myeloid cells and CD8+ T-cells (FIGS. 17C and 17D, respectively).
Figure 17D:
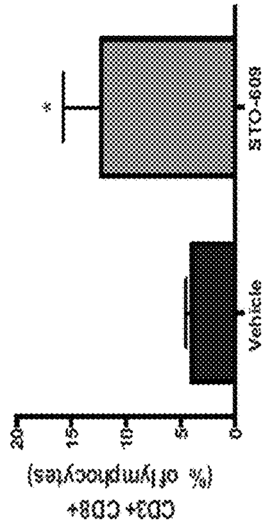
Figure 17E:
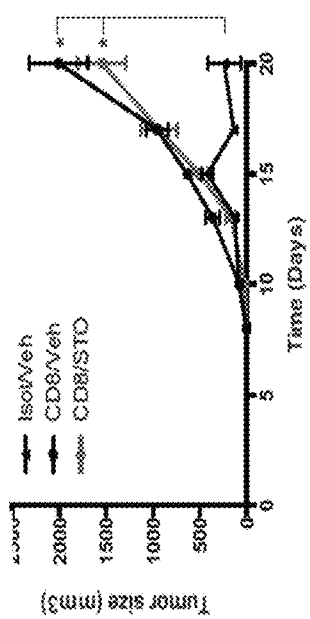
FIG. 17E shows STO-609 does not affect mammary tumor growth in CD8+-T-cells depleted $Camkk2^{-/-}$ mice. $Camkk2^{-/-}$ mice were treated with anti-CD8 or control isotype. Subsequently, E0771 cells were orthotopically grafted, and mice treated with STO-609 or vehicle. Tumors volumes were measured (mean+/−SEM; N=7 in each group). Asterisks refer to p<0.05, 0.01, 0.005 and 0.001 (*, , * and ****, respectively).

STO-609 is a CaMKK2 inhibitor whose effectiveness has already been demonstrated in animal models of prostate and liver cancer and was used here to evaluate its impact on breast tumor growth and on the tumor microenvironment[30,31]. An initial dose ranging study was performed in the MMTV-PyMT mouse model of luminal cancer where it was demonstrated that tumor growth was inhibited in dose responsive manner (FIG. 17A). The antitumor activity of STO-609 was also observed in the orthotopic E0771 model (FIG. 17B) and in the 4T1 and Met 1 models of mammary cancer (FIGS. 18A and 18B). We corroborated these findings using N28464-13-A1, a recently reported CaMKK2 inhibitor of a different chemical class (FIG. 18C-D). Interestingly, we found that treatment with STO-609 induced major changes in tumor microenvironment promoting accumulation of MHCII I-A$^{high}$ macrophages, CD4+, CD8+ and NK-T cells in E0771 tumors. (FIGS. 17B-C; FIG. 18). These findings are consistent with the results of the genetic studies described above and together they suggests that a major effect of CaMKK2 expression in macrophages is limiting the number of MHCII I-A$^{high}$ macrophages and T-cells in tumors (FIG. 19). We ruled out the possibility that STO-609 was exhibiting its prevalent antitumor activity through direct actions on tumor cells by showing that depletion of CD8+ T-cells allowed the growth of E0771 tumors in CamKK2–/– mice, and under these conditions STO-609 treatment was without effect (FIG. 17E).

Figure 20A:
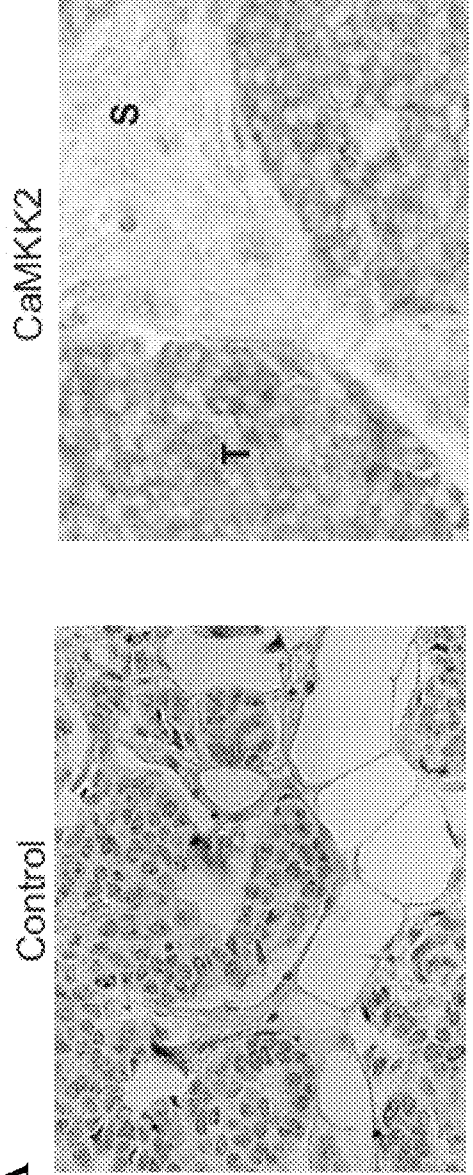
FIG. 20A shows the expression of CaMKK2 in human breast cancer and macrophages. CaMKK2 is highly expressed in tumor cells (T) and in some stromal cells (S) of malignant mammary tissue.
Figure 20B:
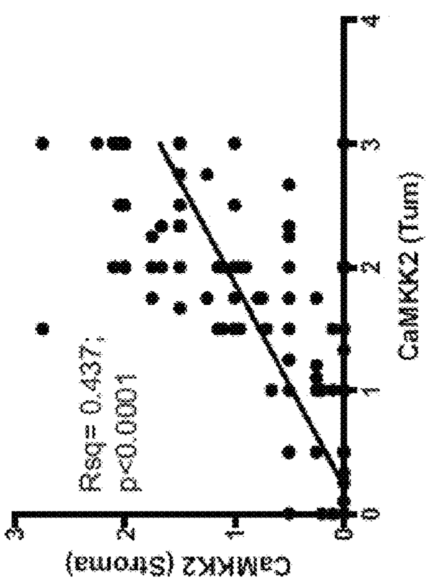
FIG. 20B shows CaMKK2 staining intensity is correlated between cancer and stromal cells of the same human breast tumors.
Figure 20C:
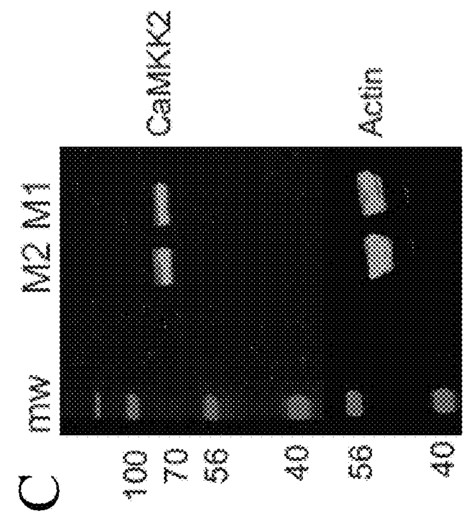
FIG. 20C shows CaMKK2 is expressed in human monocyte-derived macrophages. Immunoblot of M1 and M2 polarized macrophages generated from adherent mononuclear cells isolated from peripheral blood of healthy donors (PromoCell Kit®). The experiment has been replicated using 3 independent samples.
Figure 21:
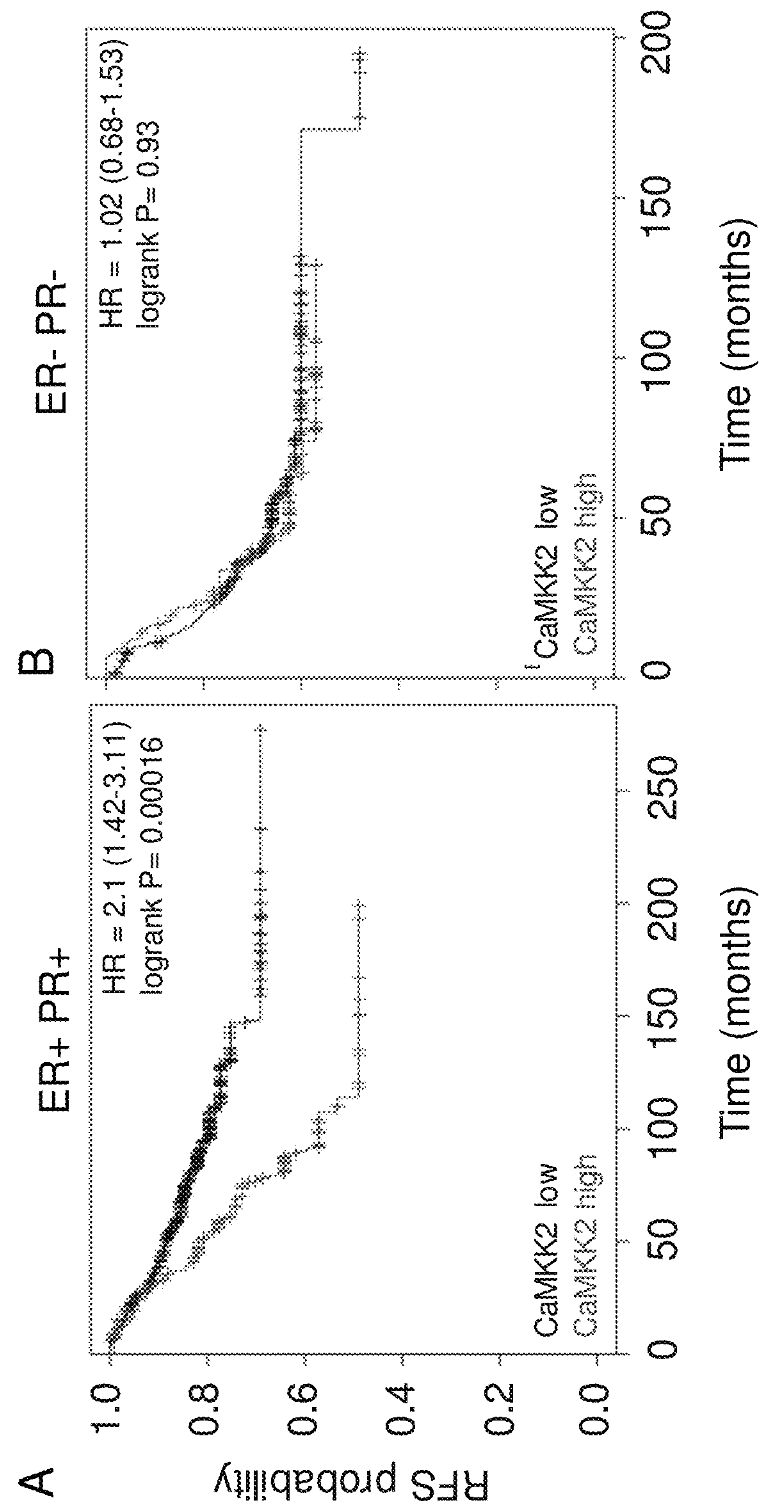
FIG. 21 shows increased expression of CaMKK2 negatively correlates with prognosis in patients with ER+ PR+ breast cancer. Kaplan-Meier plot of relapse-free survival of estrogen and progesterone receptors positive (ER+ and PR+, respectively) breast cancer patients stratified by upper quartile tumor CAMKK2 expression in the KM-Plotter database. Log-rank test P-value is displayed.

Our studies have defined a role for CaMKK2 in regulating the tumor microenvironment in animal models of breast cancer. To probe the potential significance of these observations in humans we undertook an analysis of CaMKK2 expression in well-curated breast cancer tissue arrays. Using two different datasets that contained primary human breast cancer samples, we found CaMKK2 to be expressed at variable levels in cancer cells, as well as in certain stromal cells (FIG. 20). Of note, we demonstrate that CaMKk2 is expressed in human macrophages generated in vitro by circulating monocytes (FIG. 20C). In the Vienna data set, containing 47 samples, CaMKK2 expression significantly correlated with tumor molecular type, and higher expression of CaMKK2 (staining intensity >2) was significantly associated with the most aggressive triple-negative (TN) tumors (Table 2). This data was confirmed in the Roswell, dataset that includes 68 samples. The analysis of data from combined datasets clearly indicated that overexpression of CaMKK2 increases the likelihood of having TN tumors (Table 2 and 3). On the contrary, overexpression of CaMKK2 did not correlate with tumor grade (Table 4). Finally, we verified the prognostic significance of CaMKK2 expression using the publically available KM-plot dataset[32], that includes gene expression microarray from more than 4000 breast cancer specimens. Using this resource, we were able to demonstrate that in the most common estrogen receptor and progesterone receptor positive breast cancers, higher expression of CaMKK2 negatively correlated with prognosis (FIG. 21).

TABLE 2

CaMKK2 expression by molecular breast cancer subtype. Immunohistochemical analysis of CaMKK2 expression in human breast cancer tissue microarrays, from two independent datasets (Vienna and Roswell Park Cancer Institute, RCPI). CaMKK2 expression was determined to be low or high, and correlated with molecular subtype: triple negative, luminal A and luminal B (TN, LNA and LNB, respectively). Fisher's exact test was used to determine P-values for the likelihood of association.

| | Vienna[1] | | | | RPCI | | | | Combined | | | |
|---|---|---|---|---|---|---|---|---|---|---|---|---|
| CaMKK2 | N | LA | LB | TN | N | LA | LB | TN | N | LA | LB | TN |
| Low | 32 | 75% | 9% | 16% | 54 | 65% | 19% | 16% | 86 | 69% | 15% | 16% |
| High | 15 | 40% | 20% | 40% | 14 | 43% | 7% | 50% | 29 | 41% | 14% | 45% |
| P value[2] | | 0.05463 | | | | 0.00002 | | | | 0.00784 | | |
| OR[3] | 0.2 | nd | | ns | ns | nd | | 5.0 | 0.3 | nd | | 4.1 |
| P value[4] | 0.0241 | nd | | ns | ns | nd | | 0.0129 | 0.0107 | nd | | 0.0026 |

[1]Dataset
[2]Fisher's exact test P value
[3]Odds Ratio
[4]Odds Ratio P value

TABLE 3

CaMKK2 expression by hormone receptor and HER2 status. Immunohistochemical analysis of CaMKK2 expression in human breast cancer tissue microarrays. CaMKK2 expression was determined to be low or high and correlated with the expression of estrogen receptor (ER), progesterone receptor (PR) and human epidermal growth factor receptor 2 (HER2). Values refer to data from two combined breast cancer cohorts (Vienna and Roswell Park Cancer Institute, RCPI). Fisher's exact test was used to determine P-values for the likelihood of association. Ordinal logistic regression was used to estimate the odds ratio. Not significant ($p > 0.05$) and not determined values are indicated as ns and nd, respectively.

| | | ER | | PR | | HER2 | |
|---|---|---|---|---|---|---|---|
| CaMKK2 | N | Pos | Neg | Pos | Neg | Pos | Neg |
| Low | 86 | 81% | 19% | 67% | 33% | 7% | 95% |
| High | 29 | 55% | 45% | 48% | 52% | 10% | 90% |
| P value | | 0.00634 | | 0.05340 | | ns | |
| OR[1] | | 3.5 | | 2.2 | | nd | |
| P value[2] | | 0.0064 | | ns | | nd | |

[1]Odds Ratio
[2]Odds Ratio P value

TABLE 4

CaMKK2 expression by tumor grade. Immunohistochemical analysis of CaMKK2 expression in human breast cancer tissue microarrays, from two independent datasets (Vienna and Roswell Park Cancer Institute, RCPI). CaMKK2 expression was determined to be low or high, and correlated with combined tumor grade (1, 2 and 3, respectively). A Fisher's exact test was used to determine P-values for the likelihood of association. Not significant ($p > 0.05$) and not determined values are indicated as ns and nd, respectively.

| | Vienna | | | | RPCI | | | | Combined | | | |
|---|---|---|---|---|---|---|---|---|---|---|---|---|
| CaMKK2 | N | 1 | 2 | 3 | N | 1 | 2 | 3 | N | 1 | 2 | 3 |
| Low | 32 | 22% | 63% | 15% | 54 | 2% | 13% | 85% | 86 | 9% | 31% | 60% |
| High | 15 | 7% | 53% | 40% | 14 | 7% | 7% | 86% | 29 | 7% | 31% | 62% |
| P value | | | ns | | | | ns | | | | ns | |

In aggregate, our findings pinpoint CaMKK2 as an important myeloid-specific molecular hub that convey signals controlling activation and differentiation of macrophages in the tumor microenvironment. The expression of CaMKK2 in human breast cancer, combined with the effectiveness of CaMKK2 inhibitors to reprogram tumor microenvironment, uncover CaMKK2 as a novel macrophage-specific immune checkpoint, the inhibition of which may have utility in the immunotherapy of breast cancer.

REFERENCES

1. Green M F, Anderson K A, Means A R. Characterization of the CaMKKbeta-AMPK signaling complex. *Cellular signalling.* 2011; 23(12):2005-2012.

2. Noy R, Pollard J W. Tumor-associated macrophages: from mechanisms to therapy. *Immunity.* 2014; 41(1):49-61.
3. Qian B Z, Pollard J W. Macrophage diversity enhances tumor progression and metastasis. *Cell.* 2010; 141(1):39-51.
4. Ruffell B, Chang-Strachan D, Chan V, et al. Macrophage IL-10 blocks CD8+ T cell-dependent responses to chemotherapy by suppressing IL-12 expression in intratumoral dendritic cells. *Cancer Cell.* 2014; 26(5):623-637.
5. Ugel S, De Sanctis F, Mandruzzato S, Bronte V. Tumor-induced myeloid deviation: when myeloid-derived suppressor cells meet tumor-associated macrophages. *J Clin Invest.* 2015; 125(9):3365-3376.
6. Solinas G, Germano G, Mantovani A, Allavena P. Tumor-associated macrophages (TAM) as major players of the cancer-related inflammation. *J Leukoc Biol.* 2009; 86(5): 1065-1073.
7. Leek R D, Lewis C E, Whitehouse R, Greenall M, Clarke J, Harris A L. Association of macrophage infiltration with angiogenesis and prognosis in invasive breast carcinoma. *Cancer Res.* 1996; 56(20):4625-4629.
8. Medrek C, Pontén F, Jirstrom K, Leandersson K. The presence of tumor associated macrophages in tumor stroma as a prognostic marker for breast cancer patients. *BMC Cancer.* 2012; 12:306.
9. Mahmoud S M, Lee A H, Paish E C, Macmillan R D, Ellis I O, Green A R. Tumour-infiltrating macrophages and clinical outcome in breast cancer. *J Clin Pathol.* 2012; 65(2):159-163.
10. Williams C B, Yeh E S, Soloff A C. Tumor-associated macrophages: unwitting accomplices in breast cancer malignancy. *NPJ Breast Cancer.* 2016; 2.
11. Schreiber R D, Old L J, Smyth M J. Cancer immunoediting: integrating immunity's roles in cancer suppression and promotion. *Science.* 2011; 331(6024):1565-1570.
12. Racioppi L, Means A R. Calcium/calmodulin-dependent protein kinase kinase 2: roles in signaling and pathophysiology. *J Biol Chem.* 2012; 287(38):31658-31665.
13. Hawley S A, Pan D A, Mustard K J, et al. Calmodulin-dependent protein kinase kinase-beta is an alternative upstream kinase for AMP-activated protein kinase. *Cell metabolism.* 2005; 2(1):9-19.
14. Woods A, Dickerson K, Heath R, et al. Ca2+/calmodulin-dependent protein kinase kinase-beta acts upstream of AMP-activated protein kinase in mammalian cells. *Cell metabolism.* 2005; 2(1):21-33.
15. Racioppi L, Noeldner P K, Lin F, Arvai S, Means A R. Calcium/calmodulin-dependent protein kinase kinase 2 regulates macrophage-mediated inflammatory responses. *J Biol Chem.* 2012; 287(14):11579-11591.
16. Frigo D E, Howe M K, Wittmann B M, et al. CaM kinase kinase beta-mediated activation of the growth regulatory kinase AMPK is required for androgen-dependent migration of prostate cancer cells. *Cancer research.* 2011; 71(2):528-537.
17. Teng E C, Racioppi L, Means A R. A cell-intrinsic role for CaMKK2 in granulocyte lineage commitment and differentiation. *J Leukoc Biol.* 2011; 90(5):897-909.
18. Gong S, Zheng C, Doughty M L, et al. A gene expression atlas of the central nervous system based on bacterial artificial chromosomes. *Nature.* 2003; 425(6961):917-925.
19. Movahedi K, Laoui D, Gysemans C, et al. Different tumor microenvironments contain functionally distinct subsets of macrophages derived from Ly6C(high) monocytes. *Cancer Res.* 2010; 70(14):5728-5739.
20. Laoui D, Van Overmeire E, Di Conza G, et al. Tumor hypoxia does not drive differentiation of tumor-associated macrophages but rather fine-tunes the M2-like macrophage population. *Cancer Res.* 2014; 74(1):24-30.
21. Wang B, Li Q, Qin L, Zhao S, Wang J, Chen X. Transition of tumor-associated macrophages from MHC class II(hi) to MHC class II(low) mediates tumor progression in mice. *BMC Immunol.* 2011; 12:43.
22. Georgoudaki A M, Prokopec K E, Boura V F, et al. Reprogramming Tumor-Associated Macrophages by Antibody Targeting Inhibits Cancer Progression and Metastasis. *Cell Rep.* 2016; 15(9):2000-2011.
23. DeNardo D G, Brennan D J, Rexhepaj E, et al. Leukocyte complexity predicts breast cancer survival and functionally regulates response to chemotherapy. *Cancer Discov.* 2011; 1(1):54-67.
24. Wang K, Xu J, Zhang T, Xue D. Tumor-infiltrating lymphocytes in breast cancer predict the response to chemotherapy and survival outcome: A meta-analysis. *Oncotarget.* 2016.
25. Sag D, Carling D, Stout R D, Suttles J. Adenosine 5'-monophosphate-activated protein kinase promotes macrophage polarization to an anti-inflammatory functional phenotype. *Journal of immunology.* 2008; 181(12): 8633-8641.
26. Yang Z, Kahn B B, Shi H, Xue B Z. Macrophage alpha1 AMP-activated protein kinase (alpha1 AMPK) antagonizes fatty acid-induced inflammation through SIRT1. *The Journal of biological chemistry.* 2010; 285(25): 19051-19059.
27. Galic S, Fullerton M D, Schertzer J D, et al. Hematopoietic AMPK beta1 reduces mouse adipose tissue macrophage inflammation and insulin resistance in obesity. *The Journal of clinical investigation.* 2011.
28. Mounier R, Théret M, Arnold L, et al. AMPKα1 regulates macrophage skewing at the time of resolution of inflammation during skeletal muscle regeneration. *Cell Metab.* 2013; 18(2):251-264.
29. Carroll K C, Viollet B, Suttles J. AMPKα1 deficiency amplifies proinflammatory myeloid APC activity and CD40 signaling. *J Leukoc Biol.* 2013; 94(6):1113-1121.
30. Massie C E, Lynch A, Ramos-Montoya A, et al. The androgen receptor fuels prostate cancer by regulating central metabolism and biosynthesis. *The EMBO journal.* 2011; 30(13):2719-2733.
31. Lin F, Marcelo K L, Rajapakshe K, et al. The camKK2/camKIV relay is an essential regulator of hepatic cancer. *Hepatology.* 2015; 62(2):505-520.
32. Gyorffy B, Lanczky A, Eklund A C, et al. An online survival analysis tool to rapidly assess the effect of 22,277 genes on breast cancer prognosis using microarray data of 1,809 patients. *Breast Cancer Res Treat.* 2010; 123(3): 725-731.
33. Schmid M C, Varner J A. Myeloid cells in the tumor microenvironment: modulation of tumor angiogenesis and tumor inflammation. *J Oncol.* 2010; 2010:201026.
34. Bronte V. Myeloid-derived suppressor cells in inflammation: uncovering cell subsets with enhanced immunosuppressive functions. *Eur J Immunol.* 2009; 39(10): 2670-2672.
35. Gabrilovich D I, Nagaraj S. Myeloid-derived suppressor cells as regulators of the immune system. *Nat Rev Immunol.* 2009; 9(3):162-174.
36. Coussens L M, Zitvogel L, Palucka A K. Neutralizing tumor-promoting chronic inflammation: a magic bullet? *Science.* 2013; 339(6117):286-291.

37. Gabrilovich D I, Bronte V, Chen S H, et al. The terminology issue for myeloid-derived suppressor cells. *Cancer Res.* 2007; 67(1):425; author reply 426.

38. Kumar V, Cheng P, Condamine T, et al. CD45 Phosphatase Inhibits STAT3 Transcription Factor Activity in Myeloid Cells and Promotes Tumor-Associated Macrophage Differentiation. *Immunity.* 2016; 44(2):303-315.

39. Schafer C C, Wang Y, Hough K P, et al. Indoleamine 2,3-dioxygenase regulates anti-tumor immunity in lung cancer by metabolic reprogramming of immune cells in the tumor microenvironment. *Oncotarget.* 2016; 7(46): 75407-75424.

40. Hardie D G. AMPK—sensing energy while talking to other signaling pathways. *Cell Metab.* 2014; 20(6):939-952.

Example 2: Inhibition of Calcium/Calmodulin Dependent Protein Kinase Kinase 2 (CaMKK2) Prevents Accumulation of Myeloid-Derived Suppressor Cell (MDSC) and Tumor Progression Myeloid cells play an important role in mediating tumor immunity. Under tumor condition, the normal development and maturation of myeloid cells were suppressed, resulted in impaired function of antigen-presenting cells (APCs) and accumulation of myeloid-derived suppressor cells (MDSCs). In this study, we showed that Calcium/Calmodulin dependent protein kinase kinase 2 (CaMKK2), a crucial kinase in calcium signaling cascade, regulated myeloid cell differentiation under lymphoma condition. Ablating CaMKK2 limited MDSC accumulation while promoted myeloid cells differentiation towards mature macrophages and dendritic cells. This effect was regulated by inhibiting AMPK phosphorylation, resulting in a reduced oxidative metabolism and increased ROS level. The increased ROS level increased CaMKK2 KO MDSCs susceptibility to oxidation stress, and the tendency to differentiate into mature dendritic cells. Thus, inhibiting CaMKK2 provided a new perspective to specifically regulate AMPK in myeloid cells to facilitate myeloid cells maturation, thus enhanced anti-lymphoma immunity.

Myeloid cells are a collection of hematopoietic cells differentiated from the common myeloid progenitors through myelopoiesis. In tumor condition, cancer cells induce an inflammatory and immune suppressive environment to impair the normal maturation and function of myeloid cells, resulting in the accumulation of myeloid-derived suppressor cells (MDSCs) that impaired T-cell function and sustained tumor progression[33-35 36].

MDSCs are immature myeloid cells with various stages of differentiation. MDSCs accumulation is reported in different pathological conditions including inflammation, autoimmune diseases, transplantation, and cancer[37]. Despite the complexity of heterogeneous composition, MDSCs are generally categorized into monocytic MDSC (M-MDSCs) and polymorphonuclear MDSCs (PMN-MDSCs) based on their morphology and phenotypes. In human, M-MDSCs are CD14+HLA-DR$^{-/lo}$ while PMN-MDSCs are marked as CD14-CD11b+CD33+CD15+. In mice, MDSCs are broadly identified as CD11b+Gr1+ cells, and categorized further according to Gr-1 subgroup markers as monocytic MDSC (CD11b+Ly6C$^{high}$Ly6G−, M-MDSC) and polymorphonuclear MDSC (CD11b+Ly6C$^{lo}$Ly6G+, PMN-MDSC). While PMN-MDSCs mainly suppress antigen-specific T-cell response by reactive oxygen species (ROS), M-MDSC can suppress both antigen-specific and non-specific T-cell response by generating nitric oxide (NO) and suppressive cytokines. MDSCs can also suppress the immune function of NK cells and dendritic cells and induce regulatory T cells (Treg) by expressing arginase (Arg1), inducible NOS (iNOS), COX, and TH2 cytokines, thus generating an inflammatory environment that facilitates tumor growth. The MDSCs accumulation and suppressive function have been confirmed in human patients and animal models with different cancers, associating with the malignancy progression and poor survival.

Among MDSCs, M-MDSCs can traffic to tumors and differentiate into PMN-MDSCs, tumor associated macrophage (TAM), and dendritic cells under certain chemokine stimulation. In tumor microenvironment, the polarization of TAM and maturation of dendritic cells are interfered, resulting in the accumulation of pro-tumor TAM and immature dendritic cells that prone to suppress anti-tumor immunity. Several molecular pathways including STAT3 and AMPK, have been reported to regulate the generation and differentiation of MDSCs[38,39]. However, since these signaling pathways are commonly used in different vital organs, how to specifically target myeloid cells differentiation in tumor environment to improve anti-tumor immunity is still unsolved. In this study, we revealed Calcium/Calmodulin ($Ca^{2+}$/CaM) dependent protein kinase kinase 2 (CaMKK2) as a good candidate to specifically manipulate myeloid cell differentiation.

CaMKK2 is a crucial kinase in the calcium signaling cascade[12]. Once bound to the $Ca^{2+}$/CaM complex, CaMKK2 can be activated through conformational change, and further phosphorylate the down stream targets including CaMKI, CaMKIV, and 5' AMP-activated kinase (AMPK). AMPK known as a ubiquitous energy sensor in all tissues, is a direct and physiological substrate of CaMKK2. The activation of AMPK switches on catabolic pathways including glucose uptake and glycolysis, fatty acid uptake and oxidation, mitochondrial biogenesis and autophagy, while switching off biosynthetic pathways. Thus, AMPK regulates not only the cellular energy metabolism but also the cell growth and differentiation by phosphorylating some crucial pathways including mTOR, acetyl CoA carboxylase (ACC), histone deacetylase (HDAC), peroxisome proliferator-activated receptor-γ coactivator 1α (PGC1 α). As the upstream kinase of AMPK, CaMKK2 plays a crucial role in regulating cell metabolism and cell fate[40].

CaMKK2 is exclusively expressed in the hematopoietic stem cells, progenitors, and some myeloid cells including macrophages and monocytes outside of the brain. CaMKK2 has been proven for the intrinsic role in maintaining the stemness of the progenitors, and restricting the differentiation of the progenitors towards mature cells during hematopoiesis, adipogenesis, and muscle development. In hematopoiesis in particular, CaMKK2 expression is high in myeloid progenitors, and gradually decreased during cell differentiation. CaMKK2 deficiency promotes cell autonomous granulocyte commitment and differentiation from myeloid progenitors. CaMKK2 also regulates cancer progression in different cancer cell lines. However, in these previous studies, the role of CaMKK2 was only studied within the cancer cells. How CaMKK2 impacts tumor microenvironment and interferes the tumor immunity is still unknown.

In this study, we used E.G7 murine lymphoma cells as the cancer model, and investigated the effect of CaMKK2 on myeloid cells differentiation under lymphoma condition. We found that E.G7 tumor growth was inhibited in CaMKK2 knock-out (KO) mice, while this inhibition could be reversed by depleting CD8 cells or infusing MDSCs in vivo.

In both in vivo and in vitro experiments, CaMKK2 was expressed in MDSCs. Abating CaMKK2 limited MDSC accumulation but promoted myeloid differentiation towards mature dendritic cells, thus enhanced anti-lymphoma immunity. In CaMKK2 deficient MDSCs, AMPK phosphorylation was inhibited, leading to the metabolic changes of mitochondria and the subsequently increased ROS accumulation. The increased level of ROS prompted MDSC differentiation towards dendritic cells, and also increased MDSC apoptosis under oxidative stress. In conclusion, we proved that CaMKK2 played a crucial role in regulating MDSC development in lymphoma condition. CaMKK2 as a negative regulator of anti-tumor immunity but strictly expressed in myeloid cells makes it a potential specific target for cancer therapy.

Results

CaMKK2 is Expressed in MDSC In Vivo.

In previous publications, CaMKK2 was reported to be expressed in HSCs and myeloid progenitors and macrophages. To verify if CaMKK2 was also expressed in MDSCs, Tg(Camkk2-EGFP)DF129Gsat (CaMKK2-EGFP reporter) mice were injected with E.G7 cells subcutaneously to study CaMKK2 in in vivo lymphoma model.

Figure 22A:
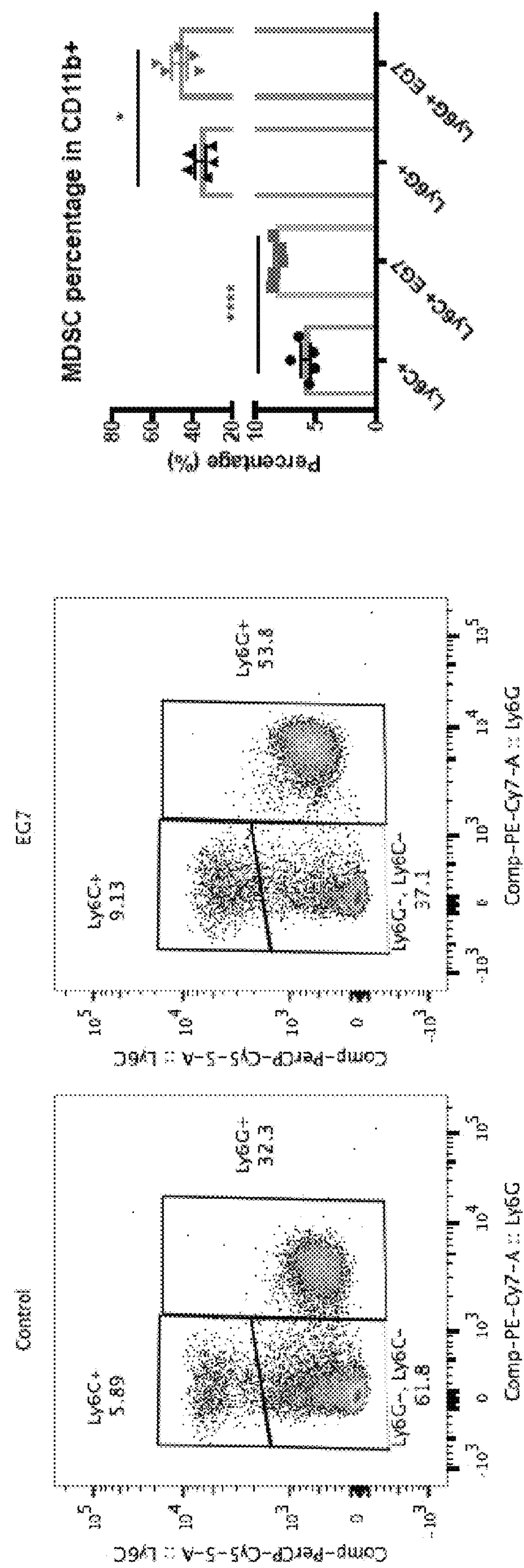
FIG. 22A shows flow cytometry of MDSC cells in the spleens of CaMKK2-EGFP reporter mice with or without E.G7 tumors. E.G7 tumor increased both M-MDSC and PMN-MDSC accumulation in the spleens. n=5.
Figure 22D:
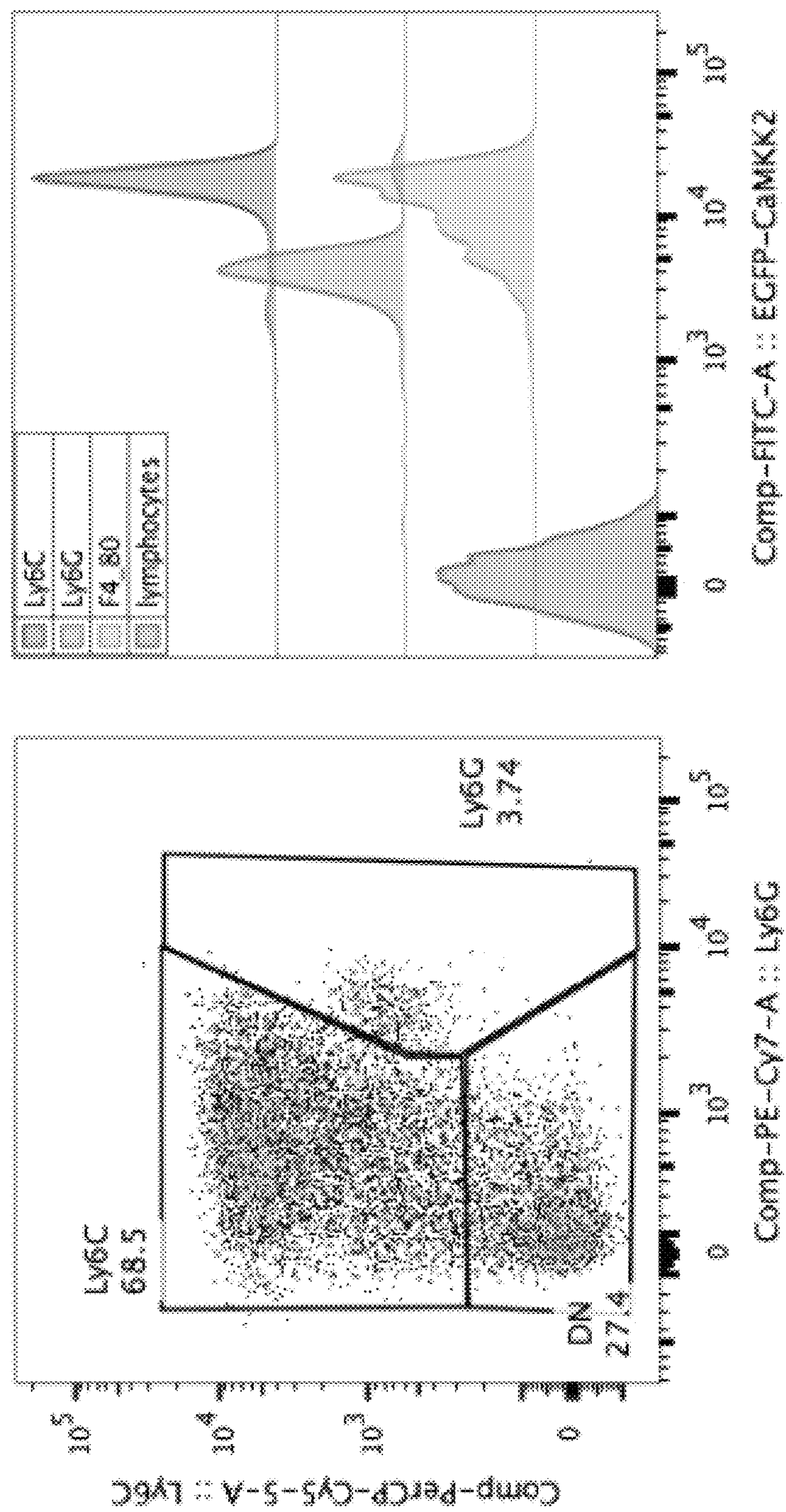
FIG. 22D shows flow cytometry of MDSC cells in the tumors of CaMKK2-EGFP reporter mice with E.G7 tumors. All experiments performed three times with 3-5 biological individuals. * p<0.05.  p<0.01. * p<0.001.

Three weeks after E.G7 injection, the myeloid cell component in spleens and tumors were analyzed by flow cytometry. The percentage of Ly6C+ M-MDSC and Ly6G+ PMN-MDSC in CD11b compartment were both significantly increased in the spleens of E.G7 tumor bearing mice compared to control mice (FIG. 22A. $p<0.0001$, $p<0.05$ respectively), indicating that E.G7 cells sufficiently induced MDSC accumulation in the spleens of tumor-bearing mice. When analyzing the CaMKK2 promoter activity in these cells, both M-MDSC and PMN-MDSC had significantly higher EGFP reporter signal compared to lymphocytes that do not express CaMKK2. (FIG. 22B, $p<0.0001$) The CaMKK2 promoter activity was four-fold higher in M-MDSC compared to PMN-MDSC ($P<0.0001$), while PMN-MDSC had similar promoter activity compared to CD11b+F4/80+ macrophage in which CaMKK2 is known to be expressed. Interestingly, the CaMKK2 promoter activity in MDSCs was comparable between tumor bearing mice and control mice (FIG. 22A), indicating that CaMKK2 expression in MDSCs was not interfered by E.G7 tumor condition.

The presence of cells with active CaMKK2 promoter in E.G7 tumor was confirmed by anti-EGFP immunochemistry staining. In the tumor tissue from CaMKK2 EGFP-reporter mice, the EGFP+ cells were shown as macrophage-like morphology. (FIG. 22C) To further identify these cell populations, the tumor tissue was digested by collagenase and analyzed by flow cytometry. Similar to that in the spleens, CaMKK2 promoter was on in both M-MDSC and PMN-MDSC, while M-MDSC had significantly higher EGFP MFI compared to PMN-MDSC. However, unlike in the spleens, the percentage of M-MDSC in CD11b compartment was dominant in tumor. This result indicated that CaMKK2 may play a crucial role in regulating the tumor immunity in tumor site.

CaMKK2 Ablation Suppresses Lymphoma Growth In Vivo Through the Myeloid Compartment.

Figure 23A:
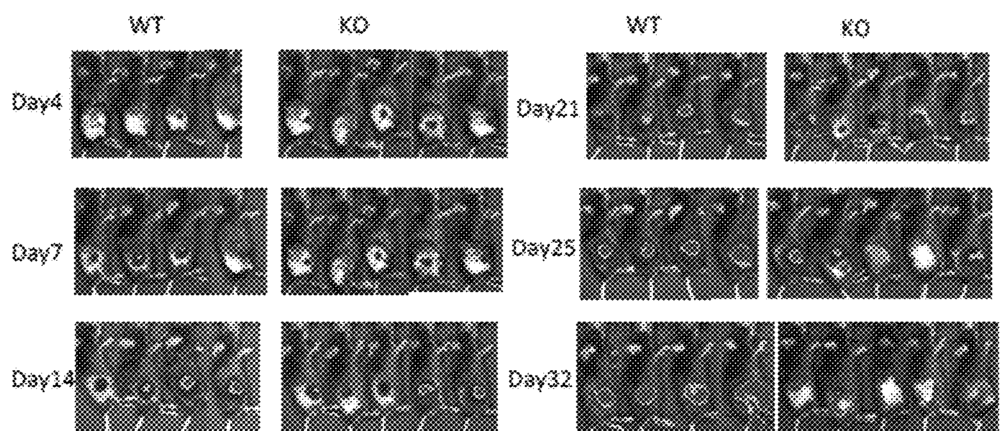
FIG. 23 shows E.G7 tumor growth was suppressed in CaMKK2 KO mice (FIG. 23A) Tumor bioluminescent imaging and photon count curve of WT and KO mice injected with 1×104 E.G7 cells s.c. in the flank. n=10. P=0.01.
(FIG. 23B) Tumor curve of WT and KO mice injected with 1×105 E.G7 cells s.c. in the flank. n=10.
(FIG. 23C) IFN-γ ELISpot performed with splenocytes from WT and KO mice 17 days after 1×105 E.G7 cells injection. n=3.
(FIG. 23D) Tumor size curve of E.G7 tumors in KO mice treated with anti-CD8 depletion or isotype control. n=5. P<0.0001.
(FIG. 23E) Tumor curve of LysM-Cre+;CaMKK2fl/fl mice and LysM-Cre+; CaMKK2wt/wt littermate controls injected with 1×105 E.G7 cells. n=10. P=0.0002.
(FIG. 23F) Flow cytometry of MDSC in the spleens of WT and KO mice injected with 1×105 E.G7 cells. n=5.
(FIG. 23G) Tumor curve of KO mice challenged with 1×105 E.G7 cells s.c. and injected with $2\times10^6$ MDSC cells through i.v. MDSCs were extracted from the spleens of WT or KO E.G7 tumor bearing mice 21 days after tumor injection. n=5. p<0.0001. Experiments repeated three times except that IFN-γ ELISpot, CD8 depletion, and MDSC injection were performed twice. * p<0.05.  p<0.01. * p<0.001, **** p<0.0001.
Figure 23B:
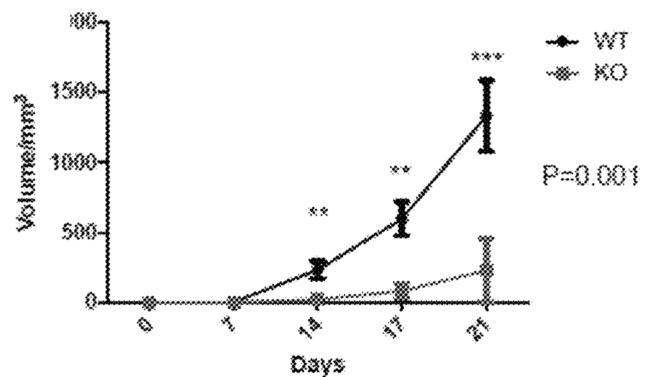
Figure 29A:
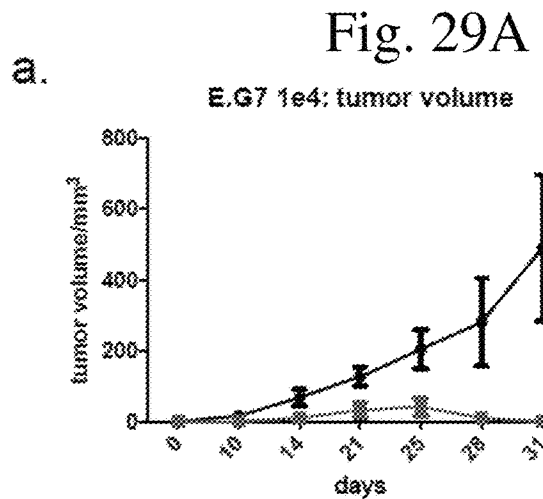
(FIG. 29A) E.G7 tumor size curve. WT and KO mice injected with $1\times10^4$ E.G7 cells subcutaneously were monitored. n=4 or 5. p<0.0001.
Figure 29B:
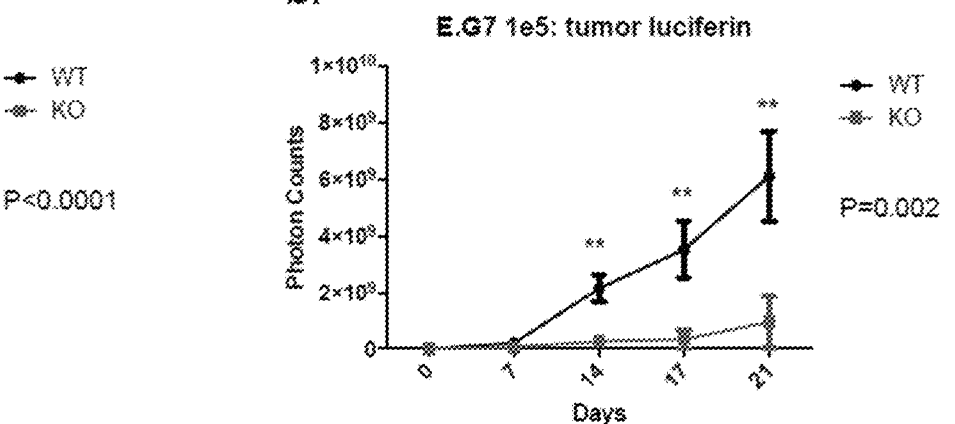
(FIG. 29B) E.G7 bioluminescent curve. WT and KO mice injected with $1\times10^5$ E.G7 cells subcutaneously were was monitored every week. n=10. Combined from two individual experiments. p=0.002.
Figure 29C:
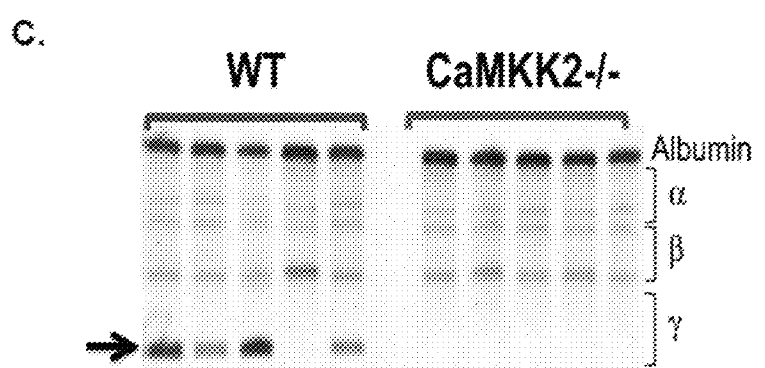
(FIG. 29C) Vk-myc lymphoma model. WT and KO mice were injected with Vk-myc myeloma cells through tail vein. Left panel showed the γ-globulin in the WT serum detected by electrophoresis. Right panel showed the survival of WT and KO mice with Vk-myc myeloma. p=0.015. n=5. Repeated three times.

To study the effect of CaMKK2 on lymphoma progression, different doses of E.G7 cells were subcutaneously injected into the right flank of wild-type (WT) and CaMKK2$^{-/-}$ (KO) mice. The tumor growth was monitored by measuring the size with calipers, and bioluminescent imaging every week. When challenged with lower dose of tumor cells, in the WT mice, the tumors were detectable by bioluminescence around Day 7, and gradually increased in photon signal and tumor size (FIG. 23A. FIG. 29A). In KO mice, although the tumors were successfully engrafted with detectable bioluminescent signal in the first two weeks, the tumor size and bioluminescent signal were gradually decreased after Day 21 and eventually disappeared after Day 32 (FIG. 23A. FIG. 29A). To better measure the tumors, we increased the E.G7 tumor dose to $1\times10^5$, and again confirmed the tumor suppression in KO mice by both tumor size and bioluminescent imaging (FIG. 23B, $p=0.001$. FIG. 29B, $p=0.002$). Re-challenging these KO mice with E.G7 cells did not yield tumor relapse in 100 days (data not shown), suggesting that the tumor suppression was mediated by anti-tumor immunity in KO mice. To exclude the possibility of E.G7 cell-line specific effect, Vk-Myc primary myeloma cells were injected into WT and KO mice through tail vein. Tumor progression was monitored by detecting γ-globulin in serum and mice survival. 4/5 WT mice were detected with γ-globulin in serum and died before Day 56, while all KO mice survived tumor-free till 98 days (FIG. 29C, $p=0.015$). The similar results from different tumor model confirmed that CaMKK2 play an important role in regulating tumor immunity.

Figure 23C:
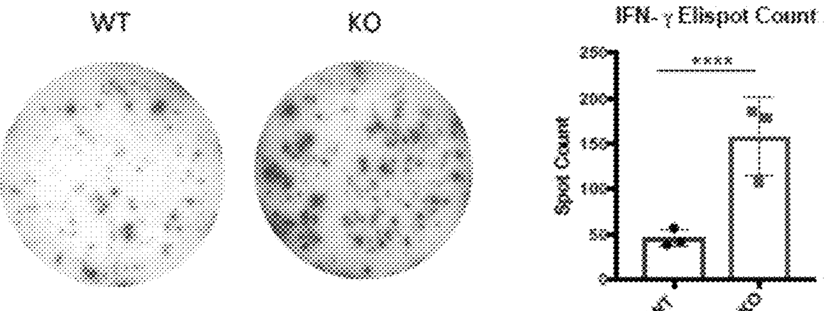
Figures 30A, 30B:
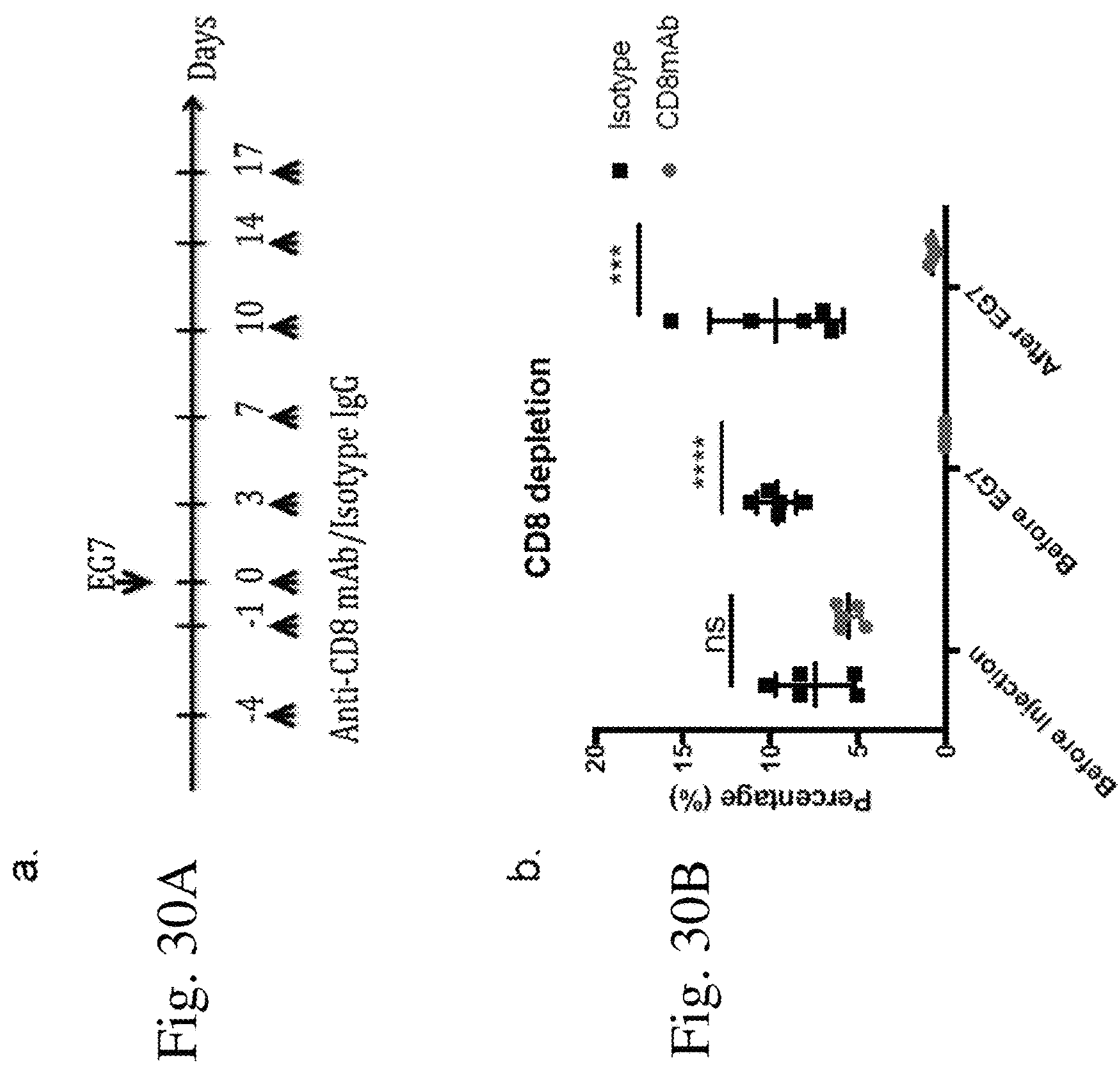
(FIG. 30A) Strategy of anti-CD8 mAb injection. Anti-CD8 mAb or isotype IgG were injected i.p. four days before E.G7 inoculation, and then twice per week.
(FIG. 30B) Flow cytometry detecting CD8% in CD45 cells in peripheral blood from mice receiving anti-CD8 mAb or control isotype before first dose injection, before E.G7 injection, and after E.G7 injection. n=5. ns, no statistical significance; ***, p<0.0001.

To further investigate the anti-tumor immunity in KO mice, IFN-γ ELISpot were performed with splenocytes from WT and KO mice 17 days after E.G7 injection. After 72 hours culture with OVA protein as stimulation, splenocytes from KO mice generated almost three times more IFN-γ spots compared to WT ones (FIG. 23C, $p<0.0001$). Considering that T cells, especially CD8 T cells, were the major resource of IFN-γ secretion in anti-tumor immunity, we depleted CD8+ T cells in CaMKK2 KO mice and subsequently challenged with E.G7 tumor cells. Anti-CD8 mAb was injected intraperitoneally every three days before and after the E.G7 inoculation as indicated. (FIG. 30A) The CD8+ cells had comparable percentage in peripheral blood before depletion, but were successfully depleted after mAb injection. (FIG. 30B) In the KO mice with CD8+ depletion, the E.G7 tumor suppression was successfully reversed compared to the ones that received no treatment or isotype IgG. (FIG. 23D. $p<0.0001$) This finding further confirms that CaMKK2 regulates lymphoma growth by suppressing T-cell anti-tumor immunity.

However, according to our previous experiment and literature reports, CaMKK2 is not expressed in lymphocytes but only in macrophages and other myeloid cells. Considering the crucial role of myeloid cells in regulating tumor immunity by interacting with T cells, we further tested if CaMKK2 regulated lymphoma development through myeloid cells using LyMCre+;CaMKK2$^{fl/fl}$ mice, in which CaMKK2 were specifically depleted in myeloid compartment. LysMCre+;CaMKK2$^{fl/fl}$ mice were generated by crossing LysM-Cre mice with CaMKK2$^{fl/fl}$ mice. The LysM-Cre+;CaMKK2$^{fl/fl}$ mice and its genotype control LysMCre+; CaMKK2$^{wt/wt}$ were challenged with E.G7 cells $5\times10^5$ subcutaneously, and monitored every 3-4 days. Similar to what was observed in the CaMKK2 global knockout model, E.G7 tumor size were significantly smaller in LysMCre+; CaMKK2$^{fl/fl}$ mice compared to the genotype control littermates (FIG. 23E, $p=0.002$).

We further analyzed the myeloid compartment in spleens from mice inoculated with E.G7 cells by flow cytometry. 21 days after injection, WT mice had significantly higher Ly6G+ MDSC percentage compared to that of KO mice (FIG. 23F, $p<0.05$), while Ly6C+ MDSC percentage had no statistical difference (data not shown). Considering that the tumor load was different in WT and KO mice, the fewer accumulation of MDSCs in KO mice may be explained by less tumor stimulation instead of inherent deficiency to generate functional MDSC. To test this hypothesis, $2\times10^6$ MDSCs were separated from the spleens of WT and KO tumor-bearing mice using Gr1 Miltenyi magnetic beads, and injected into another batch of KO mice through tail veins and simultaneously injected E.G7 cells subcutaneously. Surprisingly, while the tumor suppression remained in the control KO mice, tumors were developed in all KO mice that received either WT or KO MDSCs (FIG. 23G, $p<0.0001$). More interestingly, there was no difference in tumor growth between mice receiving WT or KO MDSCs. This result strongly suggested that although in vivo generated MDSCs from KO mice had comparable capability to suppress T-cell mediated anti-tumor immunity, CaMKK2 ablation sufficiently limited the E.G7-induced MDSC generation in vivo, thus inhibited tumor growth.

CaMKK2 Ablation Limits MDSC Generation In Vitro.

Given that tumor growth was different in WT and KO mice, we used in vitro generated bone marrow derived MDSC to further investigate the impact of CaMKK2 on MDSC generation. MDSCs were generated by culturing bone marrow cells from WT and KO mice in the media supplied with cytokines GM-CSF and IL-6 with or without 50% E.G7 supernatant. The floating cells were collected on Day 4 for analysis or further experiments.

Similar to in vivo MDSC, in vitro generated MDSC had significantly higher EGFP MFI in Ly6C compartment compared to Ly6G (FIG. 24A. FIG. 31A, $p<0.01$), indicating that in vitro generated M-MDSCs had higher CaMKK2 reporter activity. The expression of CaMKK2 in in vitro generated MDSCs were further confirmed by realtime PCR (FIG. 24B, $p<0.0001$) and immunoblot (FIG. 26A). All these data demonstrated that CaMKK2 was expressed in in vitro generated MDSCs.

Figure 24F:
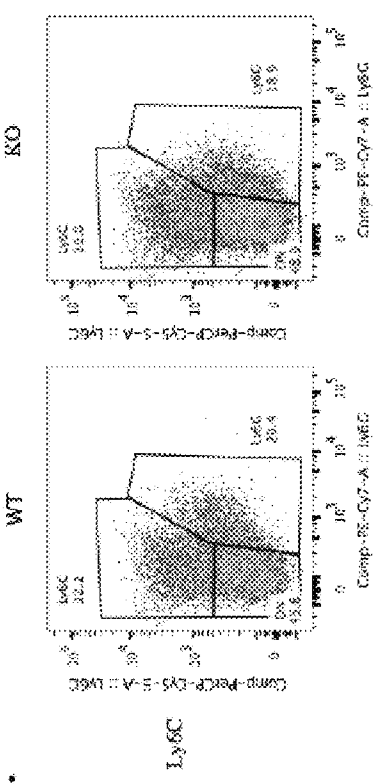
(FIG. 24F-G) Flow cytometry of sorted M-MDSC and PMN-MDSC cultured for 48 h with the presence of E.G7 supernatant and GM-CSF and IL-6.
Figure 24G:
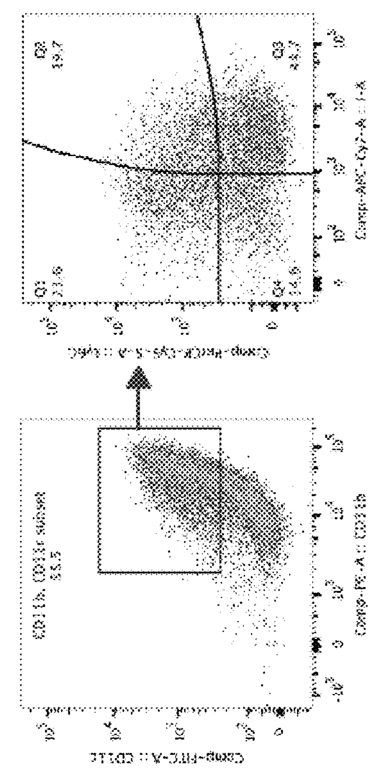
Figures 25A, 25B, 25C:
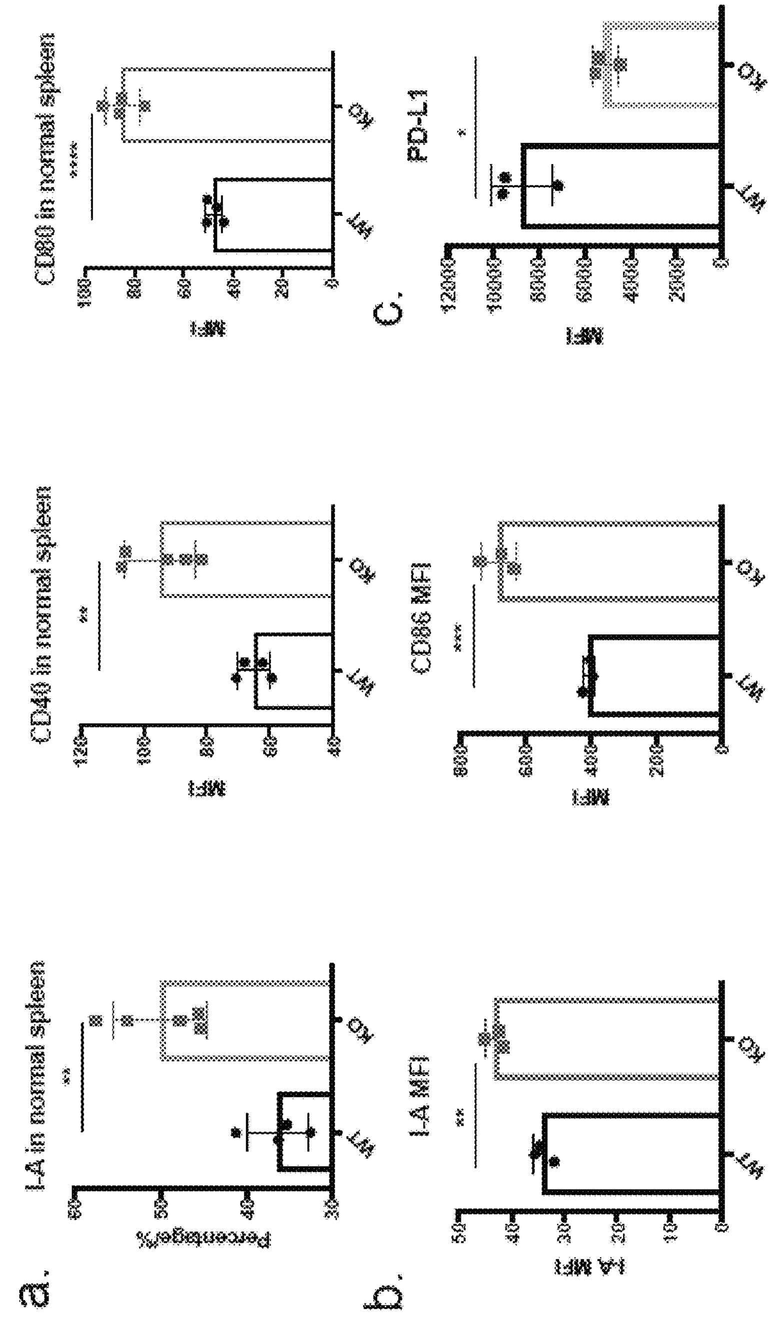
(FIG. 25A) Splenic DCs in normal KO mice had significantly higher expression of I-A (p<0.01), CD40 and CD80 compared to that in WT mice. n=5.
(FIG. 25B) MFI of I-A+ and CD86+ in CD11c+ BMDCs. n=3.
(FIG. 25C) Quantification and representative plot of PD-L1 MFI in BMDCs. n=3.
Figures 25D, 25E, 25F, 25G, 25H:
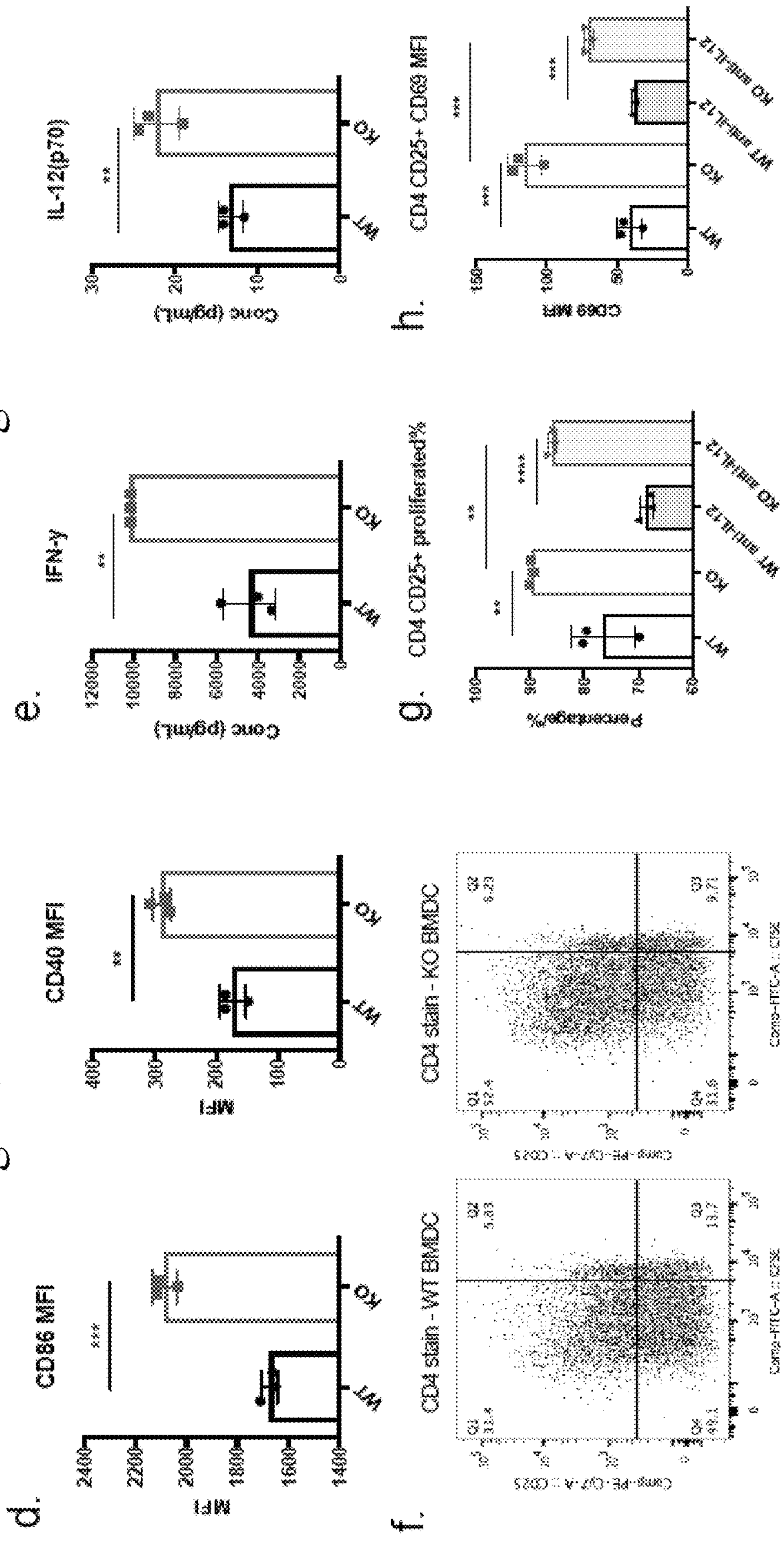
(FIG. 25D) KO BMDCs had significantly higher expression of CD86 and CD40 compared to WT BMDC after interacting with T cells for 24 h.
(FIG. 25E) Cytokine analysis of IFN-γ and IL12 (p70) in supernatant after co-culturing MDSC and T cells for 72 hours. n=3.
(FIGS. 25F&25I) Representative flow cytometry plots for CD4 (FIG. 25F) and CD8 (FIG. 25I) stain for CFSE-labeled T cells co-cultured with WT or KO CD11c+ BMDCs for 72 h.
(FIGS. 25G&25J) Quantitation of CD4+CD25+ (FIG. 25G) or CD8+CD25+ (FIG. 25J) proliferated percentage in CD3 cells after 72 h co-cultured with WT or KO CD11c+ BMDCs, with or without anti-IL12 mAb.
(FIGS. 25H&25K) Quantitation of CD69 MFI in CD4+CD25+ (FIG. 25H) or CD8+CD25+ (FIG. 25K) population after 72 h co-cultured with WT or KO CD11c+ BMDCs, with or without anti-IL12 mAb. n=3. All experiments repeated 2 times except cytokine analysis performed once. *p<0.05. p<0.01. *p<0.001.
Figure 25I:
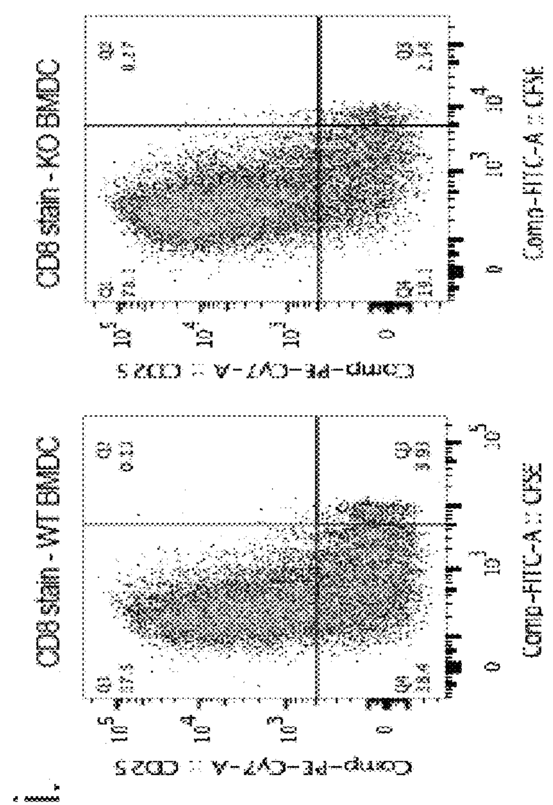

Consistent with the published results, E.G7 supernatant successfully increased the percentage and number of G-MDSC in both WT and KO cells. However, KO cells had larger fraction of Ly6C−Ly6G− double-negative (DN) subset compared to WT in both culture condition (FIG. 31B, $p<0.05$). More importantly, when cultured with or without E.G7 supernatant, KO marrow generated less M-MDSC ($p<0.001$ and $p<0.05$ with or without E.G7 sup) and PMN-MDSC ($p<0.05$ and $0<0.05$ with or without E.G7 sup) compared to that of WT. (FIGS. 24D and 24E. FIGS. 31C and 31D) Besides, in the DN compartment, there were more CD11C+I-A+ conventional dendritic cells ($p<0.05$) and F4/80+I-A+ cells ($p<0.05$) generated from the KO marrow (FIG. 24E). Ly6C+ M-MDSCs have been reported to differentiate into other myeloid subsets including PMN-MDSCs, DCs and TAMs in tumor sites and in vitro culture. We further confirmed this phenomenon by sorting MDSC into Ly6C+ and Ly6G+ subsets and cultured in vitro with the stimulation of E.G7 supernatant. After 48 h, only Ly6C+ cells but not Ly6G+ cells were differentiating towards Ly6G+ cells and DN cells in both WT and KO cells (FIG. 24F). Compared to WT cells, KO cells differentiated less into Ly6G cells (FIG. 25F), but more into CD11c+I-A+ Ly6C− compartment (FIG. 25G). These data confirmed that CaMKK2 ablation facilitates immature myeloid cells developing towards differentiated and matured cells in vitro mainly by regulating Ly6C+ M-MDSC subset.

To further test the function of in vitro generated MDSCs from WT and KO, MDSC were enriched by GR1 magnetic beads and cocultured with CFSE-labeled T cells with the stimulation of anti-CD3/CD28 beads. Both WT MDSC and KO MDSC showed comparable suppression to T-cell proliferation and activation (FIGS. 32 A-C). Adding sorted in vitro Gr1+ MDSCs successfully suppressed the proliferation of both CD4 ($p<0.01$) and CD8 T cells ($p<0.001$) mediated by anti-CD3/CD28 beads. Along with the decreased percentage of proliferated cells, Gr1+ cells also significantly decreased the percentage of CD25+ and CD69+ subsets in both CD4+ ($p<0.01$ for CD25, $p<0.001$ for CD69) and CD8+ ($p<0.01$ for CD25, $p<0.01$ for CD69) cells (FIGS. 32A-C). In all these analysis there was no detected difference between WT and KO wells. This result correlated with the in vivo tumor suppression experiment, revealing again that WT and KO MDSC have comparable immune-suppressive capability at single cell level.

Figure 24H:
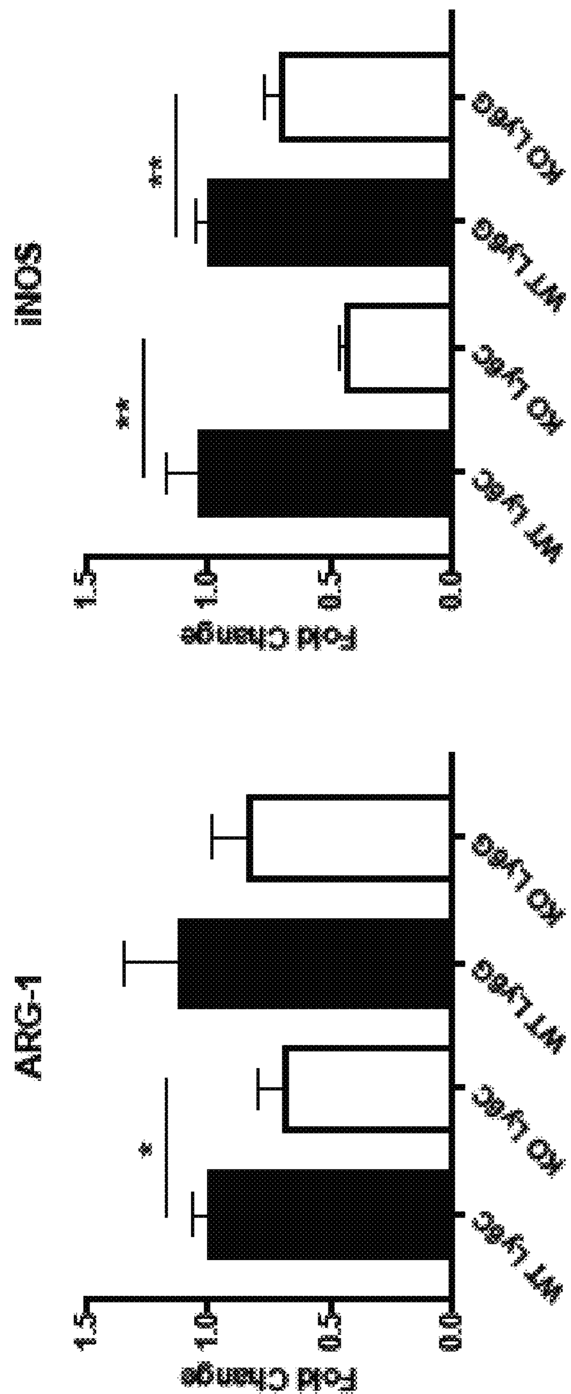
(FIG. 24H) Realtime PCR of Arginase-1 and iNOS expression in sorted M-MDSC and PMN-MDSC. n=6 combined from two experiments. Experiments repeated three times except sorted cells culture was performed once. *p<0.05. p<0.01. *p<0.001.

M-MDSC and PMN-MDSC have different mechanism to suppress T-cell function. When analyzed the major suppressive markers of MDSC by realtime-PCR, KO MDSCs had significantly lower transcription level of Arginase-1 ($p<0.0001$) and slightly lower level of iNOS (FIG. 32D) compared to WT MDSC. On the contrary, KO MDSC had much higher ROS level compared to WT MDSC (FIG. 32E, $p<0.001$). This result was further confirmed in the sorted M-MDSC and PMN-MDSC subsets (FIG. 24H. FIG. 26J). This surprising result may partially explain the comparable suppressive function between WT and KO MDSC, and also indicates the different cell metabolism state between WT and KO cells.

CaMKK2 Regulates Macrophage Polarization and Facilitates Myeloid Cells Differentiating Towards Mature Dendritic Cells.

Besides MDSC, other subsets of myeloid cells including dendritic cells and macrophages also regulate anti-tumor immunity. In in vitro culture when exposed to E.G7 supernatant, we also observed better maturation of myeloid cells towards M1-like macrophages and mature dendritic cells from CaMKK2 KO marrow.

For most MDSC studies only the floating cells were analyzed. We noticed that when inducing MDSC in vitro, there were cells attached to the bottom of the wells. Stained with crystal violet, the attached cells showed a similar morphology to in vitro generated macrophages, yet with very different shape between WT and KO. While the WT attached cells showed an M2-like morphology with significant elongation and branching, the KO cells were more M1-like with round shape and abundant cytoplasm (FIG. 33A). When detached from wells and analyzed by flow cytometry, these cells were confirmed to be CD11b+Ly6C−Ly6G−F4/80+ macrophages. Surprisingly, the I-A expression was significantly higher in KO cells compared to that in WT ones (FIG. 33B, $p<0.0001$). Besides, the WT attached cells had significantly higher RNA level of M2 markers Arginase I ($p<0.01$) and Chi313 ($p<0.0001$) (FIG. 33C). These data strongly suggest that the macrophages generated from WT and KO had different polarization when induced towards MDSC with E.G7 supernatant in vitro.

Dendritic cells are well studied as the most important antigen-presenting cells to regulate T-cell function in anti-tumor activity. During dendritic cell maturation, the expression of MHCs molecules and T-cell costimulatory factors (e.g. CD40, CD86) is up-regulated. In normal condition, we noticed that CaMKK2 KO mice had relatively higher I-A, CD80, and CD40 expression in the CD11b+CD11c+ compartment in the spleens compared to WT mice (FIG. 25A). To further study how CaMKK2 ablation impacts DC maturation and function in a compared lymphoma condition, we generated bone marrow derived dendritic cells (B MDC) from WT and KO mice in vitro with GM-CSF and IL-4 cytokines along with 50% E.G7 supernatant. Cells were analyzed by flow cytometry on Day 5.

We first confirmed the expression of CaMKK2 in BMDCs by realtime RT-PCR (FIG. 34A, $p<0.0001$) and western blot. (FIG. 33B). Gated under CD11b+CD11c+ compartment, in vitro generated BMDCs from KO mice had higher I-A+ and CD86+ expression (FIG. 25B. $p<0.01$ and $p<0.001$ respectively) and percentage (FIG. 34C. $p<0.001$ and $p<0.01$ respectively) compared to WT cells. Besides, PD-L1, an important molecule that regulates T-cell, also had lower MFI in KO BMDCs compared to WT. (FIG. 25C. $p<0.05$) These data collectively indicated that CaMKK2 ablation enhanced dendritic cell maturation in vitro, and potentially induced a stronger ability to stimulate T cells.

Figure 25J:
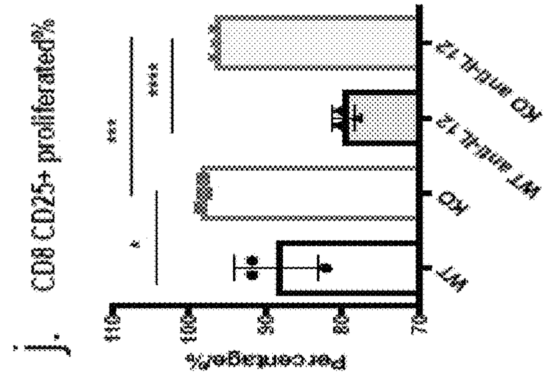
Figure 25K:
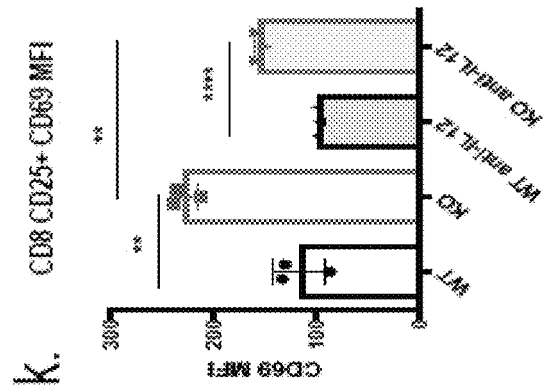

To functionally verify this hypothesis, in vitro cultured BMDCs were enriched by anti-CD11c magnetic beads, and co-cultured with CSFE-labeled T cells in the presence of soluble anti-CD3 mAb for 72 h. The BMDCs surface marker and T-cell proliferation were monitored by flow cytometry. Even though the CD40 expression level was comparable in WT and KO BMDCs before co-culture (data not shown), KO BMDCs have significantly higher expression of CD40 ($P<0.01$) and CD86 ($P<0.001$) compared to WT BMDCs (FIG. 25D) after 24 h T-cell coculture. Besides the changes in BMDCs, T cells cocultured with KO BMDCs had significantly higher CD25+ percentage (FIGS. 25G & 25J. $p<0.01$ for CD4, $p<0.05$ for CD8), with higher CD69 expression (FIGS. 25H & 25K. $p<0.001$ for CD4, $p<0.01$ for CD8) in the proliferated population (FIGS. 25F-H). We further confirmed these proliferated CD25+ T cells were FoxP3 negative, ruling out the accumulation of regulatory T cells (data not shown). The difference of costimulatory factors expression before and after T-cell interaction suggests that CaMKK2 ablation increased the ability of BMDC to stimulate T-cell proliferation and activation.

Cytokine secretion is another important marker for immune function. IL-12 is one of the crucial cytokines that secreted by dendritic cells to stimulate T-cell activation. The activated T cells increase IFN-γ secretion, which can in turn enhance the DC function. When analyzing the cytokines in the supernatant, the concentration of IFN-γ and IL-12 were both higher from the coculture of KO BMDC with T cells (FIG. 25E. $p<0.01$) compared to WT ones. Using anti-IL12 neutralizing mAb in the coculture system partially reversed the KO BMDC-mediated T-cell proliferation and activation. In the presence of anti-IL12 mAb, the proliferation percentage ($p<0.01$ for CD4 and $p<0.001$ for CD8) and CD69 expression ($p<0.001$ for CD4 and $p<0.01$ for CD8) on the CD25+ proliferated T cells were both significantly decreased in the T cells co-cultured with KO BMDCs. (FIGS. 26G-H) The same phenomenon was seen in T cells co-cultured with WT BMDCs at 48 h (data not shown).

To further confirm this phenomenon in antigen-specific condition, splenic CD11c+ cells sorted from tumor-bearing WT and KO mice were co-cultured with OVA-primed OT1 T cells and stimulated with OVA 257-264 (SIINFEKL) peptide for 72 h. KO splenic DCs again better induced OT1 T-cell proliferation and activation, while blocking IL-12 significantly reduced CD25 and CD69 expression. (FIGS. 34 D&E). Taken together, these data suggest that KO DCs had higher IL-12 secretion, leading to enhanced ability to stimulate T-cell proliferation and activation compared to WT cells.

In conclusion, CaMKK2 ablation limited MDSC generation, while facilitated myeloid cells differentiation towards more mature macrophages and dendritic cells, and potentially promoted T-cell anti-tumor function. Even though CaMKK2 KO MDSCs preserved similar suppressive function compared to WT ones, KO DCs were more potent in stimulating T-cell proliferation and activation. This phenomenon was consistent both in vivo and in vitro under E.G7 lymphoma condition.

AMPK Pathway is the Downstream Target of CaMKK2 in Regulating Myeloid Cells Differentiation Through Mitochondrial Metabolism.

After confirming that CaMKK2 ablation induced less MDSC accumulation and promoted myeloid cell differentiation under lymphoma condition, we further explored the potential mechanism that led to this phenomenon. AMPK as a direct downstream target of CaMKK2, has been reported as a crucial regulator of cell metabolism and differentiation. When analyzed by Western blot, AMPK phosphorylation was shown suppressed in both M-MDSC and PMN-MDSC in KO cells (FIG. 26A). To test if the AMPK phosphorylation was inducible during MDSC generation, MDSCs were generated in vitro with GM-CSF and IL-6 cytokines and E.G7 supernatant, starved from cytokines for overnight, and re-stimulated with IL-6. Western blot showed that after overnight starvation, AMPK phosphorylation remained at very low level in both WT and KO MDSCs (FIG. 27B). However, once stimulated with IL-6, AMPK phosphorylation was activated within 30 min and remained high after 2 h in WT MDSC, while KO MDSC did not show significant AMPK phosphorylation during the whole time. Interestingly, although the AMPK phosphorylation was inhibited in CaMKK2 KO cells, the phosphorylation of STAT3, a direct target of IL-6, were comparable in Ly6C cells between WT and KO. (FIG. 26A) This data suggested that CaMKK2 ablation in MDSC did not interfere IL-6-mediated STAT3 phosphorylation, but inhibited AMPK phosphorylation to regulate the downstream signaling pathway in MDSC.

Figures 26D, 26E, 26F, 26G:
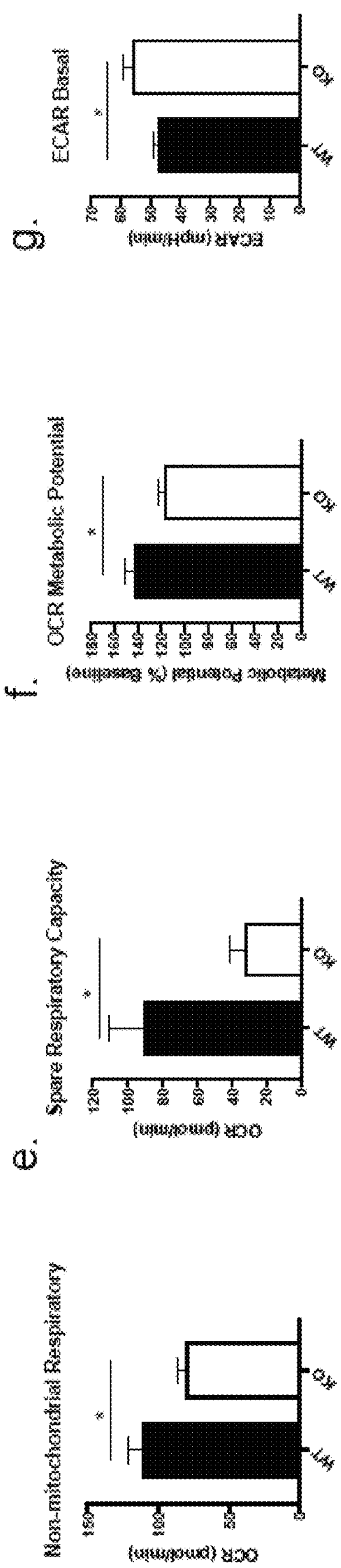
Figure 26H:
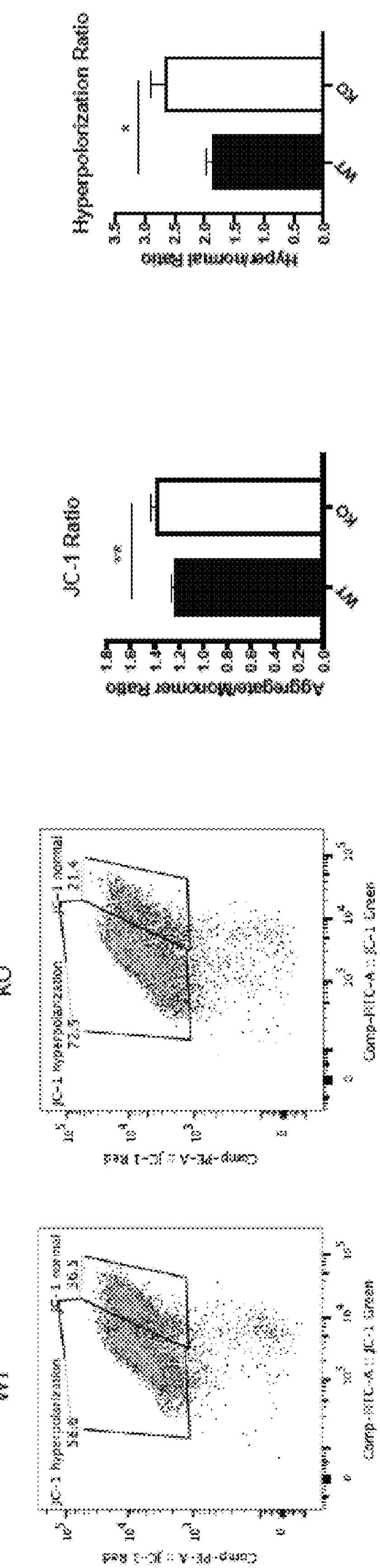
(FIG. 26H) Representative plots and quantification of JC-1 assay of WT and KO MDSC. n=6.

AMPK is a metabolic sensor that maintains the cellular energy homeostasis and regulates multiple aspects of cell function including cell differentiation. To test if deficiency in AMPK phosphorylation impaired cellular metabolism in KO MDSC, oxygen consumption rate (OCR) and extracellular acidification rate (ECAR) were analyzed using Agilent Searhorse XF technology. Although WT and KO MDSC cells had comparable basal OCR level, the OCR of KO cells was significantly lower after Oligomycin and FCCP challenging. (FIG. 26C, $p<0.01$) Compared to WT cells, KO MDSC had significantly lower non-mitochondrial respiratory rate, decreased spare respiratory capacity and OCR metabolic potential, but higher ECAR basal level (FIGS. 26D-G, $p<0.05$). This evidence suggested that WT and KO MDSC had distinct metabolic profile while KO MDSCs highly relied on mitochondrial respiratory for energy generation. The limited capacity of glycolysis due to AMPK inhibition contributed to the decreased spare respiratory capacity and metabolic potential in KO MDSC, leading to the higher mitochondrial membrane potential. Indeed, the hyperpolarization of KO M-MDSC was confirmed by JC-1 staining. Although the mitochondrial mass was comparable between WT and KO cells (FIG. 26I), the JC-1 aggregate/monomer ratio ($p<0.01$) and the ratio of hyperpolarization/normal cells ($p<0.05$) were both significantly higher in KO M-MDSC (FIG. 26H). High mitochondrial potential leads to increased ROS production. Combined with the decreased level of catalase in KO M-MDSC (FIG. 26K, $p<0.05$), the ROS level in both KO M-MDSC and PMN-MDSC were significantly higher than WT ones (FIG. 26J, $p<0.01$).

Increased ROS is a crucial reason for cellular vulnerability during oxidation stress. To test the susceptibility of MDSCs towards oxidation stress, we challenged the in vitro MDSC cells with 200 μm $H_2O_2$ and monitored cell apoptosis every 15 minutes using flow cytometry. By staining with AnnexinV and 7-AAD, we confirmed that both Ly6C and Ly6G subsets in KO MDSCs had higher death rate of AnnexinV+7-AAD+ compartment at all the time points. (FIG. 29F) After 60 min stimulation, the dead-cell fold change was significantly higher ($p<0.0001$) in both Ly6C and Ly6G compartment in KO cells (FIG. 26L), suggesting that KO MDSCs were more susceptible to oxidative stress and more prone to apoptosis under stimulation.

Increased ROS Level Facilitates the Differentiation of CaMKK2 KO M-MDSCs Towards Mature Dendritic Cells.

ROS has been shown to regulate cell fate balance between apoptosis and differentiation. Even though the role of ROS remains controversial in MDSC biology, it is generally accepted that ROS promotes cell differentiation at low dose, and induces cell apoptosis at high dose. KO MDSCs showed higher ROS level compared to WT cells (FIG. 26J. $p<0.01$), suggesting the increased tendency to differentiate to more mature subsets.

Figure 27C:
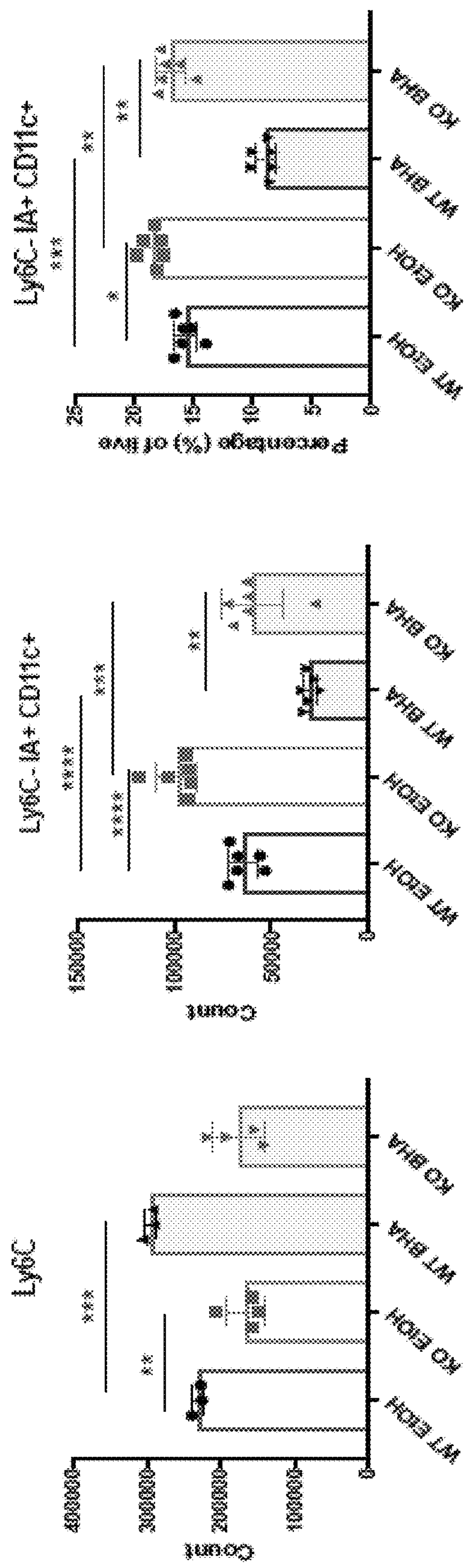
(FIG. 27C) MDSC in vitro generated with 20 μM BHA added. Drugs were added on Day 0 and Day 3 into culture media. Representative plots from two individual experiments. n=3-6. *p<0.05. p<0.01. *p<0.001.

To further study how ROS regulates MDSC differentiation, low dose of $H_2O_2$ and two commonly used antioxidants, MitoTEMPO and Butylated hydroxyanisole (BHA), were separately added to the culture media during MDSC in vitro generation. At basal condition, KO marrow generated less M-MDSC cells while differentiated more into Ly6C−CD11c+I-A+ mature dendritic cells compared to WT ones. (FIGS. 27A-C) Low dose $H_2O_2$ significantly decreased the number of WT M-MDSC, while increased both the count and percentage of Ly6C−IA+CD11c+ dendritic cells in WT and KO (FIG. 27A.) On the contrary, MitoTEMPO, a specific scavenger of mitochondrial superoxide, significantly induced M-MDSC accumulation in both WT and KO cells, and decreased the differentiation towards Ly6C−IA+CD11c+ dendritic cell (FIG. 27B). The same phenomenon was also observed by adding BHA, an antioxidant that can stabilizes and sequesters free radicals, in the culture medial (FIG. 27C). These data collectively indicated that ROS was essential for M-MDSC differentiating towards mature dendritic cells. The higher level of ROS in CaMKK2 KO MDSCs limited M-MDSC accumulation by facilitating the myeloid cell differentiation.

CaMKK2 Pharmaceutical Inhibitor Successfully Inhibits Lymphoma Growth and Reshaped the Immune Environment.

Based on the previous conclusion that CaMKK2 ablation interfered lymphoma growth by limiting MDSC accumulation and promoting myeloid-cell maturation, we proposed to use CaMKK2 inhibitor as a potential immune therapy to treat lymphoma. STO-609 is a highly selective pharmaceutical inhibitor of CaMKK2. In different cancer cell lines, STO-609 has been tested to directly suppress cancer cell survival and proliferation. Here we used STO-609 to suppress CaMKK2, hoping to reshape the lymphoma immune environment.

10 days after $5\times10^5$ E.G7 injection, C57BL/6 mice with confirmed E.G7 growth by bioluminescent imaging were randomized into DMSO control group and STO-609 treatment group. STO-609 or DMSO as vehicle control were injected peritoneally every 2-3 days while the tumor size was monitored. With STO-609 injection, lymphoma growth was significantly suppressed compared to the ones received DMSO vehicle control. (FIG. 28A. $p<0.001$) Moreover, the percentage of CD3 in the tumors was significantly higher in STO-609 treatment group. (FIG. 28B. $p<0.05$) On the contrary, the percentage of M-MDSC was much lower in the spleens of the mice treated with STO-609. (FIG. 28C. $p<0.001$) These data strongly suggests that using STO-609 as CaMKK2 inhibitor in E.G7 tumor bearing mice can successfully suppress tumor growth by reshaping the tumor microenvironment and whole-body immunity to enhanced anti-tumor capability.

As previously stated, lymphoma can occur or migrate to CNS to form CNS lymphoma, which is usually refractory to conventional lymphoma treatment, resulting in high mortality. Unlike the subcutaneous flank model in which CaMKK2-expressing adjacent parenchymal cells are absent, CaMKK2 is highly expressed in neurons in CNS system. Thus, this intracranial model of lymphoma will be a helpful means to investigate whether CaMKK2-enriched parenchymal cells have an impact on lymphoma growth.

To answer this question, we used the intracranial lymphoma model. $1\times10^4$ E.G7 cells suspended in 25 μl methylcellulose were injected into the right caudate nuclei of WT and CaMKK2$^{-/-}$ mice. The mice were monitored by physical examination every other day. Similar to the subcutaneous injection model, in WT group, mice start to show abnormal gesture and movement including hunching, circling, paralysis, decreased appetite and body weight loss from 10 days after injection (FIG. 36A). Most WT mice were sacrificed before 25 days after injection when they were moribund (FIG. 36B). Comparing to WT mice, only 1 in 10 CaMKK2$^{-/-}$ mice with E.G7 intracranial injection was sick and needed to be sacrificed before the end of the experiment (FIG. 36). The difference of tumor growth in WT and KO is statistically significant ($P<0.0001$).

To better monitor the tumor growth, weekly bioluminescent imaging was performed on all mice. With the help of imaging, intracranial tumors were clearly shown in WT group on Day 21, yet not in CaMKK2$^{-/-}$ mice (FIG. 37B). On Day 21, the photon count of luciferin signal was significantly different ($P<0.001$) between the two groups (FIG. 37A). These findings corroborate the conclusion in the intracranial tumor model, indicating that CaMKK2 expression in parenchymal cells does not impact lymphoma progression. The significant difference of tumor growth in the WT and CaMKK2$^{-/-}$ mice is more likely due to the systemic effect mediated by CaMKK2. Considering that CaMKK2 is also expressed in macrophages and some hematopoietic progenitors, it is likely that the CaMKK2-ablation impacts the immune responses to suppress the growth of lymphoma.

Materials and Methods

E.G7 Cell Culture

E.G7 cells were purchased from American Type Tissue Culture Collection (Rockville, MD, USA). E.G7 cells are derived from EL4 C57BL/6 (H-2 b) mouse lymphoma cell line EL4 and stably transfected with OVA expressing plasmid. E.G7 cells were further stably transfected with GFP-Luciferase expressing plasmid by Dr. Yiping Yang's lab. Cells were cultured in RPMI 1640 (Gibco, MA, USA) supplied with 4.5 g/L glucose (Sigma-Aldrich, MO, USA), 2 mM L-glutamine, 1.5 g/L sodium bicarbonate, 10 mM HEPES, 1.0 mM sodium pyruvate (all from Gibco, MA, USA), 0.05 mM 2-mercaptoethanol, 0.4 mg/ml G418 (Sigma-Aldrich, MO, USA), and 10% fetal bovine serum (Hyclone, MA, USA). Cells were kept in humidified 37° C. $CO_2$ incubator.

Mice

C57BL/6 mice were purchased from the Jackson Laboratory (CA, USA). Wild-type (WT) and CaMKK2 global knock-out (Camkk2−/−) mice were generated as described (Anderson, Ribar, 2008) and back-crossed to C57BL/6 for more than 7 generations.

Tg(Camkk2-EGFP)DF129Gsat mice were originally provided by the Mutant Mouse Regional Resource Centers (MMRRCC) and back-crossed to C57BL/6 for more than 7 generations. (Gong et al., 2003) In general, this transgenic strain has the coding sequence for enhanced green fluorescent protein (EGFP) inserted into the mouse genomic chromosome at the ATG transcription initiation codon of the CaMKK2 gene. Thus, the expression of the EGFP reporter is driven by the CaMKK2 gene. LysMCre+;CaMKK2fl/fl and its genotype control LysMCre+;CaMKK2$^{+/+}$ were generated by crossing B6.129P2-Lyz2$^{tm1}$(cre)Ifo/J mice from the Jackson Laboratory with CaMKK2$^{lox/lox}$ mice. All the mice were used between 8-16 weeks, with gender and age matched in experimental groups and control groups. The animals were housed in Duke University animal facilities under a 12 hour light/12 hour dark cycle with food and water ad libitum provided. All animal care and experimental procedures were approved by National Institute of Health and Duke University Institutional Animal Care and Use Committee, and in compliance with the guidelines.

Intracranial Tumor Model

The intracranial tumor model was generated with the help of Dr. David Synder. In brief, 1×10$^4$ E.G7 cells were suspended in 25 μl 10% methylcellulose and stereotactically implanted into the right caudate nucleus of the brain 8-12 weeks CaMKK2 WT and KO mice as previously described. (Sampson et al., 1999) Mice were monitored by physical examination every other day and bioluminescence imaging each week. The moribund mice with severe hunching and decreased activity were sacrificed.

Flank Tumor Model 1×10$^5$ E.G7 cells were suspended in 100 μl PBS and implanted subcutaneously to the right side flank of the mice. Tumors were monitored using bioluminescence imaging each week. Tumor sizes were measured with calibrator every 3-4 days and calculated as: Length×Width×Width/2. In some experiments 5×10$^5$ cells were used as indicated. Mice were sacrificed when tumor reached 2 cm$^3$.

ELISpot Analysis

CaMKK2 WT and KO mice were injected with E.G7 cells subcutaneously to generate tumor models. On day 21, mice were sacrificed and the spleens were removed using sterilized scissors. Single-cell splenocyte suspension was generated as previously described. 5×10$^5$ splenocytes were suspended in 200 μl complete DMEM media with 10% FBS as described before and seeded into mouse IFN-gamma ELISpot kit (R&D, Minn., USA). OVA protein was added at 1 mg/ml as stimulator. Cells were cultured in a humidified incubator with 5% $CO_2$ for 24 h, and reactions were processed as instructed. The plate was read using a CTL-ImmunoSpot® S6 FluoroSpot Line (Cellular Technology Ltd, OH, USA) and the data was analyzed with ImmunoSpot software (Cellular Technology Ltd, OH, USA).

Tumor Pathology Staining

Tumor-bearing mice were sacrificed in $CO_2$ chamber. The tumors were removed using sterilized sectioning scissors and forceps. The tissues were fixed in formaldehyde and further embedded in paraffin. The slides were cut at 7 μm and stained with H&E and examined under microscope.

Tumor Digestion

The removed tumors were further minced with a surgical scalpel. The tissue were added to 5 ml HBSS w/$Ca^{2+}$ and $Mg^{2+}$ (ThermoFisher Scientific, MA, USA) supplied with collagenase 2 mg/ml and DNase 0.1 mg/ml (Roche, Basel, Switzerland) in gentleMACS C tubes and dissecting with gentleMACS dissociator (Miltenyi, Bergisch Gladbach, Germany). The samples were incubated in 37° C. for 15 min and passed through the 70 μm cell strainers (Coring, NY, USA). Cells were washed twice in PBS w/2% FBS before staining.

Flow Cytometry Analysis

For myeloid cells staining, 5×10$^6$ cells were incubated with FITC anti-mouse CD11c, PE anti-mouse/human CD11b, PE-Cy7 anti-mouse Ly6G, APC anti-mouse F4/80 (all from BioLegend, CA, USA), PerCpCy5.5 anti-mouse Ly6C, Fixable Viability Dye eFluor® 450 (eBioscience, CA, USA) at 4° C. for 15 min in dark and washed with PBS w/2% FBS. The stained cells were analyzed using a BD FACSCanto flow cytometer (BD, NJ, USA). Data is analyzed using FlowJo (TreeStar, OR, USA).

In Vivo Bioluminescence Imaging

A fresh stock solution of D-Luciferin (Perkin Elmer, MA, USA) was diluted in DPBS at 30 mg/ml and filtered sterilize through 0.2 μm filter. Each mouse was injected with 100 μl stock solution intra-peritoneally 10-15 min before imaging. Mice were anesthetized with isoflurane (Butler-Schein, OH, USA) and shaved with a shaving trimmer (Wahl, IL, USA) and imaged with IVIS Lumina XR (Perkin Elmer, MA, USA) for 1 min. Image was analyzed with IVIS Lumina LivingImage Software (Perkin Elmer, MA, USA).

T-Cell Depletion Treatment

CaMKK2 KO mice were injected peritoneally with anti-mouse CD8 monoclonal antibody or its IgG isotype (BioX-Cell, NH, USA) each at 200 μl at the concentration of 1 mg/ml at 4 days and 1 days before tumor inoculation, and every 3 days after tumor cell injection. The effect of CD8 depletion was monitored by flow cytometry using 50 μl peripheral blood staining with APC anti-mouse CD8, APC-Cy7 anti-mouse CD45.2 (Biolegend, CA, USA) at the same time. The mice were injected with 1×10$^5$ E.G7 cells to the right flank subcutaneously on day 0. The tumor size was monitored with a calibration every 3-4 days. Tumor volume was calculated as indicated before. The experiment was terminated when the tumor reached 2 cm$^3$.

STO-609 Treatment

STO-609 was purchased from TORIS Bioscience (Bristol, UK). The C57BL/6 mice were purchased from the Jackson Laboratory (CA, USA). The mice were inoculated with 5×10$^5$ E.G7 cells to the right flank subcutaneously on day 0. On day 7, the tumor growth was measured using bioluminescent imaging. All the mice with visible tumor under luciferin detection were randomized into STO-609 treatment group or DMSO control group. The mice were injected peritoneally with 200 μl STO-609 at concentration of 20 mM or DMSO as control every 3-4 days for two weeks. The tumor size was monitored using a calibrator every 3-4 days. The experiment was terminated when the tumor reached 2 cm$^3$.

Vk*Myc Myeloma Cells and Myeloma Model

Vk*Myc myeloma cells were precious gift from Dr. Marta Chesi. The generation and characteristics of the cells were described in publication. (Chesi et al., 2008) Tumor cells were purified using Ficoll (Cedarland, Ontario, Canada) from the spleens of C57BL/6 mice that were inoculated with myeloma cells and showed detectable M-spike. For tumor inoculation, 5×10$^5$ cells were injected through tail vein into each mouse. Peripheral blood was collected from maxillary sinus every week since Week 4. Serum was collected from the blood by high speed centrifuging, and gamma immunoglobulin was detected using protein electrophoresis and staining (Helena Laboratories, Texas, USA). Mice were monitored every day and sacrificed when become moribund.

Generating Bone Marrow Derived Dendritic Cells

The CaMKK2 WT and KO mice were sacrificed in a $CO_2$ chamber and sterilized with 70% alcohol. The femur and tibia bones were removed using the sterilized sectioning scissors and forceps and further crunched in 5 ml PBS with 2% FBS and 2 mM EDTA using a ceramic molar. The liquid was further passed through a 70 μm cell strainers (Coring, NY, USA) to form the single cell suspension. After spinning down the cells, the erythrocytes were lysed using the red blood cell lysis buffer (Biolegend, CA, USA) followed by two washes in PBS with 2% FBS and 2 mM EDTA. The cells were seeded to 6-well plates (Coring, NY, USA) at $5\times10^6$ per well in 5 ml DMEM (Gibco, MA, USA) supplied with 10% FBS, 2 mM L-glutamine, 1.5 g/L sodium bicarbonate, 10 mM HEPES, 1.0 mM sodium pyruvate (all from Gibco, MA, USA), 10% fetal bovine serum (Hyclone, MA, USA), 10 nM recombinant mouse GM-CSF and 10 nM recombinant mouse IL-4 (both from Biolegend, CA, USA), and with or without 50% E.G7 supernatant. The media was half-changed on day 3. The floating cells were collected on day 5 for flow cytometry analysis and further enriched by anti-mouse CD11c Microbeads (Miltenyi, Bergisch Gladbach, Germany). The cells with the purity >85% were used. In some experiments as indicated, the cells were stained with FITC anti-mouse CD11c, PE anti-mouse/human CD11b (Biolegend, CA, USA). Double positive cells were sorted with BD FACS Aria II cell sorter (BD, NJ, USA).

Generating Myeloid Derived Suppressor Cells

Bone marrow cells were prepared as described before. Cells after RBC lysis were seeded to 6-well plates (Coring, NY, USA) at $1\times10^6$ per well in 5 ml DMEM (Gibco, MA, USA) supplied with 10% FBS, 2 mM L-glutamine, 1.5 g/L sodium bicarbonate, 10 mM HEPES, 1.0 mM sodium pyruvate (all from Gibco, MA, USA), 10% fetal bovine serum (Hyclone, MA, USA), 40 nM recombinant mouse GM-CSF and 40 nM recombinant mouse IL-6 (Biolegend, CA, USA), and with or without 50% E.G7 supernatant. The supernatant was half-changed on Day 3. The floating cells were collected on Day 5 and enriched by anti-mouse Gr-1 Microbeads (Miltenyi, Bergisch Gladbach, Germany). The cells with the purity >90% were used. In some experiments as indicated, the cells were stained with APC anti-mouse Gr-1, PE anti-mouse/human CD11b (Biolegend, CA, USA). Double positive cells were sorted with BD FACS Aria II cell sorter (BD, NJ, USA).

Co-culture of BMDC and T cells

Primary Cell Separation

BMDCs were prepared as described. T cells were separated from spleens of C57BL/6 mice. The spleens were removed using sterilized sectioning scissors and smashed with the end of the plugs from the 1.5 ml syringes on a 70 μm cell strainers (Coring, NY, USA). Cells were flushed into 50 ml centrifuge tubes (BD falcon, Mass., USA) using PBS with 2% FBS and 2 mM EDTA. After spinning down the cells, the erythrocytes were removed using the red blood cell lysis buffer (Biolegend, CA, USA) followed by two washes. The T cells were further enriched using the Pan T Cell Isolation Kit II (Miltenyi, Bergisch Gladbach, Germany). A fraction of BMDCs and T cells were stained with FITC anti-mouse CD11c or FITC anti-mouse CD3 (Biolegend, CA, USA) respectively, and detected by flow cytometry for enrichment purity. BMDCs with CD11c+ purity >90% and T cells with CD3+ purity >95% were used.

For antigen-specific T cells, C57BL/6-Tg (TcraTcrb) 1100Mjb/J (OT1) or B6.Cg-Tg(TcraTcrb)425Cbn/J (OT2) mice (the Jackson Laboratory, ME, USA) at 8-16 weeks were used as T-cell donors. T cells were enriched as described above and further stained with PE Mouse Va2 TCR rat anti-mouse mAb (Invitrogen, CA, USA), and APC anti-mouse CD4 or CD8 mAb (BioLegend, CA, USA) accordingly. The double-positive cells were sorted with the BD FACS Aria II cell sorter (BD, NJ, USA).

T-Cell CFSE Labeling

After two washings in PBS with 2% FBS and 2 mM EDTA, $1\times10^7$ T cells were resuspended in 1 ml plain PBS with 2 μM CFSE (MitoSciences, OR, USA) and incubated in 37° C. for 20 min. 35 ml RPMI with 10% FBS were subsequently added to the cells and incubated for another 10 min. After the incubation, the cells were washed twice in 2% FBS and 2 mM EDTA. Cell number was determined.

Seeding of Cells $1\times10^5$ CFSE-labeled T cells and $2\times10^4$ BMDCs were seeded into 96-well plates (Corning, NY, USA) with 200 μl complete DMEM media with 10% FBS as described before. Purified NA/LE hamster anti-mouse CD3e (BD Biosciences, CA, USA) was added to the culture media at 0.1 μg/ml. For antigen-specific T cells, OVA 245-261 or OVA 323-339 peptide (Invivogen, CA, USA) was added accordingly to the culture media at 0.01 μg/ml. For IL-12 neutralizing experiment, purified NA/LE rat anti-mouse IL-12 (p40/p70) (BD Pharmingen, CA, USA) was added to the culture media at 0.2 ng/ml. Cells were cultured in humidified incubator with 5% $CO_2$ for 24 h, 48 h, or 72 h as indicated in different experiments and further analyzed using flow cytometry.

Cytokine Secretion Analysis

After 24 h of co-culturing, 100 μl supernatant was carefully collected to a new 96-well plate. The plate was sealed with an adhesive seal (BioRad, CA, USA) and stored in −20° C. The supernatant was analyzed with MILLIPLEX® MAP Mouse Cytokine/Chemokine Magnetic Bead Panel (EMD Millipore, Darmstadt, Germany) using Luminex® (Luminex, TX, USA).

Flow Cytometry

Myeloid Cells Staining

For MDSC and BMDC, only floating cells were collected. $1\times10^6$ cells were spun down in BD Falcon round-bottom polystyrene tubes (BD, NY, USA). The cell pellet was incubated with 50 μl PBS with 2% FBS with FITC anti-mouse CD11c, PE anti-mouse/human CD11b, PE-Cy7 anti-mouse Ly6G, APC anti-mouse F4/80, APC-Cy7 anti-mouse I-A (all from BioLegend, CA, USA), PerCP Cy5.5 anti-mouse Ly6C, and Fixable Viability Dye eFluor® 450 (eBioscience, CA, USA) at 4° C. for 15 min. Cells were washed once with 2 ml PBS with 2% FBS and fixed with 200 μl 1.5% PFA in 4° C. till analysis.

Costimulatory Factor Staining

Cells were treated as indicated above and stained with FITC anti-mouse CD80, PE anti-mouse CD274, PE-Cy5 anti-mouse CD40 (all from eBioscience, CA, USA), PE-Cy7 anti-mouse/human CD11b, APC anti-mouse CD86, and APC-Cy7 anti-mouse CD11c (all from BioLegend, CA, USA). Cells were fixed in 200 μl 1.5% PFA in 4° C. till analysis.

T Cells Staining

All the cells from 96-well plates were collected to flow tubes and spun down. The cell pellets were stained with PerCp-Cy5.5 anti-mouse CD69, APC anti-mouse CD8a, APC-Cy7 anti-mouse CD4 (Biolegend, CA, USA), PE-Cy7 anti-mouse CD25, and Fixable Viability Dye eFluor® 450 (eBioscience, CA, USA) at 4° C. for 15 min. Cells were further penetrated using the FoxP3 staining buffer set (eBioscience, CA, USA) as instructed and stained with PE anti-mouse/human FoxP3 (Biolegend, CA, USA). Cells were fixed in 200 μl 1.5% PFA in 4° C. until analysis.

Cell Analysis

The stained cells were analyzed using a BD FACSCanto flow cytometer (BD, NJ, USA). Flow-Count Fluorospheres (Beckman Coulter, CA, USA) were added to the sample for absolute count measurement. Data was analyzed using FlowJo (TreeStar, OR, USA).

Cytospin and Staining

MDSCs were generated as described. On Day 5, the floating cells were carefully collected and enriched by anti-mouse Gr-1 Microbeads (Miltenyi, Bergisch Gladbach, Germany). The enriched MDSCs were washed twice in plain PBS, resuspended at the concentration of $2\times10^4$ cells/2000 in complete RPMI supplied with 50% FBS, and carefully added to the assembled cuvettes with mounted slides. The cells were spun down at 500 rpm for 5 min. The slides were carefully detached from the cuvettes, dried in air for 30 min and followed by 4% paraformaldehyde (PFA) fixation for another 30 min at room temperature. The slides were stored in plain PBS at 4° C. until the Giemsa staining (Sigma-Aldrich, MO, USA) was performed as instructed.

Western Blot

To generate dry cell pellets, cells were spun down in Eppendorf tubes at 2000 rpm for 10 min with supernatant carefully removed. The cell pellets were stored at −80° C. To generate cell lysate, Halt Protease Inhibitor Cocktail and M-PER Mammalian Protein Extraction Reagent (both from ThermoFisher Scientific, MA, USA) were added to the dry pellets as instructed. The lysate was sonicated (QSonica, CT, USA) and spun down at 14,000 rpm for 10 min. The supernatant was carefully taken and aliquoted to clean Eppendorf tubes. SDS 10× loading buffer was added to the lysate and boiled at 85° C. for 5 min. 500 sample was added to each well of the Mini-PROTEAN® TGX™ Precast Gels (Bio-Rad, CA, USA) and run in SDS Tris/Glycine buffer (ThermoFisher Scientific, MA, USA) at 120V. The protein was transferred to 0.2 μm nitrocellulose membrane using Trans-Blot® Turbo transfer system (Bio-Rad, CA, USA). The membrane was blocked in Odyssey TBS blocking buffer (LI-COR Biosciences, NE, USA) at room temperature for 30 min and incubated in the first antibody at 4° C. for overnight. All the first antibodies were monoclonal, and used at 1:1000 dilution in the blocking buffer except anti-β actin at 1:5000. The first antibodies used are listed: purified mouse anti-CaM kinase kinase (BD Biosciences, CA, USA), anti-S6 ribosomal protein (54D2) mouse mAb, anti-acetyl-CoA carboxylase (C83B10) rabbit mAb, anti-phosphor-ACC (Ser79 D7D11) rabbit mAb, anti-phosphor-p38 MAPK (T180/Y182 D3F9) rabbit mAb, anti-phosphor-AMPK alpha (T172 40H9) rabbit mAb, anti-AMPK alpha (F6) mouse mAb, anti-β actin mouse mAb (all from Cell Signaling, CA, USA). After the incubation, the membranes were washed 3 times in TBST (Cell Signaling, CA, USA) for 5 min, and further incubated in secondary antibodies anti-mouse IgG Alexa Fluor 680 (Invitrogen, CA, USA) or anti-rabbit IgG IRDye800 conjugated (Rockland Immunochemicals, PA, USA) accordingly at 1:5000 dilution at room temperature for 30 min, followed by 3 washes with TBST for 5 min. The image was taken using Odyssey CLx (LI-COR, NE, USA) and analyzed using ImageStudio (LI-COR, NE, USA).

Real-Time Quantitative RT-PCR Assay

Cell pellets were generated as described before. RNA was extracted using RNeasy Mini Kit (Qiagen, Hilden, Germany) and checked for quality using a NanoDrop 2000c (Thermo Scientific, DE, USA). To synthesize first-strand cDNA, RNA sample was mixed with 10× DNaseI buffer and DNaseI at room temperature for 30 min and then with 25 mM EDTA at 65° C. for another 10 min; Oligo(dT) primer and dNTP mix were added and incubated at 72° C. for 10 min, and eventually with 5× first strand buffer, DTT, RNase-Out ribonuclease inhibitor and MLV reverse transcriptase (all reagents from Invitrogen, CA, USA) at 37° C. for 50 min and subsequently 70° C. for 15 min. Quantitative real-time PCR was performed using iQ SYBR Green Supermix (Bio-Rad, CA, USA) with respective primers and cDNA and run by the CFX96 Real-Time System (Bio-Rad, CA, USA).

TABLE 5

Primer sequences for real-time PCR assay

| Name | Sequence (5'-3')(SEQ ID NO: _) |
|---|---|
| mGAPDH-F | CCT GGA GAA ACC TGC CAA GTA TG (SEQ ID NO: 13) |
| mGAPDG-R | AGA GTG GGA GTT GCT GTT GAA GTC (SEQ ID NO: 14) |
| mARG1-F | GCA AGG TGA TGG AAG AGA C (SEQ ID NO: 15) |
| mARG1-R | CAT CGA CAT CAA AGC TCA GG (SEQ ID NO: 16) |
| mNOS2-F | GCA AAC ATC ACA TTC AGA TCC C (SEQ ID NO: 17) |
| mNOS2-R | TCA GCC TCA TGG TAA ACA CG (SEQ ID NO: 18) |
| mCAMKK2-F | CAT GAA TGG ACG CTG C (SEQ ID NO: 19) |
| mCAMKK2-R | TGA CAA CGC CAT AGG AGC C (SEQ ID NO: 20) |
| mCAT-F | CGG CAC ATG AAT GGC TAT GGA TC (SEQ ID NO: 21) |
| mCAT-R | AAG CCT TCC TGC CTC TCC AAC A (SEQ ID NO: 22) |

$RT^2$ Profiler PCR Arrays

CaMKK2 WT and KO BMDCs were generated from individual mice (n=5) and pooled during the generation of cell pellets. RNA was extracted using RNeasy Mini Kit followed by DNase clean-up using a RNase-Free DNase Set (Qiagen, Hilden, Germany) and checked for quality using a NanoDrop 2000c (Thermo Scientific, DE, USA) before proceeding to reverse transcription. cDNA was generated using $RT^2$ First Strand Kit (Qiagen, Hilden, Germany) as instructed, and further mixed with RT2 SYBR Green qPCR Mastermix (Qiagen, Hilden, Germany) and evenly distributed to the 96-well plate of RT2 Profiler™ PCR Array Mouse AMPK Signaling (Qiagen, Hilden, Germany). The reaction was performed using the CFX96 Real-Time System (Bio-Rad, CA, USA). The data was uploaded to the web resource the GeneGlobe Data Analysis Center (Qiagen, Hilden, Germany) for analysis.

Statistical Analysis

Statistical analysis was performed using Prism GraphPad (GraphPad Software, Inc. CA, USA) or Excel (Microsoft, WA, USA). For survival studies, Mantel-Cox test was used. For tumor size and bioluminescent measurement, two-way ANOVA test was used. For flow cytometry, real-time quantitative RT-PCR assay, and cytokine detection analysis, student's t test was used to compare between two groups. Level of significance was set at $P<0.05$. Bar graphs represent mean±SEM.

We claim:

1. A method of treating breast cancer in a subject comprising:

obtaining a breast tumor sample from the subject;

measuring myeloid immune cell infiltration in the sample; and determining the Immunoscore of the sample;

administering a CaMKK2 inhibitor to the subject if myeloid immune cell infiltration is detected in the sample and the Immunoscore is 2 or below;

wherein administration of the CaMKK2 inhibitor inhibits tumor growth.

2. A method of treating breast cancer in a subject comprising administering to the subject a therapeutically effective amount of a CaMKK2 inhibitor provided that the subject was selected for treatment based on detection of myeloid immune cell infiltration of a breast tumor sample from the subject, wherein administration of the CaMKK2 inhibitor inhibits tumor growth.

3. The method of claim 1, further comprising administering an anti-cancer therapeutic agent to the subject.

4. The method of claim 1, wherein the subject is human.

5. The method of claim 1, wherein the CaMKK2 inhibitor is selected from the group consisting of an siRNA, a microRNA, an antibody, and a small molecule.

6. The method of claim 1, wherein the CaMKK2 inhibitor is selected from the group consisting of STO-609 and N28464-13-A1.

7. The method of claim 3, wherein the anti-cancer therapeutic agent is selected from the group consisting of a checkpoint inhibitor, a cancer vaccine, a T cell, an oncolytic virus, and a bispecific antibody.

8. The method of claim 3, wherein the anti-cancer therapeutic agent is selected from the group consisting of an Antigen-4 (CTLA-4) inhibitor, a programmed death-1/programmed death-ligands (PD-1/PD-L) inhibitor, and a T cell immunoglobulin mucin-3 (TIM-3) inhibitor.

9. The method of claim 3, wherein the anti-cancer therapeutic agent is selected from the group consisting of an anti-CTLA-4 antibody, an anti-PD-1 antibody, and an anti-PD-L1 antibody.

* * * * *

SEQUENCE LISTING

<160> NUMBER OF SEQ ID NOS: 22

<210> SEQ ID NO 1
<211> LENGTH: 588
<212> TYPE: PRT
<213> ORGANISM: Homo sapiens
<220> FEATURE:
<221> NAME/KEY: misc_feature
<222> LOCATION: (1)..(588)
<223> OTHER INFORMATION: Human CaMKK2 (Calcium-Calmodulin kinase kinase 2) Protein

<400> SEQUENCE: 1

```
Met Ser Ser Cys Val Ser Ser Gln Pro Ser Ser Asn Arg Ala Ala Pro
1               5                   10                  15

Gln Asp Glu Leu Gly Gly Arg Gly Ser Ser Ser Ser Glu Ser Gln Lys
            20                  25                  30

Pro Cys Glu Ala Leu Arg Gly Leu Ser Ser Leu Ser Ile His Leu Gly
        35                  40                  45

Met Glu Ser Phe Ile Val Val Thr Glu Cys Glu Pro Gly Cys Ala Val
    50                  55                  60

Asp Leu Gly Leu Ala Arg Asp Arg Pro Leu Glu Ala Asp Gly Gln Glu
65                  70                  75                  80

Val Pro Leu Asp Thr Ser Gly Ser Gln Ala Arg Pro His Leu Ser Gly
                85                  90                  95

Arg Lys Leu Ser Leu Gln Glu Arg Ser Gln Gly Gly Leu Ala Ala Gly
            100                 105                 110

Gly Ser Leu Asp Met Asn Gly Arg Cys Ile Cys Pro Ser Leu Pro Tyr
        115                 120                 125

Ser Pro Val Ser Ser Pro Gln Ser Ser Pro Arg Leu Pro Arg Arg Pro
    130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190

Met Lys Val Leu Ser Lys Lys Lys Leu Ile Arg Gln Ala Gly Phe Pro
        195                 200                 205

Arg Arg Pro Pro Pro Arg Gly Thr Arg Pro Ala Pro Gly Gly Cys Ile
    210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                245                 250                 255

Asp Pro Asn Glu Asp His Leu Tyr Met Val Phe Glu Leu Val Asn Gln
            260                 265                 270

Gly Pro Val Met Glu Val Pro Thr Leu Lys Pro Leu Ser Glu Asp Gln
        275                 280                 285

Ala Arg Phe Tyr Phe Gln Asp Leu Ile Lys Gly Ile Glu Tyr Leu His
    290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                325                 330                 335

Phe Lys Gly Ser Asp Ala Leu Leu Ser Asn Thr Val Gly Thr Pro Ala
```

```
            340                 345                 350

Phe Met Ala Pro Glu Ser Leu Ser Glu Thr Arg Lys Ile Phe Ser Gly
        355                 360                 365

Lys Ala Leu Asp Val Trp Ala Met Gly Val Thr Leu Tyr Cys Phe Val
    370                 375                 380

Phe Gly Gln Cys Pro Phe Met Asp Glu Arg Ile Met Cys Leu His Ser
385                 390                 395                 400

Lys Ile Lys Ser Gln Ala Leu Glu Phe Pro Asp Gln Pro Asp Ile Ala
                405                 410                 415

Glu Asp Leu Lys Asp Leu Ile Thr Arg Met Leu Asp Lys Asn Pro Glu
            420                 425                 430

Ser Arg Ile Val Val Pro Glu Ile Lys Leu His Pro Trp Val Thr Arg
        435                 440                 445

His Gly Ala Glu Pro Leu Pro Ser Glu Asp Glu Asn Cys Thr Leu Val
    450                 455                 460

Glu Val Thr Glu Glu Glu Val Glu Asn Ser Val Lys His Ile Pro Ser
465                 470                 475                 480

Leu Ala Thr Val Ile Leu Val Lys Thr Met Ile Arg Lys Arg Ser Phe
                485                 490                 495

Gly Asn Pro Phe Glu Gly Ser Arg Arg Glu Glu Arg Ser Leu Ser Ala
            500                 505                 510

Pro Gly Asn Leu Leu Thr Lys Lys Pro Thr Arg Glu Cys Glu Ser Leu
        515                 520                 525

Ser Glu Leu Lys Glu Ala Arg Gln Arg Arg Gln Pro Pro Gly His Arg
    530                 535                 540

Pro Ala Pro Arg Gly Gly Gly Gly Ser Ala Leu Val Arg Gly Ser Pro
545                 550                 555                 560

Cys Val Glu Ser Cys Trp Ala Pro Ala Pro Gly Ser Pro Ala Arg Met
                565                 570                 575

His Pro Leu Arg Pro Glu Glu Ala Met Glu Pro Glu
            580                 585


<210> SEQ ID NO 2
<211> LENGTH: 588
<212> TYPE: PRT
<213> ORGANISM: Mus musculus
<220> FEATURE:
<221> NAME/KEY: misc_feature
<222> LOCATION: (1)..(588)
<223> OTHER INFORMATION: Mouse CaMKK2 Protein

<400> SEQUENCE: 2

Met Ser Ser Cys Val Ser Ser Gln Pro Thr Ser Asp Arg Val Ala Pro
1               5                   10                  15

Gln Asp Glu Leu Gly Ser Gly Gly Gly Ser Arg Glu Gly Gln Lys Pro
            20                  25                  30

Cys Glu Ala Leu Arg Gly Leu Ser Ser Leu Ser Ile His Leu Gly Met
        35                  40                  45

Glu Ser Phe Ile Val Val Thr Glu Cys Glu Pro Gly Arg Gly Val Asp
    50                  55                  60

Leu Asn Leu Ala Arg Asp Gln Pro Pro Glu Ala Asp Gly Gln Glu Leu
65                  70                  75                  80

Pro Leu Glu Ala Ser Asp Pro Glu Ser Arg Ser Pro Leu Ser Gly Arg
                85                  90                  95

Lys Met Ser Leu Gln Glu Pro Ser Gln Gly Gly Pro Ala Ser Ser Ser
            100                 105                 110
```

```
Asn Ser Leu Asp Met Asn Gly Arg Cys Ile Cys Pro Ser Leu Ser Tyr
        115                 120                 125

Ser Pro Ala Ser Ser Pro Gln Ser Ser Pro Arg Met Pro Arg Arg Pro
    130                 135                 140

Thr Val Glu Ser His His Val Ser Ile Thr Gly Leu Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190

Met Lys Val Leu Ser Lys Lys Lys Leu Ile Arg Gln Ala Gly Phe Pro
        195                 200                 205

Arg Arg Pro Pro Pro Arg Gly Ala Arg Pro Ala Pro Gly Gly Cys Ile
    210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                245                 250                 255

Asp Pro Asn Glu Asp His Leu Tyr Met Val Phe Glu Leu Val Asn Gln
            260                 265                 270

Gly Pro Val Met Glu Val Pro Thr Leu Lys Pro Leu Ser Glu Asp Gln
        275                 280                 285

Ala Arg Phe Tyr Phe Gln Asp Leu Ile Lys Gly Ile Glu Tyr Leu His
    290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                325                 330                 335

Phe Lys Gly Ser Asp Ala Leu Leu Ser Asn Thr Val Gly Thr Pro Ala
            340                 345                 350

Phe Met Ala Pro Glu Ser Leu Ser Glu Thr Arg Lys Ile Phe Ser Gly
        355                 360                 365

Lys Ala Leu Asp Val Trp Ala Met Gly Val Thr Leu Tyr Cys Phe Val
    370                 375                 380

Phe Gly Gln Cys Pro Phe Met Asp Glu Arg Ile Met Cys Leu His Ser
385                 390                 395                 400

Lys Ile Lys Ser Gln Ala Leu Glu Phe Pro Asp Gln Pro Asp Ile Ala
                405                 410                 415

Glu Asp Leu Lys Asp Leu Ile Thr Arg Met Leu Asp Lys Asn Pro Glu
            420                 425                 430

Ser Arg Ile Val Val Pro Glu Ile Lys Leu His Pro Trp Val Thr Arg
        435                 440                 445

His Gly Ala Glu Pro Leu Pro Ser Glu Asp Glu Asn Cys Thr Leu Val
    450                 455                 460

Glu Val Thr Glu Glu Glu Val Glu Asn Ser Val Lys His Ile Pro Ser
465                 470                 475                 480

Leu Ala Thr Val Ile Leu Val Lys Thr Met Ile Arg Lys Arg Ser Phe
                485                 490                 495

Gly Asn Pro Phe Glu Gly Ser Arg Arg Glu Glu Arg Ser Leu Ser Ala
            500                 505                 510

Pro Gly Asn Leu Leu Thr Lys Lys Pro Thr Arg Glu Trp Glu Pro Leu
        515                 520                 525
```

```
Ser Glu Pro Lys Glu Ala Arg Gln Arg Arg Gln Pro Pro Gly Pro Arg
    530                 535                 540

Ala Gly Pro Cys Gly Gly Gly Gly Ser Ala Leu Val Lys Gly Gly Pro
545                 550                 555                 560

Cys Val Glu Ser Trp Gly Ala Pro Ala Pro Gly Ser Pro Pro Arg Met
                565                 570                 575

Pro Pro Leu Gln Pro Glu Glu Val Met Glu Pro Glu
            580                 585


<210> SEQ ID NO 3
<211> LENGTH: 587
<212> TYPE: PRT
<213> ORGANISM: Rattus norvegicus
<220> FEATURE:
<221> NAME/KEY: misc_feature
<222> LOCATION: (1)..(587)
<223> OTHER INFORMATION: Rat CaMKK2 Protein

<400> SEQUENCE: 3

Met Ser Ser Cys Val Ser Ser Gln Pro Thr Ser Asp Arg Ala Ala Pro
1               5                   10                  15

Gln Asp Glu Leu Gly Ser Gly Gly Val Ser Arg Glu Ser Gln Lys Pro
            20                  25                  30

Cys Glu Ala Leu Arg Gly Leu Ser Ser Leu Ser Ile His Leu Gly Met
        35                  40                  45

Glu Ser Phe Ile Val Val Thr Glu Cys Glu Pro Gly Arg Gly Val Asp
    50                  55                  60

Leu Ser Leu Ala Arg Asp Gln Pro Leu Glu Ala Asp Gly Gln Glu Leu
65                  70                  75                  80

Pro Leu Asp Ala Ser Glu Pro Glu Ser Arg Ser Leu Leu Ser Gly Gly
                85                  90                  95

Lys Met Ser Leu Gln Glu Arg Ser Gln Gly Gly Pro Ala Ser Ser Ser
            100                 105                 110

Ser Leu Asp Met Asn Gly Arg Cys Ile Cys Pro Ser Leu Ser Tyr Ser
        115                 120                 125

Pro Ala Ser Ser Pro Gln Ser Ser Pro Arg Met Pro Arg Arg Pro Thr
    130                 135                 140

Val Glu Ser His His Val Ser Ile Thr Gly Leu Gln Asp Cys Val Gln
145                 150                 155                 160

Leu Asn Gln Tyr Thr Leu Lys Asp Glu Ile Gly Lys Gly Ser Tyr Gly
                165                 170                 175

Val Val Lys Leu Ala Tyr Asn Glu Asn Asp Asn Thr Tyr Tyr Ala Met
            180                 185                 190

Lys Val Leu Ser Lys Lys Lys Leu Ile Arg Gln Ala Gly Phe Pro Arg
        195                 200                 205

Arg Pro Pro Pro Arg Gly Thr Arg Pro Ala Pro Gly Gly Cys Ile Gln
    210                 215                 220

Pro Arg Gly Pro Ile Glu Gln Val Tyr Gln Glu Ile Ala Ile Leu Lys
225                 230                 235                 240

Lys Leu Asp His Pro Asn Val Val Lys Leu Val Glu Val Leu Asp Asp
                245                 250                 255

Pro Asn Glu Asp His Leu Tyr Met Val Phe Glu Leu Val Asn Gln Gly
            260                 265                 270

Pro Val Met Glu Val Pro Thr Leu Lys Pro Leu Ser Glu Asp Gln Ala
        275                 280                 285

Arg Phe Tyr Phe Gln Asp Leu Ile Lys Gly Ile Glu Tyr Leu His Tyr
```

```
    290                 295                 300

Gln Lys Ile Ile His Arg Asp Ile Lys Pro Ser Asn Leu Leu Val Gly
305                 310                 315                 320

Glu Asp Gly His Ile Lys Ile Ala Asp Phe Gly Val Ser Asn Glu Phe
                325                 330                 335

Lys Gly Ser Asp Ala Leu Leu Ser Asn Thr Val Gly Thr Pro Ala Phe
            340                 345                 350

Met Ala Pro Glu Ser Leu Ser Glu Thr Arg Lys Ile Phe Ser Gly Lys
        355                 360                 365

Ala Leu Asp Val Trp Ala Met Gly Val Thr Leu Tyr Cys Phe Val Phe
    370                 375                 380

Gly Gln Cys Pro Phe Met Asp Glu Arg Ile Met Cys Leu His Ser Lys
385                 390                 395                 400

Ile Lys Ser Gln Ala Leu Glu Phe Pro Asp Gln Pro Asp Ile Ala Glu
                405                 410                 415

Asp Leu Lys Asp Leu Ile Thr Arg Met Leu Asp Lys Asn Pro Glu Ser
            420                 425                 430

Arg Ile Val Val Pro Glu Ile Lys Leu His Pro Trp Val Thr Arg His
        435                 440                 445

Gly Ala Glu Pro Leu Pro Ser Glu Asp Glu Asn Cys Thr Leu Val Glu
    450                 455                 460

Val Thr Glu Glu Glu Val Glu Asn Ser Val Lys His Ile Pro Ser Leu
465                 470                 475                 480

Ala Thr Val Ile Leu Val Lys Thr Met Ile Arg Lys Arg Ser Phe Gly
                485                 490                 495

Asn Pro Phe Glu Gly Ser Arg Arg Glu Glu Arg Ser Leu Ser Ala Pro
            500                 505                 510

Gly Asn Leu Leu Thr Lys Lys Pro Thr Arg Glu Trp Glu Pro Leu Ser
        515                 520                 525

Glu Pro Lys Glu Ala Arg Gln Arg Arg Gln Pro Pro Gly Pro Arg Ala
    530                 535                 540

Ser Pro Cys Gly Gly Gly Gly Ser Ala Leu Val Lys Gly Gly Pro Cys
545                 550                 555                 560

Val Glu Ser Cys Gly Ala Pro Ala Pro Gly Ser Pro Pro Arg Thr Pro
                565                 570                 575

Pro Gln Gln Pro Glu Glu Ala Met Glu Pro Glu
            580                 585


<210> SEQ ID NO 4
<211> LENGTH: 578
<212> TYPE: PRT
<213> ORGANISM: Canis lupus familiaris
<220> FEATURE:
<221> NAME/KEY: misc_feature
<222> LOCATION: (1)..(578)
<223> OTHER INFORMATION: Dog CaMKK2 Protein

<400> SEQUENCE: 4

Met Ser Ser Cys Val Ser Ser Gln Pro Ser Ser Asp Pro Ala Ala Leu
1               5                   10                  15

Gln Asp Glu Leu Gly Gly Gly Ser Gly Ser Glu Gly Gln Lys Pro Cys
            20                  25                  30

Glu Ala Leu Gln Gly Leu Ser Ser Leu Ser Ile Arg Leu Gly Met Glu
        35                  40                  45

Ser Phe Ile Val Val Thr Glu Cys Glu Pro Gly Cys Ala Val Asp Arg
    50                  55                  60
```

-continued

```
Gly Leu Ser Arg Asp Arg Pro Arg Glu Ala Glu Gly Arg Lys Val Pro
65                  70                  75                  80

Leu Asp Ala Ser Ala Ser Gly Ser Gln Ala Arg Pro Gln Leu Cys Ser
                85                  90                  95

Arg Lys Leu Ser Leu Gln Glu Arg Ser Gln Leu Asp Ala Asn Gly Arg
            100                 105                 110

Cys Val His Pro Val Leu Pro His Ser Pro Val Gly Ser Pro Gln Ser
        115                 120                 125

Ser Pro Arg Leu Pro Arg Arg Pro Thr Val Glu Ser His His Val Ser
    130                 135                 140

Ile Thr Gly Met Gln Asp Cys Val Gln Leu Asn Gln Tyr Thr Leu Lys
145                 150                 155                 160

Asp Glu Ile Gly Lys Gly Ser Tyr Gly Val Val Lys Leu Ala Tyr Asn
                165                 170                 175

Glu Asn Asp Asn Thr Tyr Tyr Ala Met Lys Val Leu Ser Lys Lys Lys
            180                 185                 190

Leu Ile Arg Gln Ala Gly Phe Pro Arg Arg Pro Pro Pro Arg Gly Thr
        195                 200                 205

Arg Leu Ala Pro Gly Gly Cys Ile Gln Pro Arg Gly Pro Ile Glu Gln
    210                 215                 220

Val Tyr Gln Glu Ile Ala Ile Leu Lys Lys Leu Asp His Pro Asn Val
225                 230                 235                 240

Val Lys Leu Val Glu Val Leu Asp Asp Pro Asn Glu Asp His Leu Tyr
                245                 250                 255

Met Val Phe Glu Leu Val Asn Gln Gly Pro Val Met Glu Val Pro Thr
            260                 265                 270

Leu Lys Pro Leu Ser Glu Asp Gln Ala Arg Phe Tyr Phe Gln Asp Leu
        275                 280                 285

Ile Lys Gly Ile Glu Tyr Leu His Tyr Gln Lys Ile Ile His Arg Asp
    290                 295                 300

Ile Lys Pro Ser Asn Leu Leu Val Gly Glu Asp Gly His Ile Lys Ile
305                 310                 315                 320

Ala Asp Phe Gly Val Ser Asn Glu Phe Lys Gly Ser Asp Ala Leu Leu
                325                 330                 335

Ser Asn Thr Val Gly Thr Pro Ala Phe Met Ala Pro Glu Ser Leu Ser
            340                 345                 350

Glu Thr Arg Lys Ile Phe Ser Gly Lys Ala Leu Asp Val Trp Ala Met
        355                 360                 365

Gly Val Thr Leu Tyr Cys Phe Val Phe Gly Gln Cys Pro Phe Met Asp
    370                 375                 380

Glu Arg Ile Met Cys Leu His Ser Lys Ile Lys Ser Gln Ala Leu Glu
385                 390                 395                 400

Phe Pro Asp Gln Pro Asp Ile Ala Glu Asp Leu Lys Asp Leu Ile Thr
                405                 410                 415

Arg Met Leu Asp Lys Asn Pro Glu Ser Arg Ile Val Val Pro Glu Ile
            420                 425                 430

Lys Leu His Pro Trp Val Thr Arg His Gly Ala Glu Pro Leu Pro Ser
        435                 440                 445

Glu Asp Glu Asn Cys Thr Leu Val Glu Val Thr Glu Glu Glu Val Glu
    450                 455                 460

Asn Ser Val Lys His Ile Pro Ser Leu Ala Thr Val Ile Leu Val Lys
465                 470                 475                 480
```

```
Thr Met Ile Arg Lys Arg Ser Phe Gly Asn Pro Phe Glu Gly Ser Arg
                485                 490                 495

Arg Glu Glu Arg Ser Leu Ser Ala Pro Gly Asn Leu Leu Thr Lys Lys
            500                 505                 510

Pro Thr Arg Glu Cys Glu Pro Leu Ser Glu Pro Lys Glu Ala Arg Gln
        515                 520                 525

Arg Arg Gln Pro Pro Gly Pro Arg Pro Gly Pro Arg Gly Gly Gly Gly
    530                 535                 540

Ser Ala Leu Val Lys Gly Gly Pro Cys Thr Glu Ser Trp Gly Ala Pro
545                 550                 555                 560

Ala Pro Gly Pro Arg Ala Arg Met His Pro Leu Arg Pro Asp Glu Ala
                565                 570                 575

Met Glu


<210> SEQ ID NO 5
<211> LENGTH: 578
<212> TYPE: PRT
<213> ORGANISM: Felis catus
<220> FEATURE:
<221> NAME/KEY: misc_feature
<222> LOCATION: (1)..(578)
<223> OTHER INFORMATION: Cat CaMKK2 Protein

<400> SEQUENCE: 5

Met Ser Ser Cys Val Ser Ser Gln Pro Ser Ser Asp Arg Ala Ala Leu
1               5                   10                  15

Gln Asp Glu Leu Gly Gly Gly Ala Ser Ser Glu Gly Gln Lys Pro Cys
            20                  25                  30

Glu Ala Leu Gln Gly Leu Ser Ser Leu Ser Ile Arg Leu Gly Met Glu
        35                  40                  45

Ser Phe Ile Val Val Thr Glu Cys Glu Pro Gly Cys Ala Val Asp Arg
    50                  55                  60

Gly Leu Ala Arg Asp Arg Pro Leu Glu Ala Asp Gly Gln Glu Val Pro
65                  70                  75                  80

Leu His Ala Ser Ala Ser Gly Ser Gln Val Arg Pro Gln Leu Cys Gly
                85                  90                  95

Arg Lys Leu Ser Leu Gln Glu Arg Ser Gln Leu Asp Ala Asn Gly Arg
            100                 105                 110

Cys Val His Pro Ala Leu Ser His Ser Pro Val Gly Ser Pro Gln Ser
        115                 120                 125

Ser Pro Arg Leu Pro Arg Arg Pro Thr Val Glu Ser His His Val Ser
    130                 135                 140

Ile Thr Gly Met Gln Asp Cys Val Gln Leu Asn Gln Tyr Thr Leu Lys
145                 150                 155                 160

Asp Glu Ile Gly Lys Gly Ser Tyr Gly Val Val Lys Leu Ala Tyr Asn
                165                 170                 175

Glu Asn Asp Asn Thr Tyr Tyr Ala Met Lys Val Leu Ser Lys Lys Lys
            180                 185                 190

Leu Ile Arg Gln Ala Gly Phe Pro Arg Arg Pro Pro Pro Arg Gly Thr
        195                 200                 205

Arg Pro Ala Pro Gly Gly Cys Ile Gln Pro Arg Gly Pro Ile Glu Gln
    210                 215                 220

Val Tyr Gln Glu Ile Ala Ile Leu Lys Lys Leu Asp His Pro Asn Val
225                 230                 235                 240

Val Lys Leu Val Glu Val Leu Asp Asp Pro Asn Glu Asp His Leu Tyr
                245                 250                 255
```

```
Met Val Phe Glu Leu Val Asn Gln Gly Pro Val Met Glu Val Pro Thr
            260                 265                 270

Leu Lys Pro Leu Ser Glu Asp Gln Ala Arg Phe Tyr Phe Gln Asp Leu
        275                 280                 285

Ile Lys Gly Ile Glu Tyr Leu His Tyr Gln Lys Ile Ile His Arg Asp
    290                 295                 300

Ile Lys Pro Ser Asn Leu Leu Val Gly Glu Asp Gly His Ile Lys Ile
305                 310                 315                 320

Ala Asp Phe Gly Val Ser Asn Glu Phe Lys Gly Ser Asp Ala Leu Leu
                325                 330                 335

Ser Asn Thr Val Gly Thr Pro Ala Phe Met Ala Pro Glu Ser Leu Ser
            340                 345                 350

Glu Thr Arg Lys Ile Phe Ser Gly Lys Ala Leu Asp Val Trp Ala Met
        355                 360                 365

Gly Val Thr Leu Tyr Cys Phe Val Phe Gly Gln Cys Pro Phe Met Asp
    370                 375                 380

Glu Arg Ile Met Cys Leu His Ser Lys Ile Lys Ser Gln Ala Leu Glu
385                 390                 395                 400

Phe Pro Asp Gln Pro Asp Ile Ala Glu Asp Leu Lys Asp Leu Ile Thr
                405                 410                 415

Arg Met Leu Asp Lys Asn Pro Glu Ser Arg Ile Val Val Pro Glu Ile
            420                 425                 430

Lys Leu His Pro Trp Val Thr Arg His Gly Ala Glu Pro Leu Pro Ser
        435                 440                 445

Glu Asp Glu Asn Cys Thr Leu Val Glu Val Thr Glu Glu Glu Val Glu
    450                 455                 460

Asn Ser Val Lys His Ile Pro Ser Leu Ala Thr Val Ile Leu Val Lys
465                 470                 475                 480

Thr Met Ile Arg Lys Arg Ser Phe Gly Asn Pro Phe Glu Gly Ser Arg
                485                 490                 495

Arg Glu Glu Arg Ser Leu Ser Ala Pro Gly Asn Leu Leu Thr Lys Lys
            500                 505                 510

Pro Thr Arg Glu Cys Glu Pro Leu Ser Glu Pro Lys Glu Ala Arg Gln
        515                 520                 525

Arg Arg Gln Pro Pro Gly Pro Arg Pro Ala Pro Arg Gly Gly Gly Gly
    530                 535                 540

Ser Ala Leu Val Lys Gly Gly Pro Arg Ala Glu Ser Trp Gly Ala Pro
545                 550                 555                 560

Ala Pro Gly Pro Arg Ala Arg Met His Pro Leu Arg Pro Asp Glu Ala
                565                 570                 575

Met Glu
```

<210> SEQ ID NO 6
<211> LENGTH: 583
<212> TYPE: PRT
<213> ORGANISM: Oryctolagus cuniculus
<220> FEATURE:
<221> NAME/KEY: misc_feature
<222> LOCATION: (1)..(583)
<223> OTHER INFORMATION: Rabbit CaMKK2 Protein

<400> SEQUENCE: 6

```
Met Ser Ser Cys Ile Ser Ser Gln Pro Ser Gly Asp Pro Ala Ala Pro
1               5                   10                  15

Gln Asp Asp Leu Gly Gly Gly Gly Ser Ser Ile Glu Gly Gln Lys Ser
```

```
            20                  25                  30

Cys Glu Ala Leu Arg Gly Leu Ser Ser Leu Ser Ile Arg Leu Gly Met
        35                  40                  45

Glu Ser Phe Ile Val Val Thr Glu Cys Glu Pro Gly Arg Ala Val Asp
    50                  55                  60

Leu Ser Leu Ala Gln Asp Gln Gly Pro Leu Glu Ala Asp Gly Pro Glu
65                  70                  75                  80

Val Pro Leu Asp Ala Ser Ala Ser Gln Ala Arg Pro His Leu Cys Gly
                85                  90                  95

Arg Lys Leu Ser Leu Gln Glu Arg Ser Gln Gly Arg Leu Ala Ala Ser
            100                 105                 110

Ser Ser Leu Asp Met Asn Gly Arg Cys Ile His Pro Ser Val Pro Tyr
        115                 120                 125

Ser Pro Ala Ser Ser Pro Gln Ser Ser Pro Arg Leu Pro Arg Arg Pro
    130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190

Met Lys Val Leu Ser Lys Lys Lys Leu Ile Arg Gln Ala Gly Phe Pro
        195                 200                 205

Arg Arg Pro Pro Pro Arg Gly Thr Arg Pro Ala Pro Gly Gly Cys Ile
    210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                245                 250                 255

Asp Pro Asn Glu Asp His Leu Tyr Met Val Phe Glu Leu Val Asn Gln
            260                 265                 270

Gly Pro Val Met Glu Val Pro Thr Leu Lys Pro Leu Ser Glu Asp Gln
        275                 280                 285

Ala Arg Phe Tyr Phe Gln Asp Leu Ile Lys Gly Ile Glu Tyr Leu His
    290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                325                 330                 335

Phe Lys Gly Ser Asp Ala Leu Leu Ser Asn Thr Val Gly Thr Pro Ala
            340                 345                 350

Phe Met Ala Pro Glu Ser Leu Ser Glu Thr Arg Lys Ile Phe Ser Gly
        355                 360                 365

Lys Ala Leu Asp Val Trp Ala Met Gly Val Thr Leu Tyr Cys Phe Val
    370                 375                 380

Phe Gly Gln Cys Pro Phe Met Asp Glu Arg Ile Met Cys Leu His Ser
385                 390                 395                 400

Lys Ile Lys Ser Gln Ala Leu Glu Phe Pro Asp Gln Pro Asp Ile Ala
                405                 410                 415

Glu Asp Leu Lys Asp Leu Ile Thr Arg Met Leu Asp Lys Asn Pro Glu
            420                 425                 430

Ser Arg Ile Val Val Pro Glu Ile Lys Leu His Pro Trp Val Thr Arg
        435                 440                 445
```

```
His Gly Ala Glu Pro Leu Pro Ser Glu Asp Glu Asn Cys Thr Leu Val
    450                 455                 460

Glu Val Thr Glu Glu Glu Val Glu Asn Ser Val Lys His Ile Pro Ser
465                 470                 475                 480

Leu Ala Thr Val Ile Leu Val Lys Thr Met Ile Arg Lys Arg Ser Phe
                485                 490                 495

Gly Asn Pro Phe Glu Gly Ser Arg Arg Glu Glu Arg Ser Leu Ser Ala
            500                 505                 510

Pro Gly Asn Leu Leu Thr Lys Lys Pro Thr Arg Glu Cys Glu Pro Leu
        515                 520                 525

Ser Glu Pro Lys Glu Ala Arg Gln Arg Arg Arg Gln Pro Pro Gly His
    530                 535                 540

Arg Pro His Pro Arg Ile Val Lys Gly Gly Pro Arg Ala Gly Ser Trp
545                 550                 555                 560

Gly Ala Ala Ala Pro Gly Gly Pro Ala His Met His Pro Leu Trp Pro
                565                 570                 575

Glu Glu Ala Thr Glu Pro Gln
            580


<210> SEQ ID NO 7
<211> LENGTH: 565
<212> TYPE: PRT
<213> ORGANISM: Cavia porcellus
<220> FEATURE:
<221> NAME/KEY: misc_feature
<222> LOCATION: (1)..(565)
<223> OTHER INFORMATION: Cavia CaMKK2 Protein

<400> SEQUENCE: 7

Met Ser Ser Cys Val Ser Ser Gln Pro Ser Ser Asp Arg Ala Thr Pro
1               5                   10                  15

Gln Asp Gly Ser His Glu Gly Pro Lys Pro Cys Glu Ala Leu Gln Gly
            20                  25                  30

Leu Ser Ser Leu Ser Leu Arg Leu Gly Met Glu Ser Phe Ile Val Val
        35                  40                  45

Thr Glu Cys Glu Pro Asn His Ala Gly Asp Leu Ser Leu Ala Arg Asp
    50                  55                  60

His Pro Leu Asp Ala Ser Arg Ser His Leu Ser Gly Arg Lys Leu Ser
65                  70                  75                  80

Leu Gln Glu Arg Ser Ser Gly Ala Pro Val Val Gly Ser Ser Pro Glu
                85                  90                  95

Thr Asp Gly His Cys Ile His Pro Ala Leu Pro Cys Ser Pro Val Gly
            100                 105                 110

Ser Pro Gln Leu Ser Pro Arg Leu Pro Arg Arg Pro Thr Val Glu Ser
        115                 120                 125

His His Val Ser Ile Thr Gly Leu Gln Asp Cys Val Gln Leu Asn Gln
    130                 135                 140

Tyr Thr Leu Lys Asp Glu Ile Gly Lys Gly Ser Tyr Gly Val Val Lys
145                 150                 155                 160

Leu Ala Tyr Asn Glu Asn Asp Asn Thr Tyr Tyr Ala Met Lys Val Leu
                165                 170                 175

Ser Lys Lys Lys Leu Ile Arg Gln Ala Gly Phe Pro Arg Glu Cys Gly
            180                 185                 190

Pro Ala Gly Trp Asn Ser Gly Gln Lys Glu Pro Phe Ser Pro Ser Gly
        195                 200                 205
```

```
Pro Ile Glu Gln Val Tyr Gln Glu Ile Ala Ile Leu Lys Lys Leu Asp
    210                 215                 220

His Pro Asn Val Val Lys Leu Val Glu Val Leu Asp Asp Pro Asn Glu
225                 230                 235                 240

Asp His Leu Tyr Met Val Phe Glu Leu Val Asn Gln Gly Pro Val Met
                245                 250                 255

Glu Val Pro Thr Leu Lys Pro Leu Ser Glu Asp Gln Ala Arg Phe Tyr
            260                 265                 270

Phe Gln Asp Leu Ile Lys Gly Ile Glu Tyr Leu His Phe Gln Lys Ile
        275                 280                 285

Ile His Arg Asp Ile Lys Pro Ser Asn Leu Leu Val Gly Asp Asp Gly
    290                 295                 300

His Ile Lys Ile Ala Asp Phe Gly Val Ser Asn Glu Phe Lys Gly Ser
305                 310                 315                 320

Asp Ala Leu Leu Ser Asn Thr Val Gly Thr Pro Ala Phe Met Ala Pro
                325                 330                 335

Glu Ser Leu Ser Glu Thr Arg Lys Ile Phe Ser Gly Lys Ala Leu Asp
            340                 345                 350

Val Trp Ala Met Gly Val Thr Leu Tyr Cys Phe Val Phe Gly Gln Cys
        355                 360                 365

Pro Phe Met Asp Glu Arg Ile Met Cys Leu His Ser Lys Ile Lys Ser
    370                 375                 380

Gln Ala Leu Glu Phe Pro Asp Gln Pro Asp Ile Ala Glu Asp Leu Lys
385                 390                 395                 400

Asp Leu Ile Thr Arg Met Leu Asp Lys Asn Pro Glu Ser Arg Ile Val
                405                 410                 415

Val Pro Glu Ile Lys Leu His Pro Trp Val Thr Arg His Gly Ala Glu
            420                 425                 430

Pro Leu Pro Ser Glu Asp Glu Asn Cys Thr Leu Val Glu Val Thr Glu
        435                 440                 445

Glu Glu Val Glu Asn Ser Val Lys His Ile Pro Ser Leu Ala Thr Val
    450                 455                 460

Ile Leu Val Lys Thr Met Ile Arg Lys Arg Ser Phe Gly Asn Pro Phe
465                 470                 475                 480

Asp Gly Ser Arg Arg Glu Glu Arg Ala Leu Ser Ala Pro Gly Asn Leu
                485                 490                 495

Leu Thr Lys Lys Pro Pro Arg Glu Trp Glu Pro Leu Ser Glu Pro Lys
            500                 505                 510

Glu Ala Lys Gln Arg Arg Gln Pro Ala Gly Ser Arg Pro Cys Pro Arg
        515                 520                 525

Gly Gly Gly Gly Gly Ser Ala Leu Leu Lys Gly Gly Pro Cys Thr Glu
    530                 535                 540

Ser Trp Gly Ala Ala Arg Thr His Arg Pro Gln Pro Gln Gly Glu Glu
545                 550                 555                 560

Ala Met Glu Pro Gln
                565
```

<210> SEQ ID NO 8
<211> LENGTH: 570
<212> TYPE: PRT
<213> ORGANISM: Ovis aries
<220> FEATURE:
<221> NAME/KEY: misc_feature
<222> LOCATION: (1)..(570)
<223> OTHER INFORMATION: Sheep CaMKK2 Protein

<400> SEQUENCE: 8

```
Met Ser Ser Cys Val Ser Ser Gln Pro Ser Ser Asp Arg Ala Ala Pro
1               5                   10                  15

Gln Asp Glu Leu Gly Gly Gly Gly Gly Ser Ser Ser Ser Glu Gly Gln
            20                  25                  30

Lys Pro Cys Glu Ala Leu Arg Gly Leu Ser Ser Leu Ser Ile Arg Leu
        35                  40                  45

Gly Met Glu Ser Phe Ile Val Val Thr Glu Cys Glu Pro Ala Cys Ala
    50                  55                  60

Val Asp His Gly Leu Thr Arg Asp Arg Pro Leu Glu Ala His Gly Gly
65                  70                  75                  80

Glu Ile Thr Leu Asp Ala Ser Gly Ser Gln Ala Arg Pro His Leu Ser
                85                  90                  95

Ser Arg Lys Leu Ser Leu Gln Glu Arg Ser Leu Leu Asp Ala Asn Gly
            100                 105                 110

Arg Cys Val Tyr Pro Ala Leu Pro His Ser Pro Val Gly Ser Pro Gln
        115                 120                 125

Ser Ser Pro Arg Leu His Val Ser Ile Thr Gly Met Gln Asp Cys Val
    130                 135                 140

Gln Leu Asn Gln Tyr Thr Leu Lys Asp Glu Ile Gly Lys Gly Ser Tyr
145                 150                 155                 160

Gly Val Val Lys Leu Ala Tyr Asn Glu Asn Asp Asn Thr Tyr Tyr Ala
                165                 170                 175

Met Lys Val Leu Ser Lys Lys Lys Leu Ile Arg Gln Ala Gly Phe Pro
            180                 185                 190

Arg Arg Pro Pro Pro Arg Gly Thr Arg Pro Ala Pro Gly Gly Cys Ile
        195                 200                 205

Gln Pro Arg Gly Pro Ile Glu Gln Val Tyr Gln Glu Ile Ala Ile Leu
    210                 215                 220

Lys Lys Leu Asp His Pro Asn Val Val Lys Leu Val Glu Val Leu Asp
225                 230                 235                 240

Asp Pro Asn Glu Asp His Leu Tyr Met Val Phe Glu Leu Val Asn Gln
                245                 250                 255

Gly Pro Val Met Glu Val Pro Thr Leu Lys Pro Leu Ser Glu Asp Gln
            260                 265                 270

Ala Arg Phe Tyr Phe Gln Asp Leu Ile Lys Gly Ile Glu Tyr Leu His
        275                 280                 285

Tyr Gln Lys Ile Ile His Arg Asp Ile Lys Pro Ser Asn Leu Leu Val
    290                 295                 300

Gly Glu Asp Gly His Ile Lys Ile Ala Asp Phe Gly Val Ser Asn Glu
305                 310                 315                 320

Phe Lys Gly Ser Asp Ala Leu Leu Ser Asn Thr Val Gly Thr Pro Ala
                325                 330                 335

Phe Met Ala Pro Glu Ser Leu Ser Glu Thr Arg Lys Ile Phe Ser Gly
            340                 345                 350

Lys Ala Leu Asp Val Trp Ala Met Gly Val Thr Leu Tyr Cys Phe Val
        355                 360                 365

Phe Gly Gln Cys Pro Phe Met Asp Glu Arg Ile Met Cys Leu His Ser
    370                 375                 380

Lys Ile Lys Ser Gln Ala Leu Glu Phe Pro Asp Gln Pro Asp Ile Ala
385                 390                 395                 400

Glu Asp Leu Lys Asp Leu Ile Thr Arg Met Leu Asp Lys Asn Pro Glu
                405                 410                 415
```

```
Ser Arg Ile Val Val Pro Glu Ile Lys Leu His Pro Trp Val Thr Arg
            420                 425                 430

His Gly Ala Glu Pro Leu Pro Ser Glu Asp Glu Asn Cys Thr Leu Val
        435                 440                 445

Glu Val Thr Glu Glu Glu Val Glu Asn Ser Val Lys His Ile Pro Ser
    450                 455                 460

Leu Ala Thr Val Ile Leu Val Lys Thr Met Ile Arg Lys Arg Ser Phe
465                 470                 475                 480

Gly Asn Pro Phe Glu Gly Ser Arg Arg Glu Glu Arg Ser Leu Ser Ala
                485                 490                 495

Pro Gly Asn Leu Leu Ser Lys Lys Pro Thr Arg Glu Cys Glu Pro Leu
            500                 505                 510

Ser Glu Pro Lys Glu Ala Arg Gln Arg Arg Gln Pro Pro Gly Pro Arg
        515                 520                 525

Thr Gly Pro Arg Arg Gly Gly Gly Ser Ala Leu Met Lys Gly Gly Pro
    530                 535                 540

Gly Val Glu Ser Trp Gly Val Pro Gly Pro Ser Ser Leu Glu His Thr
545                 550                 555                 560

His Pro Ala Arg Pro Asp Glu Val Met Glu
                565                 570


<210> SEQ ID NO 9
<211> LENGTH: 525
<212> TYPE: PRT
<213> ORGANISM: Ovis aries
<220> FEATURE:
<221> NAME/KEY: misc_feature
<222> LOCATION: (1)..(525)
<223> OTHER INFORMATION: Sheep CaMKK2 Protein

<400> SEQUENCE: 9

Met Ser Ser Cys Val Ser Ser Gln Pro Ser Ser Asp Arg Ala Ala Pro
1               5                   10                  15

Gln Asp Glu Leu Gly Gly Gly Gly Gly Ser Ser Ser Ser Glu Gly Gln
            20                  25                  30

Lys Pro Cys Glu Ala Leu Arg Gly Leu Ser Ser Leu Ser Ile Arg Leu
        35                  40                  45

Gly Met Glu Ser Phe Ile Val Val Thr Glu Cys Glu Pro Ala Cys Ala
    50                  55                  60

Val Asp His Gly Leu Thr Arg Asp Arg Pro Leu Glu Ala His Gly Gly
65                  70                  75                  80

Glu Ile Thr Leu Asp Ala Ser Gly Ser Gln Ala Arg Pro His Leu Ser
                85                  90                  95

Ser Arg Lys Leu Ser Leu Gln Glu Arg Ser Leu Leu Asp Ala Asn Gly
            100                 105                 110

Arg Cys Val Tyr Pro Ala Leu Pro His Ser Pro Val Gly Ser Pro Gln
        115                 120                 125

Ser Ser Pro Arg Leu His Val Ser Ile Thr Gly Met Gln Asp Cys Val
    130                 135                 140

Gln Leu Asn Gln Tyr Thr Leu Lys Asp Glu Ile Gly Lys Gly Ser Tyr
145                 150                 155                 160

Gly Val Val Lys Leu Ala Tyr Asn Glu Asn Asp Asn Thr Tyr Tyr Ala
                165                 170                 175

Met Lys Val Leu Ser Lys Lys Lys Leu Ile Arg Gln Ala Gly Phe Pro
            180                 185                 190
```

```
Arg Arg Pro Pro Pro Arg Gly Thr Arg Pro Ala Pro Gly Gly Cys Ile
        195                 200                 205

Gln Pro Arg Gly Pro Ile Glu Gln Val Tyr Gln Glu Ile Ala Ile Leu
    210                 215                 220

Lys Lys Leu Asp His Pro Asn Val Val Lys Leu Val Glu Val Leu Asp
225                 230                 235                 240

Asp Pro Asn Glu Asp His Leu Tyr Met Val Phe Glu Leu Val Asn Gln
                245                 250                 255

Gly Pro Val Met Glu Val Pro Thr Leu Lys Pro Leu Ser Glu Asp Gln
            260                 265                 270

Ala Arg Phe Tyr Phe Gln Asp Leu Ile Lys Gly Ile Glu Tyr Leu His
        275                 280                 285

Tyr Gln Lys Ile Ile His Arg Asp Ile Lys Pro Ser Asn Leu Leu Val
    290                 295                 300

Gly Glu Asp Gly His Ile Lys Ile Ala Asp Phe Gly Val Ser Asn Glu
305                 310                 315                 320

Phe Lys Gly Ser Asp Ala Leu Leu Ser Asn Thr Val Gly Thr Pro Ala
                325                 330                 335

Phe Met Ala Pro Glu Ser Leu Ser Glu Thr Arg Lys Ile Phe Ser Gly
            340                 345                 350

Lys Ala Leu Asp Val Trp Ala Met Gly Val Thr Leu Tyr Cys Phe Val
        355                 360                 365

Phe Gly Gln Cys Pro Phe Met Asp Glu Arg Ile Met Cys Leu His Ser
    370                 375                 380

Lys Ile Lys Ser Gln Ala Leu Glu Phe Pro Asp Gln Pro Asp Ile Ala
385                 390                 395                 400

Glu Asp Leu Lys Asp Leu Ile Thr Arg Met Leu Asp Lys Asn Pro Glu
                405                 410                 415

Ser Arg Ile Val Val Pro Glu Ile Lys Leu His Pro Trp Val Thr Arg
            420                 425                 430

His Gly Ala Glu Pro Leu Pro Ser Glu Asp Glu Asn Cys Thr Leu Val
        435                 440                 445

Glu Val Thr Glu Glu Glu Val Glu Asn Ser Val Lys His Ile Pro Ser
    450                 455                 460

Leu Ala Thr Val Ile Leu Val Lys Thr Met Ile Arg Lys Arg Ser Phe
465                 470                 475                 480

Gly Asn Pro Phe Glu Gly Ser Arg Arg Glu Glu Arg Ser Leu Ser Ala
                485                 490                 495

Pro Gly Asn Leu Leu Arg Lys Gln Gly Ser Glu Asp Ser Leu Gln Gly
            500                 505                 510

Pro Glu Pro Ala Pro Val Gly Glu Glu Glu Val Leu Ser
        515                 520                 525
```

<210> SEQ ID NO 10
<211> LENGTH: 579
<212> TYPE: PRT
<213> ORGANISM: Bos taurus
<220> FEATURE:
<221> NAME/KEY: misc_feature
<222> LOCATION: (1)..(579)
<223> OTHER INFORMATION: Bovine CaMKK2 Protein

<400> SEQUENCE: 10

```
Met Ser Ser Cys Ile Ser Ser Gln Pro Ser Ser Asp Arg Ala Ala Pro
1               5                   10                  15

Gln Asp Glu Leu Gly Gly Gly Gly Gly Ser Ser Ser Ser Glu Gly Gln
```

```
            20                  25                  30

Lys Pro Cys Glu Ala Leu Arg Gly Leu Ser Ser Leu Ser Ile Arg Leu
        35                  40                  45

Gly Met Glu Ser Phe Ile Val Val Thr Glu Cys Glu Pro Val Cys Ala
    50                  55                  60

Val Asp His Gly Leu Thr Arg Asp Arg Pro Leu Glu Ala His Gly Gly
65                  70                  75                  80

Glu Ile Thr Leu Asp Ala Ser Gly Ser Gln Ala Arg Pro His Leu Ser
                85                  90                  95

Gly Arg Lys Leu Ser Leu Gln Glu Arg Ser Leu Leu Asp Ala Asn Gly
            100                 105                 110

Arg Cys Val Tyr Pro Ala Leu Pro His Ser Pro Val Gly Ser Pro Gln
        115                 120                 125

Ser Ser Pro Arg Leu Pro Arg Arg Pro Thr Val Glu Ser His His Val
    130                 135                 140

Ser Ile Thr Gly Met Gln Asp Cys Val Gln Leu Asn Gln Tyr Thr Leu
145                 150                 155                 160

Lys Asp Glu Ile Gly Lys Gly Ser Tyr Gly Val Val Lys Leu Ala Tyr
                165                 170                 175

Asn Glu Asn Asp Asn Thr Tyr Tyr Ala Met Lys Val Leu Ser Lys Lys
            180                 185                 190

Lys Leu Ile Arg Gln Ala Gly Phe Pro Arg Arg Pro Pro Pro Arg Gly
        195                 200                 205

Thr Arg Pro Ala Pro Gly Gly Cys Ile Gln Pro Arg Gly Pro Ile Glu
    210                 215                 220

Gln Val Tyr Gln Glu Ile Ala Ile Leu Lys Lys Leu Asp His Pro Asn
225                 230                 235                 240

Val Val Lys Leu Val Glu Val Leu Asp Asp Pro Asn Glu Asp His Leu
                245                 250                 255

Tyr Met Val Phe Glu Leu Val Asn Gln Gly Pro Val Met Glu Val Pro
            260                 265                 270

Thr Leu Lys Pro Leu Ser Glu Asp Gln Ala Arg Phe Tyr Phe Gln Asp
        275                 280                 285

Leu Ile Lys Gly Ile Glu Tyr Leu His Tyr Gln Lys Ile Ile His Arg
    290                 295                 300

Asp Ile Lys Pro Ser Asn Leu Leu Val Gly Glu Asp Gly His Ile Lys
305                 310                 315                 320

Ile Ala Asp Phe Gly Val Ser Asn Glu Phe Lys Gly Ser Asp Ala Leu
                325                 330                 335

Leu Ser Asn Thr Val Gly Thr Pro Ala Phe Met Ala Pro Glu Ser Leu
            340                 345                 350

Ser Glu Thr Arg Lys Ile Phe Ser Gly Lys Ala Leu Asp Val Trp Ala
        355                 360                 365

Met Gly Val Thr Leu Tyr Cys Phe Val Phe Gly Gln Cys Pro Phe Met
    370                 375                 380

Asp Glu Arg Ile Met Cys Leu His Ser Lys Ile Lys Ser Gln Ala Leu
385                 390                 395                 400

Glu Phe Pro Asp Gln Pro Asp Ile Ala Glu Asp Leu Lys Asp Leu Ile
                405                 410                 415

Thr Arg Met Leu Asp Lys Asn Pro Glu Ser Arg Ile Val Val Pro Glu
            420                 425                 430

Ile Lys Leu His Pro Trp Val Thr Arg His Gly Ala Glu Pro Leu Pro
        435                 440                 445
```

```
Ser Glu Asp Glu Asn Cys Thr Leu Val Glu Val Thr Glu Glu Glu Val
    450                 455                 460

Glu Asn Ser Val Lys His Ile Pro Ser Leu Ala Thr Val Ile Leu Val
465                 470                 475                 480

Lys Thr Met Ile Arg Lys Arg Ser Phe Gly Asn Pro Phe Glu Gly Ser
                485                 490                 495

Arg Arg Glu Glu Arg Ser Leu Ser Ala Pro Gly Asn Leu Leu Gly Lys
            500                 505                 510

Lys Pro Thr Arg Glu Cys Glu Pro Leu Ser Glu Pro Lys Glu Ala Arg
        515                 520                 525

Gln Arg Arg Gln Pro Pro Gly Pro Arg Thr Gly Pro Arg Arg Gly Arg
    530                 535                 540

Gly Ser Ala Leu Met Lys Gly Gly Pro Gly Val Glu Ser Trp Gly Val
545                 550                 555                 560

Pro Gly Pro Cys Ser Leu Glu His Thr His Pro Ala Arg Pro Asp Glu
                565                 570                 575

Val Met Glu


<210> SEQ ID NO 11
<211> LENGTH: 423
<212> TYPE: PRT
<213> ORGANISM: Equus caballus
<220> FEATURE:
<221> NAME/KEY: misc_feature
<222> LOCATION: (1)..(423)
<223> OTHER INFORMATION: Horse CaMKK2 Protein

<400> SEQUENCE: 11

Pro Val Arg Pro His Phe Ser Gly Arg Lys Leu Ser Leu Gln Glu Arg
1               5                   10                  15

Ser Gln Leu Asp Ala Asn Gly Arg Cys Leu Ser Pro Arg Leu Pro Arg
            20                  25                  30

Arg Pro Thr Val Glu Ser His His Val Ser Ile Thr Gly Met Gln Asp
        35                  40                  45

Cys Val Gln Leu Asn Gln Tyr Thr Leu Lys Asp Glu Ile Gly Lys Gly
    50                  55                  60

Ser Tyr Gly Val Val Lys Leu Ala Tyr Asn Glu Asn Asp Asn Thr Tyr
65                  70                  75                  80

Tyr Ala Met Lys Val Leu Ser Lys Lys Lys Leu Ile Arg Gln Ala Gly
                85                  90                  95

Phe Pro Arg Arg Pro Pro Pro Arg Gly Thr Arg Pro Ala Pro Gly Gly
            100                 105                 110

Cys Ile Gln Pro Arg Gly Pro Ile Glu Gln Val Tyr Gln Glu Ile Ala
        115                 120                 125

Ile Leu Lys Lys Leu Asp His Pro Asn Val Val Lys Leu Val Glu Val
    130                 135                 140

Leu Asp Asp Pro Asn Glu Asp His Leu Tyr Met Val Phe Glu Leu Val
145                 150                 155                 160

Asn Gln Gly Pro Val Met Glu Val Pro Thr Leu Lys Pro Leu Ser Glu
                165                 170                 175

Asp Gln Ala Arg Phe Tyr Phe Gln Asp Leu Ile Lys Gly Ile Glu Tyr
            180                 185                 190

Leu His Tyr Gln Lys Ile Ile His Arg Asp Ile Lys Pro Ser Asn Leu
        195                 200                 205

Leu Val Gly Glu Asp Gly His Ile Lys Ile Ala Asp Phe Gly Val Ser
```

```
    210                 215                 220

Asn Glu Phe Lys Gly Ser Asp Ala Leu Leu Ser Asn Thr Val Gly Thr
225                 230                 235                 240

Pro Ala Phe Met Ala Pro Glu Ser Leu Ser Glu Thr Arg Lys Ile Phe
                245                 250                 255

Ser Gly Lys Ala Leu Asp Val Trp Ala Met Gly Val Thr Leu Tyr Cys
            260                 265                 270

Phe Val Phe Gly Gln Cys Pro Phe Met Asp Glu Arg Ile Met Cys Leu
        275                 280                 285

His Ser Lys Ile Lys Ser Gln Ala Leu Glu Phe Pro Asp Gln Pro Asp
    290                 295                 300

Ile Ala Glu Asp Leu Lys Asp Leu Ile Thr Arg Met Leu Asp Lys Asn
305                 310                 315                 320

Pro Glu Ser Arg Ile Val Val Pro Glu Ile Lys Leu His Pro Trp Val
                325                 330                 335

Thr Arg His Gly Ala Glu Pro Leu Pro Ser Glu Asp Glu Asn Cys Thr
            340                 345                 350

Leu Val Glu Val Thr Glu Glu Glu Val Glu Asn Ser Val Lys His Ile
        355                 360                 365

Pro Ser Leu Ala Thr Val Ile Leu Val Lys Thr Met Ile Arg Lys Arg
    370                 375                 380

Ser Phe Gly Asn Pro Phe Glu Gly Ser Arg Arg Glu Glu Arg Ser Leu
385                 390                 395                 400

Ser Ala Pro Gly Asn Leu Leu Thr Lys Lys Pro Thr Arg Glu Cys Glu
                405                 410                 415

Pro Leu Ser Glu Pro Lys Thr
            420


<210> SEQ ID NO 12
<211> LENGTH: 8
<212> TYPE: PRT
<213> ORGANISM: Gallus gallus
<220> FEATURE:
<221> NAME/KEY: misc_feature
<222> LOCATION: (1)..(8)
<223> OTHER INFORMATION: Ovalbumin peptide 257-264

<400> SEQUENCE: 12

Ser Ile Ile Asn Phe Glu Lys Leu
1               5


<210> SEQ ID NO 13
<211> LENGTH: 23
<212> TYPE: DNA
<213> ORGANISM: Artificial Sequence
<220> FEATURE:
<223> OTHER INFORMATION: Synthetic: mGAPDH-F

<400> SEQUENCE: 13

cctggagaaa cctgccaagt atg                                              23


<210> SEQ ID NO 14
<211> LENGTH: 24
<212> TYPE: DNA
<213> ORGANISM: Artificial Sequence
<220> FEATURE:
<223> OTHER INFORMATION: Synthetic: mGAPDG-R

<400> SEQUENCE: 14

agagtgggag ttgctgttga agtc                                             24
```

<210> SEQ ID NO 15
<211> LENGTH: 19
<212> TYPE: DNA
<213> ORGANISM: Artificial Sequence
<220> FEATURE:
<223> OTHER INFORMATION: Synthetic: mARG1-F

<400> SEQUENCE: 15
gcaaggtgat ggaagagac 19

<210> SEQ ID NO 16
<211> LENGTH: 20
<212> TYPE: DNA
<213> ORGANISM: Artificial Sequence
<220> FEATURE:
<223> OTHER INFORMATION: Synthetic: mARG1-R

<400> SEQUENCE: 16
catcgacatc aaagctcagg 20

<210> SEQ ID NO 17
<211> LENGTH: 22
<212> TYPE: DNA
<213> ORGANISM: Artificial Sequence
<220> FEATURE:
<223> OTHER INFORMATION: Synthetic: mNOS2-F

<400> SEQUENCE: 17
gcaaacatca cattcagatc cc 22

<210> SEQ ID NO 18
<211> LENGTH: 20
<212> TYPE: DNA
<213> ORGANISM: Artificial Sequence
<220> FEATURE:
<223> OTHER INFORMATION: Synthetic: mNOS2-R

<400> SEQUENCE: 18
tcagcctcat ggtaaacacg 20

<210> SEQ ID NO 19
<211> LENGTH: 16
<212> TYPE: DNA
<213> ORGANISM: Artificial Sequence
<220> FEATURE:
<223> OTHER INFORMATION: Synthetic: mCAMKK2-F

<400> SEQUENCE: 19
catgaatgga cgctgc 16

<210> SEQ ID NO 20
<211> LENGTH: 19
<212> TYPE: DNA
<213> ORGANISM: Artificial Sequence
<220> FEATURE:
<223> OTHER INFORMATION: Synthetic: mCAMKK2-R

<400> SEQUENCE: 20
tgacaacgcc ataggagcc 19

<210> SEQ ID NO 21
<211> LENGTH: 23
<212> TYPE: DNA
<213> ORGANISM: Artificial Sequence
<220> FEATURE:

-continued

```
<223> OTHER INFORMATION: Synthetic: mCAT-F

<400> SEQUENCE: 21

cggcacatga atggctatgg atc                                           23


<210> SEQ ID NO 22
<211> LENGTH: 22
<212> TYPE: DNA
<213> ORGANISM: Artificial Sequence
<220> FEATURE:
<223> OTHER INFORMATION: Synthetic: mCAT-R

<400> SEQUENCE: 22

aagccttcct gcctctccaa ca                                            22
```